(12) United States Patent
Trieu et al.

(10) Patent No.: US 7,332,568 B2
(45) Date of Patent: Feb. 19, 2008

(54) Q3 SPARC DELETION MUTANT AND USES THEREOF

(75) Inventors: Vuong Trieu, Calabasas, CA (US); Neil P. Desai, Santa Monica, CA (US); Patrick Soon-Shiong, Los Angeles, CA (US)

(73) Assignee: Abraxis BioScience, Inc., Los Angeles, CA (US)

( * ) Notice: Subject to any disclaimer, the term of this patent is extended or adjusted under 35 U.S.C. 154(b) by 22 days.

(21) Appl. No.: 11/356,829

(22) Filed: Feb. 17, 2006

(65) Prior Publication Data

US 2006/0199248 A1 Sep. 7, 2006

Related U.S. Application Data

(60) Provisional application No. 60/654,261, filed on Feb. 18, 2005.

(51) Int. Cl.
*A61K 38/00* (2006.01)
*A61K 51/00* (2006.01)
*C07K 14/00* (2006.01)

(52) U.S. Cl. .................... 530/300; 514/2; 424/1.37; 424/152.1

(58) Field of Classification Search .............. None
See application file for complete search history.

(56) References Cited

U.S. PATENT DOCUMENTS

| | | | |
|---|---|---|---|
| 5,128,247 | A | 7/1992 | Koller |
| 5,130,423 | A | 7/1992 | Van Ness et al. |
| 5,674,743 | A | 10/1997 | Ulmer |
| 5,945,515 | A | 8/1999 | Chomczynski |
| 5,962,320 | A | 10/1999 | Robinson |
| 6,025,136 | A | 2/2000 | Drmanac |
| 6,187,307 | B1 | 2/2001 | Cohen |
| 6,194,205 | B1 | 2/2001 | Staege et al. |
| 6,270,961 | B1 | 8/2001 | Drmanac |
| 6,316,193 | B1 | 11/2001 | He et al. |
| 6,387,664 | B1 | 5/2002 | Ikemoto |
| 2003/0118579 | A1 | 6/2003 | Walker et al. |

FOREIGN PATENT DOCUMENTS

| | | |
|---|---|---|
| WO | WO 01/20989 A1 | 3/2001 |
| WO | WO 01/81631 A1 | 11/2001 |
| WO | WO 02/090544 A2 | 11/2002 |
| WO | WO 2004/005883 A2 | 1/2004 |
| WO | WO 2004/064785 A2 | 8/2004 |
| WO | WO 2004/091383 A2 | 10/2004 |
| WO | WO 2005/117952 A2 | 12/2005 |

OTHER PUBLICATIONS

Altschul et al., *FEBS Journal*, 272, 5101-5109 (2005).
Aydin et al., *Biotechniques*, 31(4), 920-928 (Oct. 2001).
Beaucage et al., *Tetrahedron Letters*, 22(20), 1859-1862 (1981).
Bellahcène et al., *American Journal of Pathology*, 146(1), 95-100 (Jan. 1995).
Berg et al., *Biochem. J.*, 307, 313-326 (1995).
Bortolin et al., *Clinical Chemistry*, 50, 2028-2036 (2004).
Bradford, *Analytical Chemistry*, 72, 248-254 (1976).
Bradshaw et al., *J. of Clinical Investigation*, 107(9), 1049-1054 (May 2001).
Bradshaw et al., *PNAS*, 100(10), 6045-6050 (May 13, 2003).
Chlenski et al, *Cancer Research*, 62, 7357-7363 (Dec. 15, 2002).
Damascelli et al., *Cancer*, 92(10), 2592-2602 (Nov. 15, 2001).
Damascelli et al., *AJR*, 181, 253-260 (Jul. 2003).
De Felipe et al., *Gene Therapy*, 6, 198-208 (1999).
Desai et al., 26th *Annual San Antonio Breast Cancer Symposium* — "Poster Session: Treatment: Chemotherapy—New Drugs and Formulations" (Dec. 4, 2003).
Dhanesuan et al., *Breast Cancer Research and Treatment*, 75, 73-85 (2002).
Freeman et al., *J. of Molecular Diagnostics*, 4(4), 209-215 (Nov. 2002).
Fuglsang, *Protein Expression and Purification*, 31, 247-249 (2003).
Garnett, *Advanced Drug Delivery Reviews*, 53, 171-216 (2001).
GenBank Accession No. NM 003118: *Homo sapiens* Secreted Protein, Acidic, Cysteine-rich (Osteonectin) (SPARC), mRNA (Dec. 4, 2005).
Georgiou, *Current Opinion in Biotechnology*, 7, 190-197 (1996).
Gilbert et al., *Kidney International*, 48, 1216-1225 (1995).
Gilles et al., *Nature Biotech.*, 17, 365-370 (Apr. 1999).
Greenwald et al., *Advanced Drug Delivery Reviews*, 55, 217-250 (2003).
Haff et al., *Nucleic Acids Research*, 25(18), 3749-3750 (1997).
Harlow and Lane, *Antibodies: A Laboratory Manual*, Cold Spring Harbor Laboratory Press, Cold Spring Harbor, New York (1988).
Hasselaar et al., *J. of Biological Chemistry*, 266(20), 13178-13184 (Jul. 15, 1991).
Hawkins et al., *Human Mutation*, 19, 543-553 (2002).
Hohenadl et al., *J. Biological Chemistry*, 270(40), 23415-23420 (Oct. 6, 1995).
Hooper et al., *Biochem. J.*, 321, 265-279 (1997).
Jayaraj et al., *Nucleic Acids Research*, 33(9), 3011-3016 (2005).
John et al., *Am. J. Physiol. Lung Cell Mol. Physiol.*, 284, L187-L196 (2003).

(Continued)

*Primary Examiner*—Robert Mondesi
*Assistant Examiner*—Anand Desai
(74) *Attorney, Agent, or Firm*—Leydig, Voit & Mayer, Ltd.

(57) ABSTRACT

The invention provides for SPARC polypeptides with a mutation corresponding to a deletion of the third glutamine in the mature form of the human SPARC protein, nucleic acids encoding such polypeptides, antibodies against such polypeptides, and methods of the use of such polypeptides, nucleic acids, and antibodies.

5 Claims, 38 Drawing Sheets

OTHER PUBLICATIONS

Kim et al., *J. Korean Med. Sci.*, 13, 652-657 (1998).
Kirkpatrick et al., *Nature Cell Biology*, 750-757 (Aug. 2005).
Kozak, *J. Mol. Biol.*, 196, 947-950 (1987).
Lane et al., *FASEB J.*, 8, 163-173 (Feb. 1994).
Lowry et al., *J. Biological Chem.*, 193, 265-275 (1951).
Mason et al., *EMBO J.*, 5(7), 1465-1472 (1986).
Matteucci et al., *Biotechnology*, 24, 92-98 (1992).
Maxam et al., Proc. Natl. Acad. Sci. USA, 74(2), 560-564 (Feb. 1977).
Mills et al., *Proc. Natl. Acad. Sci. USA*, 76(5), 2232-2235 (May 1979).
Murakami et al, *Biochemical and Biophysical Research Communications*, 146(3), 1249-1255 (Aug. 14, 1987).
O'Shaughnessy et al., "ABI-007 (ABRAXANE™), a Nanoparticle Albumin-Bound (nab) Paclitaxel Demonstrates Superior *Efficacy* vs.*Taxol* in MBC: A Phase III Trial," *26th Annual San Antonio Breast Cancer Symposium*, San Antonio, Texas (Dec. 5, 2003).
Parikh et al., *Biotechniques*, 24, 428-431 (Mar. 1998).
Patil et al., *AAPS Journal*, 7(1), E61-E77 (2005).
Patolsky et al., *Nature Biotechnology*, 19, 253-257 (Mar. 2001).
Peattie, *Proc. Natl. Acad. Sci. USA*, 76(4), 1760-1764 (Apr. 1979).
Pichler et al., *Am. J. of Pathology*, 148(4), 1153-1167 (Apr. 1996).
Porter et al, *J. Histochemistry and Cytochemistry*, 43(8), 791-800 (1995).
Qi et al, *Nucleic Acids Research*, 29(22) e116 (2001).
Raines et al., *Proc. Natl. Acad. Sci. USA*, 89, 1281-1285 (Feb. 1992).
Rempel et al., *Clinical Cancer Research*, 5, 237-341 (Feb. 1999).
Rosenberg, *BMC Bioinformatics*, 6, 278 (Nov. 23, 2005).
Sage et al., *J. Cellular Biochemistry*, 57, 127-140 (1995).
Sage et al., *J. Biological Chemistry*, 278(39) 37849-37857 (Sep. 26, 2003).
Sambrook et al., *Molecular Cloning: A Laboratory Manual*, pp. 9.14-9.23, Cold Spring Harbor Laboratory Press, New York, (1989).
Sambrook and Russell, *Molecular Cloning: A Laboratory Manual*, pp. 1.1-1.162, Cold Spring Harbor Laboratory Press, New York, (2001).
Sambrook and Russell, *Molecular Cloning: A Laboratory Manual*, pp. 6.1-6.62, Cold Spring Harbor Laboratory Press, New York, (2001).
Sambrook and Russell, *Molecular Cloning: A Laboratory Manual*, pp. 15.1-15.53, Cold Spring Harbor Laboratory Press, New York, (2001).
Sambrook and Russell, *Molecular Cloning: A Laboratory Manual*, pp. 16.1-16.54, Cold Spring Harbor Laboratory Press, New York, (2001).
Sanger et al., *Proc. Natl. Acad. Sci.* USA, 74(12), 5463-5467 (Dec. 1977).
Schecter et al., *Biochemical and Biophysical Research Communications*, 27(2), 157-162 (1967).
Schnitzer et al., *J. Biological Chemistry*, 269(8), 6072-6082 (1994).
Shapiro, *Practical Flow Cytometry*, 3rd ed., New York, Wiley-Liss, 217-228(1995).
Smith et al., *Anal. Biochem.* 150(1), 76-85 (Oct. 1985).
Smyth et al., *Immunology Today*, 16(4), 202-206 (1995).
Sparreboom et al., *Cancer Research*, 59, 1454-1457 (Apr. 1, 1999).
Swaroop et al., *Genomics*, 2, 37-47 (1988).
Takahashi et al., *Obesity Res.*, 9(7) 388-393 (Jul. 2001).
Talanian et al., *J. Biological Chem.*, 272(15), 9677-9682 (Apr. 11, 1997).
Thornberry et al., *J. Biological Chem.*, 272(29), 17907-17911 (Jul. 18, 1997).
Tomita et al., *J. Biological Chem.*, 279(52), 54161-54172 (Dec. 24, 2004).
Villahermosa et al., *J. Human Virology*, 4, 238-248 (2001).
Werb, *Cell*, 91, 439-442 (Nov. 14, 1997).
Wolfsberg et al., *J. Cell Biology*, 131(2) 275-278 (Oct. 1995).
Wu et al., "The Synthetic Gene Designer: A Flexible Web Platform to Explore Sequence Space of Synthetic Genes for Heterologous Expression" *CSBW'05*, (2005).
Yamanaka et al., *J. Urology*, 166, 2495-2499 (Dec. 2001).
Yan et al., *J. Histochemistry & Cytochemistry*, 47(12), 1495-1505 (1999).
Yiu et al., *Am. J. Pathology*, 159(2), 609-622 (Aug. 2001).
Zimmern et al., *Proc. Natl. Acad. Sci. USA*, 75(9), 4257-4261 (Sep. 1978).
Puolakkainen et al., *Molecular Cancer Research*, 2, 215-224 (Apr. 2004).
Schnltzer et al., *Am. J. Physiology—Heart and Circulatory Physiology*, 32(6), H1872-H1879 (Dec. 1992).
Search Report for International Patent Application No. PCT/US2006/005615 (Search completed Feb. 2, 2007).

Fig. 1
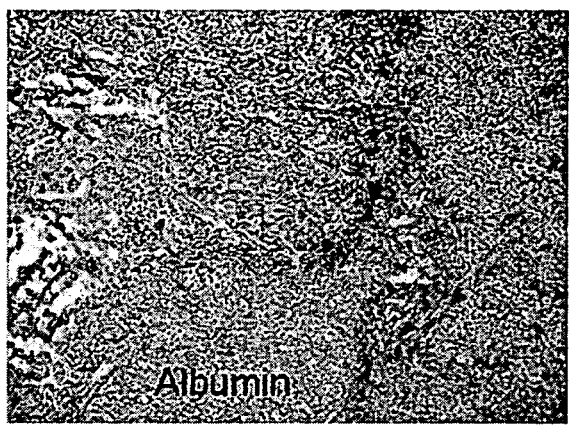 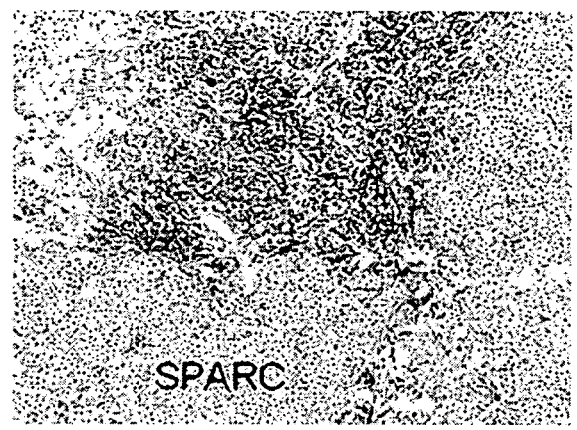

Transcytosis of Paclitaxel across Endothelial Cell Monolayers

Fig. 4A

```
                        1                                                      50
                   (1)
      Consensus   (2) CTCCACATTCCCGCGGTCCTTCAGACTGCCCGGAGAGCGCGCTCTGCCTG
   » NM_003118    (2) CTCCACATTCCCGCGGTCCTTCAGACTGCCCGGAGAGCGCGCTCTGCCTG
       « p_r1     (2) CTCCACATTCCCGCGGTCCTTCAGACTGCCCGGAGAGCGCGCTCTGCCTG
       « p_r1 (2) (2) CTCCACATTCCCGCGGTCCTTCAGACTGCCCGGAGAGCGCGCTCTGCCTG
       » Origene5 (2) CTCCACATTCCCGCGGTCCTTCAGACTGCCCGGAGAGCGCGCTCTGCCTG
       » R1_P1    (2) CTCCACATTCCCGCGGTCCTTCAGACTGCCCGGAGAGCGCGCTCTGCCTG
       « R2_p2    (1)
       « p_r2     (1)
  » R1-1-9-06_P1  (1)
       » p_F1 (2) (1)
       « r1_p2    (1)
       « p_r3     (1)
       » p_F2 (2) (1)
       « Origene3 (1)

51                                                     100
                  (51)                      +
      Consensus  (52) CCGCCTGCCTGCCTGCCACTGAGGGTTCCCAGCACCATGAGGGCCTGGAT
   » NM_003118   (52) CCGCCTGCCTGCCTGCCACTGAGGGTTCCCAGCACCATGAGGGCCTGGAT
       « p_r1    (52) CCGCCTGCCTGCCTGCCACTGAGGGTTCCCAGCACCATGAGGGCCTGGAT
       « p_r1 (2)(52) CCGCCTGCCTGCCTGCCACTGAGGGTTCCCAGCACCATGAGGGCCTGGAT
       » Origene5(52) CCGCCTGCCTGCCTGCCACTGAGGGTTCCCAGCACCATGAGGGCCTGGAT
       » R1_P1   (52) CCGCCTGCCTGCCTGCCACTGAGGGTTCCCAGCACCATGAGGGCCTGGAT
       « R2_p2    (1)                     TGAGGGTTCCCAGCACCATGAGGGCCTGGAT
       « p_r2     (1)                         TCCCAGCACCATGA-GGCCTGGAT
  » R1-1-9-06_P1  (1)
       » p_F1 (2) (1)
       « r1_p2    (1)
       « p_r3     (1)
       » p_F2 (2) (1)
       « Origene3 (1)

101                                                    150
                 (101)  ·+ ·        ·              ·    +  ·       +++++
      Consensus (102) CTTCTTTCTCCTTTGCCTGGCCGGGAGGGCCTTGGCAGCCCCT---CAAG
   » NM_003118  (102) CTTCTTTCTCCTTTGCCTGGCCGGGAGGGCCTTGGCAGCCCCTCAGCAAG
       « p_r1   (102) CTTCTTTCTCCTT
       « p_r1 (2)(102) CTTCTTTCTCCTT
       » Origene5(102) CTTCTTTCTCCTTTGCCTGGCCGGGAGGGCCTTGGCAGCCCCT---CAAG
       » R1_P1  (102) CTTCTTTCTCCTTTGCCTGGCCGGGAGGGCCTTGGCAGCCCCT---CAAG
       « R2_p2   (33) C-TNTTTCTCCTTTGCCTGGNCGGGAGGGCCTTGGCAGCCCCT---CAAG
       « p_r2    (26) NTTCTTTNTCCTTTGCCTGGCCGGGA-GGNCTTGGCAGCCCT----CAAG
  » R1-1-9-06_P1  (1)
       » p_F1 (2) (1)
       « r1_p2    (1)
       « p_r3     (1)
       » p_F2 (2) (1)
       « Origene3 (1)
```

Fig. 4B

```
                              151                                                              200
                        (151)
       Consensus       (152)  AAGCCCTGCCTGATGAGACAGAGGTGGTGGAAGAAACTGTGGCAGAGGTG
    » NM_003118        (152)  AAGCCCTGCCTGATGAGACAGAGGTGGTGGAAGAAACTGTGGCAGAGGTG
         « p_r1        (•113)
     « p_r1 (2)        (•113)
      » Origene5       (152)  AAGCCCTGCCTGATGAGACAGAGGTGGTGGAAGAAACTGTGGCAGAGGTG
         » R1_P1       (152)  AAGCCCTGCCTGATGAGACAGAGGTGGTGGAAGAAACTGTGGCAGAGGTG
         « R2_p2       (83)   AAGCCCTGCCTGATGAGACAGAGGTGGTGGAAGAAACTGTGGCAGAGGTG
          « p_r2       (76)   AAGCCCTGCCTGATGAGACAGAGGTGGTGGAAGAAACTGTGGCAGAGGTG
    » R1-1-9-06_P1     (1)
       » p_F1 (2)      (1)
         « r1_p2       (1)
          « p_r3       (1)
       » p_F2 (2)      (1)
      « Origene3       (1)
                              201                           . .                                250
                        (201)
       Consensus       (202)  ACTGAGGTATCTGTGGGAGCTAATCCTGTCCAGGTGGAAGTAGGAGAATT
    » NM_003118        (202)  ACTGAGGTATCTGTGGGAGCTAATCCTGTCCAGGTGGAAGTAGGAGAATT
         « p_r1        (•113)
     « p_r1 (2)        (•113)
      » Origene5       (202)  ACTGAGGTATCTGTGGGAGCTAATCCTGTCCAGGTGGAAGTAGGAGAATT
         » R1_P1       (202)  ACTGAGGTATCTGTGGGAGCTAATCCTGTCCAGGTGGAAGTAGGAGAATT
         « R2_p2       (133)  ACTGAGGTATCTGTGGGAGCTAATCCTGNNCAGGTGGAAGTAGGAGAATT
          « p_r2       (126)  ACTGAGGTATCTGTGGGAGCTAATCCTG-NCAGGTGGAAGTAGGAGAATT
    » R1-1-9-06_P1     (1)
       » p_F1 (2)      (1)
         « r1_p2       (1)
          « p_r3       (1)
       » p_F2 (2)      (1)
      « Origene3       (1)
                              251                                                              300
                        (251)
       Consensus       (252)  TGATGATGGTGCAGAGGAAACCGAAGAGGAGGTGGTGGCGGAAAATCCCT
    » NM_003118        (252)  TGATGATGGTGCAGAGGAAACCGAAGAGGAGGTGGTGGCGGAAAATCCCT
         « p_r1        (•113)
     « p_r1 (2)        (•113)
      » Origene5       (252)  TGATGATGGTGCAGAGGAAACCGAAGAGGAGGTGGTGGCGGAAAATCCCT
         » R1_P1       (252)  TGATGATGGTGCAGAGGAAACCGAAGAGGAGGTGGTGGCGGAAAATCCCT
         « R2_p2       (183)  TGATGATGGTGCAGAGGAAACCGAAGAGGAGGTGGTGGCGGAAAATCCCT
          « p_r2       (176)  TGATGATGGTGCAGAGGAAACCGAAGAGGAGGTGGTGGCGGAAAATCCCT
    » R1-1-9-06_P1     (1)
       » p_F1 (2)      (1)
         « r1_p2       (1)
          « p_r3       (1)
       » p_F2 (2)      (1)
      « Origene3       (1)
```

Fig. 4C

|  |  | 301 | 350 |
|---|---|---|---|
|  | (301) |  |  |
| Consensus | (302) | GCCAGAACCACCACTGCAAACACGGCAAGGTGTGCGAGCTGGATGAGAAC | |
| » NM_003118 | (302) | GCCAGAACCACCACTGCAAACACGGCAAGGTGTGCGAGCTGGATGAGAAC | |
| « p_r1 | (•113) | | |
| « p_r1 (2) | (•113) | | |
| » Origene5 | (302) | GCCAGAACCACCACTGCAAACACGGCAAGGTGTGCGAGCTGGATGAGAAC | |
| » R1_P1 | (302) | GCCAGAACCACCACTGCAAACACGGCAAGGTGTGCGAGCTGGATGAGAAC | |
| « R2_p2 | (233) | GCCAGAACCACCACTGCAAACACGGCAAGGTGTGCGAGCTGGATGAGAAC | |
| « p_r2 | (226) | GCCAGAACCACCACTGCAAACACGGCAAGGTGTGCGAGCTGGATGAGAAC | |
| » R1-1-9-06_P1 | (1) | | |
| » p_F1 (2) | (1) | | |
| « r1_p2 | (1) | | |
| « p_r3 | (1) | | |
| » p_F2 (2) | (1) | | |
| « Origene3 | (1) | | |

|  |  | 351 | 400 |
|---|---|---|---|
|  | (351) | | |
| Consensus | (352) | AACACCCCCATGTGCGTGTGCCAGGACCCCACCAGCTGCCCAGCCCCAT | |
| » NM_003118 | (352) | AACACCCCCATGTGCGTGTGCCAGGACCCCACCAGCTGCCCAGCCCCAT | |
| « p_r1 | (•113) | | |
| « p_r1 (2) | (•113) | | |
| » Origene5 | (352) | AACACCCCCATGTGCGTGTGCCAGGACCCCACCAGCTGCCCAGCCCCAT | |
| » R1_P1 | (352) | AACACCCCCATGTGCGTGTGCCAGGACCCCACCAGCTGCCCAGCCCCAT | |
| « R2_p2 | (283) | AACACCCCCATGTGCGTGTGCCAGGACCCCACCAGCTGCCCAGCCCCAT | |
| « p_r2 | (276) | AACACCCCCATGTGCGTGTGCCAGGACCCCACCAGCTGCCCAGCCCCAT | |
| » R1-1-9-06_P1 | (1) | | |
| » p_F1 (2) | (1) | | |
| « r1_p2 | (1) | | |
| « p_r3 | (1) | | |
| » p_F2 (2) | (1) | | |
| « Origene3 | (1) | | |

|  |  | 401 | 450 |
|---|---|---|---|
|  | (401) | | |
| Consensus | (402) | TGGCGAGTTTGAGAAGGTGTGCAGCAATGACAACAAGACCTTCGACTCTT | |
| » NM_003118 | (402) | TGGCGAGTTTGAGAAGGTGTGCAGCAATGACAACAAGACCTTCGACTCTT | |
| « p_r1 | (•113) | | |
| « p_r1 (2) | (•113) | | |
| » Origene5 | (402) | TGGCGAGTTTGAGAAGGTGTGCAGCAATGACAACAAGACCTTCGACTCTT | |
| » R1_P1 | (402) | TGGCGAGTTTGAGAAGGTGTGCAGCAATGACAACAAGACCTTCGACTCTT | |
| « R2_p2 | (333) | TGGCGAGTTTGAGAAGGTGTGCAGCAATGACAACAAGACCTTCGACTCTT | |
| « p_r2 | (326) | TGGCGAGTTTGAGAAGGTGTGCAGCAATGACAACAAGACCTTCGACTCTT | |
| » R1-1-9-06_P1 | (1) | | |
| » p_F1 (2) | (1) | | |
| « r1_p2 | (1) | | |
| « p_r3 | (1) | | |
| » p_F2 (2) | (1) | | |
| « Origene3 | (1) | | |

Fig. 4D

```
                                451                                              500
                       (451)
         Consensus     (452)   CCTGCCACTTCTTTGCCACAAAGTGCACCCTGGAGGGCACCAAGAAGGGC
      » NM_003118      (452)   CCTGCCACTTCTTTGCCACAAAGTGCACCCTGGAGGGCACCAAGAAGGGC
           « p_r1      (•113)
         « p_r1 (2)    (•113)
         » Origene5    (452)   CCTGCCACTTCTTTGCCACAAAGTGCACCCTGGAGGGCACCAAGAAGGGC
            » R1_P1    (452)   CCTGCCACTTCTTTGCCACAAAGTGCACCCTGGAGGGCACCAAGAAGGGC
            « R2_p2    (383)   CCTGCCACTTCTTTGCCACAAAGTGCACCCTGGAGGGCACCAAGAAGGGC
             « p_r2    (376)   CCTGCCACTTCTTTGCCACAAAGTGCACCCTGGAGGGCACCAAGAAGGGC
      » R1-1-9-06_P1   (1)
         » p_F1 (2)    (1)
            « r1_p2    (1)
             « p_r3    (1)
         » p_F2 (2)    (1)
         « Origene3    (1)
                                501                                              550
                       (501)
         Consensus     (502)   CACAAGCTCCACCTGGACTACATCGGGCCTTGCAAATACATCCCCCCTTG
      » NM_003118      (502)   CACAAGCTCCACCTGGACTACATCGGGCCTTGCAAATACATCCCCCCTTG
           « p_r1      (•113)
         « p_r1 (2)    (•113)
         » Origene5    (502)   CACAAGCTCCACCTGGACTACATCGGGCCTTGCAAATACATCCCCCCTTG
            » R1_P1    (502)   CACAAGCTCCACCTGGACTACATCGGGCCTTGCAAATACATCCCCCCTTG
            « R2_p2    (433)   CACAAGCTCCACCTGGACTACATCGGGCCTTGCAAATACATCCCCCCTTG
             « p_r2    (426)   CACAAGCTCCACCTGGACTACATCGGGCCTTGCAAATACATCCCCCCTTG
      » R1-1-9-06_P1   (1)
         » p_F1 (2)    (1)
            « r1_p2    (1)
             « p_r3    (1)
         » p_F2 (2)    (1)
         « Origene3    (1)
                                551              +                               600
                       (551)
         Consensus     (552)   CCTGGACTCTGAGCTGACCGAATTCCCCCTGCGCATGCGGGACTGGCTCA
      » NM_003118      (552)   CCTGGACTCTGAGCTGACCGAATTCCCCCTGCGCATGCGGGACTGGCTCA
           « p_r1      (•113)
         « p_r1 (2)    (•113)
         » Origene5    (552)   CCTGGACTCTGAGCTGACCGAATTCCCCCTGCGCATGCGGGACTGGCTCA
            » R1_P1    (552)   CCTGGACTCTGAGCTGACCGAATTCCCCCTGCGCATGCGGGACTGGCTCA
            « R2_p2    (483)   CCTGGACTTTGAGCTGACCGAATTCCCCCTGCGCATGCGGGACTGGCTCA
             « p_r2    (476)   CCTGGACTTTGAGCTGACCGAATTCCCCCTGCGCATGCGGGACTGGCTCA
      » R1-1-9-06_P1   (1)
         » p_F1 (2)    (1)
            « r1_p2    (1)
             « p_r3    (1)
         » p_F2 (2)    (1)
         « Origene3    (1)
```

Fig. 4E

```
                           601                                                      650
                  (601)                  +
     Consensus    (602)  AGAACGTCCTGGTCACCCTGTATGAGAGGGATGAGGACAACAACCTTCTG
  » NM_003118     (602)  AGAACGTCCTGGTCACCCTGTATGAGAGGGATGAGGACAACAACCTTCTG
         « p_r1   (•113)
       « p_r1 (2) (•113)
     » Origene5   (602)  AGAACGTCCTGGTCACCCTGTATGAGAGGGATGAGGACAACAACCTTCTG
        » R1_P1   (602)  AGAACGTCCTGGTCACCCTGTATGAGAGGGATGAGGACAACAACCTTCTG
        « R2_p2   (533)  AGAACGTCCTGGTCACCCTGTATGAGAGGGATGAGGACAACAACCTTTTG
         « p_r2   (526)  AGAACGTCCTGGTCACCCTGTATGAGAGGGATGAGGACAACAACCTTTTG
  » R1-1-9-06_P1  (1)                                             AACCTTCTG
       » p_F1 (2) (1)
         « r1_p2  (1)
         « p_r3   (1)
       » p_F2 (2) (1)
     « Origene3   (1)
                           651                                                      700
                  (651)
     Consensus    (652)  ACTGAGAAGCAGAAGCTGCGGGTGAAGAAGATCCATGAGAATGAGAAGCG
  » NM_003118     (652)  ACTGAGAAGCAGAAGCTGCGGGTGAAGAAGATCCATGAGAATGAGAAGCG
         « p_r1   (•113)
       « p_r1 (2) (•113)
     » Origene5   (652)  ACTGAGAAGCAGAAGCTGCGGGTGAAGAAGATCCATGAGAATGAGAAGCG
        » R1_P1   (652)  ACTGAGAAGCAGAAGCTGCGGGTGAAGAAGATCCATGAGAATGAGAAGCG
        « R2_p2   (583)  ACTGAGAAGCAGAAGCTGCGGGTGAAGAAGATCCATGAGAATGAGAAGCG
         « p_r2   (576)  ACTGAGAAGCAGAAGCTGCGGGTGAAGAAGATCCATGAGAATGAGAAGCG
  » R1-1-9-06_P1  (11)   ACTGAGAAGCAGAAGCTGCGGGTGAAGAAGATCCATGAGAATGAGAAGCG
       » p_F1 (2) (1)                    GCGGGTGAAGAAGATCCATGAGAATGAGAAGCG
         « r1_p2  (1)
         « p_r3   (1)
       » p_F2 (2) (1)
     « Origene3   (1)
                           701                                                      750
                  (701)                  +                         +
     Consensus    (702)  CCTGGAGGCAGGAGACCACCCCGTGGAGCTGCTGGCCCGGGACTTCGAGA
  » NM_003118     (702)  CCTGGAGGCAGGAGACCACCCCGTGGAGCTGCTGGCCCGGGACTTCGAGA
         « p_r1   (•113)
       « p_r1 (2) (•113)
     » Origene5   (702)  CCTGGAGGCA-GAGACCACCCCGTGGAGCTGCTGGCCCCGGACTTCGAGA
        » R1_P1   (702)  CCTGGAGGCAGGAGACCACCCCGTGGAGCTGCTGGCCCGGGACTTCGAGA
        « R2_p2   (633)  CCTGGAGGCAGGAGACCACCCCGTGGAGCTGCTGGCCCGGGACTTCGAGA
         « p_r2   (626)  CCTGGAGGCAGGAGACCACCCCGTGGAGCTGCTGGCCCGGGACTTCGAGA
  » R1-1-9-06_P1  (61)   CCTGGAGGCAGGAGACCACCCCGTGGAGCTGCTGGCCCGGGACTTCGAGA
       » p_F1 (2) (35)   CCTGGAGGCAGGAGACCACCCCGTGGAGCTGCTGGCCCGGGACTTCGAGA
         « r1_p2  (1)
         « p_r3   (1)
       » p_F2 (2) (1)
     « Origene3   (1)
```

Fig. 4F

```
                    751                                                    800
            (751)    +                  ++
  Consensus  (752)  AGAACTATAACATGTACATCTTCCCTGTACACTGGCAGTTCGGCCAGCTG
» NM_003118  (752)  AGAACTATAACATGTACATCTTCCCTGTACACTGGCAGTTCGGCCAGCTG
     « p_r1  (•113)
  « p_r1 (2) (•113)
  » Origene5 (752)  AG-ACTATAACATGTACATCCTCCCTGTACACTGGCAGTTCGGCCAGCTG
     » R1_P1  (752)  AGAACTATAACATGTACATCTTCCCTGTACACTGGCAGTTCGGCCAGCTG
     « R2_p2  (683)  AGAACTATAACATGTACATTTTCCCTGTACACTGGCAGTTCGGCCAGCTG
      « p_r2  (676)  AGAACTATAACATGTACATTTTCCCTGTACACTGGCAGTTCGGCCAGCTG
»R1-1-9-06_P1 (111)  AGAACTATAACATGTACATCTTCCCTGTACACTGGCAGTTCGGCCAGCTG
   » p_F1 (2)  (85)  AGAACTATAACATGTACATCTTCCCTGTACACTGGCAGTTCGGCCAGCTG
     « r1_p2   (1)
      « p_r3   (1)
   » p_F2 (2)  (1)
  « Origene3   (1)

801                                                    850
            (801)                          +                               +
  Consensus  (802)  GACCAGCACCCCATTGACGGGTACCTCTCCCACACCGAGCTGGCTCCACT
» NM_003118  (802)  GACCAGCACCCCATTGACGGGTACCTCTCCCACACCGAGCTGGCTCCACT
     « p_r1  (•113)
  « p_r1 (2) (•113)
  » Origene5 (802)  GACCAGCACCCCATTGACGGGTACCTCTCCCACACCGAGCTGGCTCCA-T
     » R1_P1  (802)  GACCAGCACCCCATTGACGGGTACCTCTCCCACACCGAGCTGGCTCCACT
     « R2_p2  (733)  GACCAGCACCCCATTGACGGGTACCTCTCCCACACCGAGCTGGCTCCACT
      « p_r2  (726)  GACCAGCACCCCATTGACGGGTACCTTTCCCACACCGAGCTGGCTCCACT
»R1-1-9-06_P1 (161)  GACCAGCACCCCATTGACGGGTACCTCTCCCACACCGAGCTGGCTCCACT
   » p_F1 (2) (135)  GACCAGCACCCCATTGACGGGTACCTCTCCCACACCGAGCTGGCTCCACT
     « r1_p2   (1)
      « p_r3   (1)
   » p_F2 (2)  (1)
  « Origene3   (1)

851                                                    900
            (851)                      +            ..
  Consensus  (852)  GCGTGCTCCCCTCATCCCCATGGAGCATTGCACCACCCGCTTTTTCGAGA
» NM_003118  (852)  GCGTGCTCCCCTCATCCCCATGGAGCATTGCACCACCCGCTTTTTCGAGA
     « p_r1  (•113)
  « p_r1 (2) (•113)
  » Origene5 (852)  GCGTGCTCCCCTCAT-CCCATGGAGCAT
     » R1_P1  (852)  GCGTGCTCCCCTCATCCCCATGGNNCATTGCACCACCCGCTTTTTCGAGA
     « R2_p2  (783)  GCGTGCTCCCCTCATCCCCATGGAGCATTGCACCACCCGCTTTTTCGAGA
      « p_r2  (776)  GCGTGCTCCCCTCATCCCCATGGAGCATTGCACCACCCGCTTTTTCGAGA
»R1-1-9-06_P1 (211)  GCGTGCTCCCCTCATCCCCATGGAGCATTGCACCACCCGCTTTTTCGAGA
   » p_F1 (2) (185)  GCGTGCTCCCCTCATCCCCATGGAGCATTGCACCACCCGCTTTTTCGAGA
     « r1_p2   (1)
      « p_r3   (1)
   » p_F2 (2)  (1)
  « Origene3   (1)
```

Fig. 4G

```
                     901                                                    950
              (901)
 Consensus    (902)  CCTGTGACCTGGACAATGACAAGTACATCGCCCTGGATGAGTGGGCCGGC
» NM_003118   (902)  CCTGTGACCTGGACAATGACAAGTACATCGCCCTGGATGAGTGGGCCGGC
    « p_r1    (•113)
    « p_r1 (2)(•113)
  » Origene5  (•878)
    » R1_P1   (902)  CCTGTGACCT
    « R2_p2   (833)  CCTGTGACCTGGACAATGACAAGTACATCGCCCTGGATGAGTGGGCCGGC
    « p_r2    (826)  CCTGTGACCTGGACAATGACAAGTACATCGCCCTGGATGAGTGGGCCGGC
» R1-1-9-06_P1(261)  CCTGTGACCTGGACAATGACAAGTACATCGCCCTGGATGAGTGGGCCGGC
    » p_F1 (2)(235)  CCTGTGACCTGGACAATGACAAGTACATCGCCCTGGATGAGTGGGCCGGC
    « r1_p2   (1)
    « p_r3    (1)
    » p_F2 (2)(1)
    « Origene3(1)
                     951                                                   1000
              (951)                                                           +
 Consensus    (952)  TGCTTCGGCATCAAGCAGAAGGATATCGACAAGGATCTTGTGATCTAAAT
» NM_003118   (952)  TGCTTCGGCATCAAGCAGAAGGATATCGACAAGGATCTTGTGATCTAAAT
    « p_r1    (•113)
    « p_r1 (2)(•113)
  » Origene5  (•878)
    » R1_P1   (•910)
    « R2_p2   (883)  TGCTTCGGCATCAAGCAGAAGGATATCGACAAGGATCTTGTGATTTAAAT
    « p_r2    (876)  TGCTTCGGCATCAAGCAGAAGGATATCGACAAGGATCTTGTGATTTAAAT
» R1-1-9-06_P1(311)  TGCTTCGGCATCAAGCAGAAGGATATCGACAAGGATCTTGTGATCTAAAT
    » p_F1 (2)(285)  TGCTTCGGCATCAAGCAGAAGGATATCGACAAGGATCTTGTGATCTAAAT
    « r1_p2   (1)
    « p_r3    (1)
    » p_F2 (2)(1)
    « Origene3(1)
                    1001                                                   1050
             (1001)
 Consensus   (1002)  CCACTCCTTCCACAGTACCGGATTCTCTCTTTAACCCTCCCCTTCGTGTT
» NM_003118  (1002)  CCACTCCTTCCACAGTACCGGATTCTCTCTTTAACCCTCCCCTTCGTGTT
    « p_r1    (•113)
    « p_r1 (2)(•113)
  » Origene5  (•878)
    » R1_P1   (•910)
    « R2_p2   (933)  CCACTCCTTCCACAGTACCGGATTCTCTCTTTAACCCTCCCCTTCGTG
    « p_r2    (926)  CCACTCCTTCCACAGTACCGGA
» R1-1-9-06_P1(361)  CCACTCCTTCCACAGTACCGGATTCTCTCTTTAACCCTCCCCTTCGTGTT
    » p_F1 (2)(335)  CCACTCCTTCCACAGTACCGGATTCTCTCTTTAACCCTCCCCTTCGTGTT
    « r1_p2   (1)
    « p_r3    (1)
    » p_F2 (2)(1)
    « Origene3(1)
```

Fig. 4H

```
                         1051                                                    1100
                (1051)
   Consensus   (1052)   TCCCCCAATGTTTAAAATGTTTGGATGGTTTGTTGTTCTGCCTGGAGACA
» NM_003118    (1052)   TCCCCCAATGTTTAAAATGTTTGGATGGTTTGTTGTTCTGCCTGGAGACA
      « p_r1    (•113)
   « p_r1 (2)   (•113)
   » Origene5   (•878)
       » R1_P1  (•910)
      « R2_p2   (•979)
       « p_r2   (•946)
» R1-1-9-06_P1   (411)   TCCCCCAATGTTTAAAATGTTTGGATGGTTTGTTGTTCTGCCTGGAGACA
    » p_F1 (2)   (385)   TCCCCCAATGTTTAAAATGTTTGGATGGTTTGTTGTTCTGCCTGGAGACA
      « r1_p2      (1)
       « p_r3      (1)
     » p_F2 (2)    (1)
   « Origene3     (1)

1101                                                    1150
                (1101)
   Consensus   (1102)   AGGTGCTAACATAGATTTAAGTGAATACATTAACGGTGCTAAAAATGAAA
» NM_003118    (1102)   AGGTGCTAACATAGATTTAAGTGAATACATTAACGGTGCTAAAAATGAAA
      « p_r1    (•113)
   « p_r1 (2)   (•113)
   » Origene5   (•878)
       » R1_P1  (•910)
      « R2_p2   (•979)
       « p_r2   (•946)
» R1-1-9-06_P1   (461)   AGGTGCTAACATAGATTTAAGTGAATACATTAACGGTGCTAAAAATGAAA
    » p_F1 (2)   (435)   AGGTGCTAACATAGATTTAAGTGAATACATTAACGGTGCTAAAAATGAAA
      « r1_p2      (1)
       « p_r3      (1)
     » p_F2 (2)    (1)
   « Origene3     (1)

1151                                                    1200
                (1151)
   Consensus   (1152)   ATTCTAACCCAAGACATGACATTCTTAGCTGTAACTTAACTATTAAGGCC
» NM_003118    (1152)   ATTCTAACCCAAGACATGACATTCTTAGCTGTAACTTAACTATTAAGGCC
      « p_r1    (•113)
   « p_r1 (2)   (•113)
   » Origene5   (•878)
       » R1_P1  (•910)
      « R2_p2   (•979)
       « p_r2   (•946)
» R1-1-9-06_P1   (511)   ATTCTAACCCAAGACATGACATTCTTAGCTGTAACTTAACTATTAAGGCC
    » p_F1 (2)   (485)   ATTCTAACCCAAGACATGACATTCTTAGCTGTAACTTAACTATTAAGGCC
      « r1_p2      (1)
       « p_r3      (1)
     » p_F2 (2)    (1)
   « Origene3     (1)
```

Fig. 4I

```
                              1201                                              1250
                       (1201)
        Consensus     (1202)  TTTTCCACACGCATTAATAGTCCCATTTTTCTCTTGCCATTTGTAGCTTT
     » NM_003118      (1202)  TTTTCCACACGCATTAATAGTCCCATTTTTCTCTTGCCATTTGTAGCTTT
           « p_r1     (•113)
         « p_r1 (2)   (•113)
         » Origene5   (•878)
             » R1_P1  (•910)
             « R2_p2  (•979)
               « p_r2 (•946)
     » R1-1-9-06_P1    (561)  TTTTCCACACGCATTAATAGTCCCATTTTTCTCTTGCCATTTGTAGCTTT
           » p_F1 (2)  (535)  TTTTCCACACGCATTAATAGTCCCATTTTTCTCTTGCCATTTGTAGCTTT
              « r1_p2   (1)
              « p_r3    (1)
            » p_F2 (2)  (1)
           « Origene3   (1)

1251                                              1300
                       (1251)
        Consensus     (1252)  GCCCATTGTCTTATTGGCACATGGGTGGACACGGATCTGCTGGGCTCTGC
     » NM_003118      (1252)  GCCCATTGTCTTATTGGCACATGGGTGGACACGGATCTGCTGGGCTCTGC
           « p_r1     (•113)
         « p_r1 (2)   (•113)
         » Origene5   (•878)
             » R1_P1  (•910)
             « R2_p2  (•979)
               « p_r2 (•946)
     » R1-1-9-06_P1    (611)  GCCCATTGTCTTATTGGCACATGGGTGGACACGGATCTGCTGGGCTCTGC
           » p_F1 (2)  (585)  GCCCATTGTCTTATTGGCACATGGGTGGACACGGATCTGCTGGGCTCTGC
              « r1_p2   (1)           TGGCACANGGGTGGACACGGATCTGCTGGGNTCTGC
              « p_r3    (1)
            » p_F2 (2)  (1)
           « Origene3   (1)

1301                          +                   1350
                       (1301)
        Consensus     (1302)  CTTAAACACACATTGCAGCTTCAACTTTTCTCTTTAGTGTTCTGTTTGAA
     » NM_003118      (1302)  CTTAAACACACATTGCAGCTTCAACTTTTCTCTTTAGTGTTCTGTTTGAA
           « p_r1     (•113)
         « p_r1 (2)   (•113)
         » Origene5   (•878)
             » R1_P1  (•910)
             « R2_p2  (•979)
               « p_r2 (•946)
     » R1-1-9-06_P1    (661)  CTTAAACACACATTGCAGCTTCAACTTTTCTCTTTAGTGTTCTGTTTGAA
           » p_F1 (2)  (635)  CTTAAACACACATTGCAGCTTCAACTTTTCTCTTTAGTGTTCTGTTTGAA
              « r1_p2  (38)   CTTAAACNCACATTGCAG-NTCAACTTTTCTCTTTAGTGTTCTGTTTGAA
              « p_r3    (1)                                              GTTTGAA
            » p_F2 (2)  (1)
           « Origene3   (1)
```

Fig. 4J

```
                        1351                                              1400
                  (1351)                                                    +
    Consensus     (1352) ACTAATACTTACCGAGTCAGACTTTGTGTTCATTTCATTTCAGGGTCTTG
 » NM_003118      (1352) ACTAATACTTACCGAGTCAGACTTTGTGTTCATTTCATTTCAGGGTCTTG
       « p_r1     (•113)
    « p_r1 (2)    (•113)
    » Origene5    (•878)
        » R1_P1   (•910)
       « R2_p2    (•979)
        « p_r2    (•946)
» R1-1-9-06_P1    (711)  ACTAATACTTACCGAGTCAGACTTTGTGTTCATTTCATTTCAGGGTCTTG
    » p_F1 (2)    (685)  ACTAATACTTACCGAGTCAGACTTTGTGTTCATTTCATTTCAGGGTCTTG
       « r1_p2    (88)   ACTAATACTTACCGAGTCAGACTTTGTGTTCATTTCATTTCAGGGTCTTG
        « p_r3    (9)    ACTAATACTTACNNAGTCAGACTTTGTGTTCATTTCATTTCAGGGTCTGG
    » p_F2 (2)    (1)
    « Origene3    (1)
                        1401                                              1450
                  (1401)
    Consensus     (1402) GCTGCCTGTGGGCTTCCCCAGGTGGCCTGGAGGTGGGCAAAGGGAAGTAA
 » NM_003118      (1402) GCTGCCTGTGGGCTTCCCCAGGTGGCCTGGAGGTGGGCAAAGGGAAGTAA
       « p_r1     (•113)
    « p_r1 (2)    (•113)
    » Origene5    (•878)
        » R1_P1   (•910)
       « R2_p2    (•979)
        « p_r2    (•946)
» R1-1-9-06_P1    (761)  GCTGCCTGTGGGCTTCCCCAGGTGGCCTGGAGGTGGGCAAAGGNAAGTAA
    » p_F1 (2)    (735)  GCTGCCTGTGGGCTTCCCCAGGTGGCCTGGAGGTGGGCAAAGGGAAGTAA
       « r1_p2    (138)  GCTGCCTGTGGGCTTCCCCAGGTGGCCTGGAGGTGGGCAAAGGGAAGTAA
        « p_r3    (59)   GCTGCCTGTGGGCTTCCCCAGGTGGCCTGGAGGTGGGCAAAGGGAAGTAA
    » p_F2 (2)    (1)
    « Origene3    (1)
                        1451                                              1500
                  (1451)          +·      +                                 .
    Consensus     (1452) CAGACACACGATGTTGTCAAGGATGGTTTTGGGACTAGAGGCTCAGTGGT
 » NM_003118      (1452) CAGACACACGATGTTGTCAAGGATGGTTTTGGGACTAGAGGCTCAGTGGT
       « p_r1     (•113)
    « p_r1 (2)    (•113)
    » Origene5    (•878)
        » R1_P1   (•910)
       « R2_p2    (•979)
        « p_r2    (•946)
» R1-1-9-06_P1    (811)  CAGACACACGATGTTGTCAANGATGG-TTTGGGACTAGAGGCTC
    » p_F1 (2)    (785)  CAGACACACGATGTTGTCAGGGATGGTTTTGGGACTAGAGGCTCAGTGGN
       « r1_p2    (188)  CAGACACACGATGTTGTCAAGGATGGTTTTGGGACTAGAGGCTCAGTGGT
        « p_r3    (109)  CAGACACACGATGTTGTCAAGGATGGTTTTGGGACTAGAGGCTCAGTGGT
    » p_F2 (2)    (1)
    « Origene3    (1)
```

Fig. 4K

```
                        1501                                            1550
                (1501)         .. .. +             +              +
   Consensus    (1502) GGGAGAGATCCCTGCAGAACCCACCAACCAGAACGTGGTTTGCCTGAGGC
 » NM_003118    (1502) GGGAGAGATCCCTGCAGAACCCACCAACCAGAACGTGGTTTGCCTGAGGC
      « p_r1    (•113)
    « p_r1 (2)  (•113)
    » Origene5  (•878)
      » R1_P1   (•910)
      « R2_p2   (•979)
       « p_r2   (•946)
» R1-1-9-06_P1  (•853)
    » p_F1 (2)   (835) GGGAGAGATCNCTGCAGAANNCNNCAACCAGAACGTGGTTTGCCTGA-GN
       « r1_p2   (238) GGGAGAGATCCCTGCAGAACCCACCCACCAGAACGTGGTTTGCCTGAGGC
        « p_r3   (159) GGGAGAGATCCCTGCAGAACCCACCAACCAGAACGT-GTTTGCCTGAGGC
    » p_F2 (2)     (1)
    « Origene3    (1)

1551                                            1600
                (1551)          •++            +
   Consensus    (1552) TGTAACTGAGAGAAAGATTCTGGGGCTGTGTTATGAAAATATAGACATTC
 » NM_003118    (1552) TGTAACTGAGAGAAAGATTCTGGGGCTGTGTTATGAAAATATAGACATTC
      « p_r1    (•113)
    « p_r1 (2)  (•113)
    » Origene5  (•878)
      » R1_P1   (•910)
      « R2_p2   (•979)
       « p_r2   (•946)
» R1-1-9-06_P1  (•853)
    » p_F1 (2)   (885) TGTAACTGAGAGAANATTTCTGGGGCTGTG-TATGAAAATATAGACNTTC
       « r1_p2   (288) TGTAACTGAGAGAAAGATTCTGGGGCTGTGTTATGAAAATATAGACATTC
        « p_r3   (209) TGTAACTGAGAGAAAGATTCTGGGGCTGTGTTATGAAAATATAGACATTC
    » p_F2 (2)     (1)
    « Origene3    (1)

1601                                            1650
                (1601)
   Consensus    (1602) TCACATAAGCCCAGTTCATCACCATTTCCTCCTTTACCTTTCAGTGCAGT
 » NM_003118    (1602) TCACATAAGCCCAGTTCATCACCATTTCCTCCTTTACCTTTCAGTGCAGT
      « p_r1    (•113)
    « p_r1 (2)  (•113)
    » Origene5  (•878)
      » R1_P1   (•910)
      « R2_p2   (•979)
       « p_r2   (•946)
» R1-1-9-06_P1  (•853)
    » p_F1 (2)   (935) TCACATAAGCCCA
       « r1_p2   (338) TCACATAAGCCCAGTTCATCACCATTTCCTCCTTTACCTTTCAGTGCAGT
        « p_r3   (259) TCACATAAGCCCAGTTCATCACCATTTCCTCCTTTACCTTTCAGTGCAGT
    » p_F2 (2)     (1)
    « Origene3    (1)
```

Fig. 4L

```
                          1651                                                    1700
                 (1651)
   Consensus     (1652)   TTCTTTTCACATTAGGCTGTTGGTTCAAACTTTTGGGAGCACGGACTGTC
 » NM_003118     (1652)   TTCTTTTCACATTAGGCTGTTGGTTCAAACTTTTGGGAGCACGGACTGTC
      « p_r1     (•113)
    « p_r1 (2)   (•113)
    » Origene5   (•878)
       » R1_P1   (•910)
       « R2_p2   (•979)
        « p_r2   (•946)
» R1-1-9-06_P1   (•853)
     » p_F1 (2)  (•946)
       « r1_p2   (388)    TTCTTTTCACATTAGGCTGTTGGTTCAAACTTTTGGGAGCACGGACTGTC
        « p_r3   (309)    TTCTTTTCACATTAGGCTGTTGGTTCAAACTTTTGGGAGCACGGACTGTC
     » p_F2 (2)  (1)
     « Origene3  (1)

1701                                                    1750
                 (1701)
   Consensus     (1702)   AGTTCTCTGGGAAGTGGTCAGCGCATCCTGCAGGGCTTCTCCTCCTCTGT
 » NM_003118     (1702)   AGTTCTCTGGGAAGTGGTCAGCGCATCCTGCAGGGCTTCTCCTCCTCTGT
      « p_r1     (•113)
    « p_r1 (2)   (•113)
    » Origene5   (•878)
       » R1_P1   (•910)
       « R2_p2   (•979)
        « p_r2   (•946)
» R1-1-9-06_P1   (•853)
     » p_F1 (2)  (•946)
       « r1_p2   (438)    AGTTCTCTGGGAAGTGGTCAGCGCATCCTGCAGGGCTTCTCCTCCTCTGT
        « p_r3   (359)    AGTTCTCTGGGAAGTGGTCAGCGCATCCTGCAGGGCTTCTCCTCCTCTGT
     » p_F2 (2)  (1)
     « Origene3  (1)

1751                                                    1800
                 (1751)
   Consensus     (1752)   CTTTTGGAGAACCAGGGCTCTTCTCAGGGGCTCTAGGGACTGCCAGGCTG
 » NM_003118     (1752)   CTTTTGGAGAACCAGGGCTCTTCTCAGGGGCTCTAGGGACTGCCAGGCTG
      « p_r1     (•113)
    « p_r1 (2)   (•113)
    » Origene5   (•878)
       » R1_P1   (•910)
       « R2_p2   (•979)
        « p_r2   (•946)
» R1-1-9-06_P1   (•853)
     » p_F1 (2)  (•946)
       « r1_p2   (488)    CTTTTGGAGAACCAGGGCTCTTCTCAGGGGCTCTAGGGACTGCCAGGCTG
        « p_r3   (409)    CTTTTGGAGAACCAGGGCTCTTCTCAGGGGCTCTAGGGACTGCCAGGCTG
     » p_F2 (2)  (1)
     « Origene3  (1)
```

Fig. 4M

```
                        1801                                               1850
              (1801)
Consensus     (1802)    TTTCAGCCAGGAAGGCCAAAATCAAGAGTGAGATGTAGAAAGTTGTAAAA
» NM_003118   (1802)    TTTCAGCCAGGAAGGCCAAAATCAAGAGTGAGATGTAGAAAGTTGTAAAA
«     p_r1    (•113)
«   p_r1 (2)  (•113)
»   Origene5  (•878)
»     R1_P1   (•910)
«     R2_p2   (•979)
«     p_r2    (•946)
» R1-1-9-06_P1 (•853)
»    p_F1 (2) (•946)
«     r1_p2    (538)    TTTCAGCCAGGAAGGCCAAAATCAAGAGTGAGATGTAGAAAGTTGTAAAA
«     p_r3     (459)    TTTCAGCCAGGAAGGCCAAAATCAAGAGTGAGATGTAGAAAGTTGTAAAA
»    p_F2 (2)    (1)
«    Origene3    (1)

1851                                               1900
              (1851)
Consensus     (1852)    TAGAAAAAGTGGAGTTGGTGAATCGGTTGTTCTTTCCTCACATTTGGATG
» NM_003118   (1852)    TAGAAAAAGTGGAGTTGGTGAATCGGTTGTTCTTTCCTCACATTTGGATG
«     p_r1    (•113)
«   p_r1 (2)  (•113)
»   Origene5  (•878)
»     R1_P1   (•910)
«     R2_p2   (•979)
«     p_r2    (•946)
» R1-1-9-06_P1 (•853)
»    p_F1 (2) (•946)
«     r1_p2    (588)    TAGAAAAAGTGGAGTTGGTGAATCGGTTGTTCTTTCCTCACATTTGGATG
«     p_r3     (509)    TAGAAAAAGTGGAGTTGGTGAATCGGTTGTTCTTTCCTCACATTTGGATG
»    p_F2 (2)    (1)
«    Origene3    (1)

1901                                               1950
              (1901)
Consensus     (1902)    ATTGTCATAAGGTTTTTAGCATGTTCCTCCTTTTCTTCACCCTCCCCTTT
» NM_003118   (1902)    ATTGTCATAAGGTTTTTAGCATGTTCCTCCTTTTCTTCACCCTCCCCTTT
«     p_r1    (•113)
«   p_r1 (2)  (•113)
»   Origene5  (•878)
»     R1_P1   (•910)
«     R2_p2   (•979)
«     p_r2    (•946)
» R1-1-9-06_P1 (•853)
»    p_F1 (2) (•946)
«     r1_p2    (638)    ATTGTCATAAGGTTTTTAGCATGTTCCTCCTTTTCTTCACCCTCCCCTTT
«     p_r3     (559)    ATTGTCATAAGGTTTTTAGCATGTTCCTCCTTTTCTTCACCCTCCCCTTT
»    p_F2 (2)    (1)
«    Origene3    (1)
```

Fig. 4N

```
                       1951                                              2000
              (1951)
Consensus     (1952)   TTTCTTCTATTAATCAAGAGAAACTTCAAAGTTAATGGGATGGTCGGATC
» NM_003118   (1952)   TTTCTTCTATTAATCAAGAGAAACTTCAAAGTTAATGGGATGGTCGGATC
    « p_r1    (•113)
« p_r1 (2)    (•113)
  » Origene5  (•878)
     » R1_P1  (•910)
     « R2_p2  (•979)
      « p_r2  (•946)
» R1-1-9-06_P1 (•853)
  » p_F1 (2)  (•946)
     « r1_p2   (688)   TTTCTTCTATTAATCAAGAGAAACTTCAAAGTTAATGGGATGGTCGGATC
      « p_r3   (609)   TTTCTTCTATTAATCAAGAGAAACTTCAAAGTTAATGGGATGGTCGGATC
  » p_F2 (2)     (1)
  « Origene3     (1)

2001                                              2050
              (2001)
Consensus     (2002)   TCACAGGCTGAGAACTCGTTCACCTCCAAGCATTTCATGAAAAAGCTGCT
» NM_003118   (2002)   TCACAGGCTGAGAACTCGTTCACCTCCAAGCATTTCATGAAAAAGCTGCT
    « p_r1    (•113)
« p_r1 (2)    (•113)
  » Origene5  (•878)
     » R1_P1  (•910)
     « R2_p2  (•979)
      « p_r2  (•946)
» R1-1-9-06_P1 (•853)
  » p_F1 (2)  (•946)
     « r1_p2   (738)   TCACAGGCTGAGAACTCGTTCACCTCCAAGCATTTCATGAAAAAGCTGCT
      « p_r3   (659)   TCACAGGCTGAGAACTCGTTCACCTCCAAGCATTTCATGAAAAAGCTGCT
  » p_F2 (2)     (1)                                                GCTGCT
  « Origene3     (1)

2051                                              2100
              (2051)
Consensus     (2052)   TCTTATTAATCATACAAACTCTCACCATGATGTGAAGAGTTTCACAAATC
» NM_003118   (2052)   TCTTATTAATCATACAAACTCTCACCATGATGTGAAGAGTTTCACAAATC
    « p_r1    (•113)
« p_r1 (2)    (•113)
  » Origene5  (•878)
     » R1_P1  (•910)
     « R2_p2  (•979)
      « p_r2  (•946)
» R1-1-9-06_P1 (•853)
  » p_F1 (2)  (•946)
     « r1_p2   (788)   TCTTATTAATCATACAAACTCTCACCATGATGTGAAGAGTTTCACAAATC
      « p_r3   (709)   TCTTATTAATCATACAAACTCTCACCATGATGTGAAGAGTTTCACAAATC
  » p_F2 (2)     (8)   TCTTATTAATCATACAAACTCTCACCATGATGTGAAGAGTTTCACAAATC
  « Origene3     (1)
```

Fig. 4O

```
                              2101                                              2150
                     (2101)
     Consensus      (2102)   CTTCAAAATAAAAAGTAATGACTTAGAAACTGCCTTCCTGGGTGATTTGC
   » NM_003118      (2102)   CTTCAAAATAAAAAGTAATGACTTAGAAACTGCCTTCCTGGGTGATTTGC
        « p_r1      (•113)
    « p_r1 (2)      (•113)
     » Origene5     (•878)
        » R1_P1     (•910)
        « R2_p2     (•979)
         « p_r2     (•946)
  » R1-1-9-06_P1    (•853)
     » p_F1 (2)     (•946)
        « r1_p2     (838)    CTTCAAAATAAAAAGTAATGACTTAGAAACTGCCTTCCTGGGTGATTTGC
         « p_r3     (759)    CTTCAAAATAAAAAGTAATGACTTAGAAACTGCCTTCCTGGGTGATTTGC
     » p_F2 (2)     (58)     CTTCAAAATAAAAAGTAATGACTTAGAAACTGCCTTCCTGGGTGATTTGC
      « Origene3    (1)

2151                                              2200
                     (2151)
     Consensus      (2152)   ATGTGTCTTAGTCTTAGTCACCTTATTATCCTGACACAAAAACACATGAG
   » NM_003118      (2152)   ATGTGTCTTAGTCTTAGTCACCTTATTATCCTGACACAAAAACACATGAG
        « p_r1      (•113)
    « p_r1 (2)      (•113)
     » Origene5     (•878)
        » R1_P1     (•910)
        « R2_p2     (•979)
         « p_r2     (•946)
  » R1-1-9-06_P1    (•853)
     » p_F1 (2)     (•946)
        « r1_p2     (888)    ATGTGTCTTAGTCTTAGTCACCTTATTATCCTGACACAAAAACACATGAG
         « p_r3     (809)    ATGTGTCTTAGTCTTAGTCACCTTATTATCCTGACACAAAAACACATGAG
     » p_F2 (2)     (108)    ATGTGTCTTAGTCTTAGTCACCTTATTATCCTGACACAAAAACACATGAG
      « Origene3    (1)

2201                                              2250
                     (2201)
     Consensus      (2202)   CATACATGTCTACACATGACTACACAAATGCAAACCTTTGCAAACACATT
   » NM_003118      (2202)   CATACATGTCTACACATGACTACACAAATGCAAACCTTTGCAAACACATT
        « p_r1      (•113)
    « p_r1 (2)      (•113)
     » Origene5     (•878)
        » R1_P1     (•910)
        « R2_p2     (•979)
         « p_r2     (•946)
  » R1-1-9-06_P1    (•853)
     » p_F1 (2)     (•946)
        « r1_p2     (938)    CATACATGTCTACACATGACTACACAAATGCAAACCTTTGCAAACACATT
         « p_r3     (859)    CATACATGTCTACACATGACTACACAAATGCAAACCTTTGCAAACACATT
     » p_F2 (2)     (158)    CATACATGTCTACACATGACTACACAAATGCAAACCTTTGCAAACACATT
      « Origene3    (1)
```

Fig. 4P

```
                            2251                                                  2300
                  (2251)      +                                                     +
      Consensus   (2252)    ATGCTTTTGCACACACACACCTGTACACACACACCGGCATGTTTATACAC
  »  NM_003118    (2252)    ATGCTTTTGCACACACACACCTGTACACACACACCGGCATGTTTATACAC
       «  p_r1    (•113)
     «  p_r1 (2)  (•113)
     »  Origene5  (•878)
         »  R1_P1 (•910)
         «  R2_p2 (•979)
           «  p_r2 (•946)
  » R1-1-9-06_P1  (•853)
       »  p_F1 (2) (•946)
           «  r1_p2 (988)   ATGCTTTTGCACACACACACCTGTACACACACACCGGCA
             «  p_r3 (909)  ATGCTTTTGCACACACACACCTGTACACACACACCGGCAT
       »  p_F2 (2) (208)    ATGCTTTTGCACACACACACCTGTACACACACACCGGCATGTTTATACAC
         «  Origene3   (1)                                            GTTTATACCC 2301                                                  2350
                  (2301)      +    +  +     +           +                           +
      Consensus   (2302)    AGGGAGTGTATGGTTCCTGTAAGCACTAAGTTAGCTGTTTTCATTTAATG
  »  NM_003118    (2302)    AGGGAGTGTATGGTTCCTGTAAGCACTAAGTTAGCTGTTTTCATTTAATG
       «  p_r1    (•113)
     «  p_r1 (2)  (•113)
     »  Origene5  (•878)
         »  R1_P1 (•910)
         «  R2_p2 (•979)
           «  p_r2 (•946)
  » R1-1-9-06_P1  (•853)
       »  p_F1 (2) (•946)
           «  r1_p2 (•1025)
             «  p_r3 (•947)
       »  p_F2 (2) (258)    AGGGAGTGTATGGTTCCTGTAAGCACTAAGTTAGCTGTTTTCATTTAATG
         «  Origene3  (12)  AGGGAGGGTAGGTTTCTTGTAAGCAATAAGTTAGCTGTTTTCATTTAAGG 2351                                                  2400
                  (2351)      +              + ·+    +     +
      Consensus   (2352)    ACCTGTGGTTTAACCCTTTTGATCACTACCACCATTATCAGCACCAGACT
  »  NM_003118    (2352)    ACCTGTGGTTTAACCCTTTTGATCACTACCACCATTATCAGCACCAGACT
       «  p_r1    (•113)
     «  p_r1 (2)  (•113)
     »  Origene5  (•878)
         »  R1_P1 (•910)
         «  R2_p2 (•979)
           «  p_r2 (•946)
  » R1-1-9-06_P1  (•853)
       »  p_F1 (2) (•946)
           «  r1_p2 (•1025)
             «  p_r3 (•947)
       »  p_F2 (2) (308)    ACCTGTGGTTTAACCCTTTTGATCACTACCACCATTATCAGCACCAGACT
         «  Origene3  (62)  ACCTGTGGTTT-ACCCTTTTGATCATNTCCCCCAATATCAGCACCAGANT
```

Fig. 4Q

```
                           2401                                              2450
             (2401)                   +         +
  Consensus  (2402)  GAGCAGCTATATCCTTTTATTAATCATGGTCATTCATTCATTCATTCATT
» NM_003118  (2402)  GAGCAGCTATATCCTTTTATTAATCATGGTCATTCATTCATTCATTCATT
      « p_r1  (•113)
  « p_r1 (2)  (•113)
  » Origene5  (•878)
     » R1_P1  (•910)
     « R2_p2  (•979)
       « p_r2 (•946)
»R1-1-9-06_P1 (•853)
    » p_F1 (2) (•946)
    « r1_p2 (•1025)
       « p_r3 (•947)
    » p_F2 (2)  (358)  GAGCAGCTATATCCTTTTATTAATCATGGTCATTCATTCATTCATTCATT
  « Origene3   (112)  GAGCAGCTATAT-CTTTTATT-ATCATGGTCATTCATTCATTCATTCATT 2451                                              2500
             (2451)
  Consensus  (2452)  CACAAAATATTTATGATGTATTTACTCTGCACCAGGTCCCATGCCAAGCA
» NM_003118  (2452)  CACAAAATATTTATGATGTATTTACTCTGCACCAGGTCCCATGCCAAGCA
      « p_r1  (•113)
  « p_r1 (2)  (•113)
  » Origene5  (•878)
     » R1_P1  (•910)
     « R2_p2  (•979)
       « p_r2 (•946)
»R1-1-9-06_P1 (•853)
    » p_F1 (2) (•946)
    « r1_p2 (•1025)
       « p_r3 (•947)
    » p_F2 (2)  (408)  CACAAAATATTTATGATGTATTTACTCTGCACCAGGTCCCATGCCAAGCA
  « Origene3   (162)  CACAAAATATTTATGATGTATTTACTNTGCACCAGGTCCCATGCCAAGCA
                           2501                                              2550
             (2501)
  Consensus  (2502)  CTGGGGACACAGTTATGGCAAAGTAGACAAAGCATTTGTTCATTTGGAGC
» NM_003118  (2502)  CTGGGGACACAGTTATGGCAAAGTAGACAAAGCATTTGTTCATTTGGAGC
      « p_r1  (•113)
  « p_r1 (2)  (•113)
  » Origene5  (•878)
     » R1_P1  (•910)
     « R2_p2  (•979)
       « p_r2 (•946)
»R1-1-9-06_P1 (•853)
    » p_F1 (2) (•946)
    « r1_p2 (•1025)
       « p_r3 (•947)
    » p_F2 (2)  (458)  CTGGGGACACAGTTATGGCAAAGTAGACAAAGCATTTGTTCATTTGGAGC
  « Origene3   (212)  CTGGGGACACAGTTATGGCAAAGTAGACAAAGCATTTGTTCATTTGGAGC
```

Fig. 4R

```
                          2551                                                  2600
                       (2551)
         Consensus    (2552)  TTAGAGTCCAGGAGGAATACATTAGATAATGACACAATCAAATATAAATT
      » NM_003118     (2552)  TTAGAGTCCAGGAGGAATACATTAGATAATGACACAATCAAATATAAATT
          « p_r1      (•113)
          « p_r1 (2)  (•113)
         » Origene5   (•878)
            » R1_P1   (•910)
            « R2_p2   (•979)
            « p_r2    (•946)
      » R1-1-9-06_P1  (•853)
           » p_F1 (2) (•946)
            « r1_p2   (•1025)
            « p_r3    (•947)
           » p_F2 (2) (508)   TTAGAGTCCAGGAGGAATACATTAGATAATGACACAATCAAATATAAATT
         « Origene3   (262)   TTAGAGTCCAGGAGGAATACATTAGATAATGACACAATCAAATATAAATT 2601                                                  2650
                       (2601)
         Consensus    (2602)  GCAAGATGTCACAGGTGTGATGAAGGGAGAGTAGGAGAGACCATGAGTAT
      » NM_003118     (2602)  GCAAGATGTCACAGGTGTGATGAAGGGAGAGTAGGAGAGACCATGAGTAT
          « p_r1      (•113)
          « p_r1 (2)  (•113)
         » Origene5   (•878)
            » R1_P1   (•910)
            « R2_p2   (•979)
            « p_r2    (•946)
      » R1-1-9-06_P1  (•853)
           » p_F1 (2) (•946)
            « r1_p2   (•1025)
            « p_r3    (•947)
           » p_F2 (2) (558)   GCAAGATGTCACAGGTGTGATGAAGGGAGAGTAGGAGAGACCATGAGTAT
         « Origene3   (312)   GCAAGATGTCACAGGTGTGATGAAGGGAGAGTAGGAGAGACCATGAGTAT
```

Fig. 4S

```
                              2651                                                  2700
                    (2651)
    Consensus       (2652)   GTGTAACAGGAGGACACAGCATTATTCTAGTGCTGTACTGTTCCGTACGG
  » NM_003118       (2652)   GTGTAACAGGAGGACACAGCATTATTCTAGTGCTGTACTGTTCCGTACGG
       « p_r1       (•113)
       « p_r1 (2)   (•113)
     » Origene5     (•878)
        » R1_P1     (•910)
        « R2_p2     (•979)
         « p_r2     (•946)
  » R1-1-9-06_P1    (•853)
        » p_F1 (2)  (•946)
         « r1_p2   (•1025)
           « p_r3   (•947)
        » p_F2 (2)   (608)   GTGTAACAGGAGGACACAGCATTATTCTAGTGCTGTACTGTTCCGTACGG
      « Origene3    (362)   GTGTAACAGGAGGACACAGCATTATTCTAGTGCTGTACTGTTCCGTACGG
                              2701                                                  2750
                    (2701)
    Consensus       (2702)   CAGCCACTACCCACATGTAACTTTTTAAGATTTAAATTTAAATTAGTTAA
  » NM_003118       (2702)   CAGCCACTACCCACATGTAACTTTTTAAGATTTAAATTTAAATTAGTTAA
       « p_r1       (•113)
       « p_r1 (2)   (•113)
     » Origene5     (•878)
        » R1_P1     (•910)
        « R2_p2     (•979)
         « p_r2     (•946)
  » R1-1-9-06_P1    (•853)
        » p_F1 (2)  (•946)
         « r1_p2   (•1025)
           « p_r3   (•947)
        » p_F2 (2)   (658)   CAGCCACTACCCACATGTAACTTTTTAAGATTTAAATTTAAATTAGTTAA
      « Origene3    (412)   CAGCCACTACCCACATGTAACTTTTTAAGATTTAAATTTAAATTAGTTAA
                              2751                                                  2800
                    (2751)
    Consensus       (2752)   CATTCAAAACGCAGCTCCCCAATCACACTAGCAACATTTCAAGTGCTTGA
  » NM_003118       (2752)   CATTCAAAACGCAGCTCCCCAATCACACTAGCAACATTTCAAGTGCTTGA
       « p_r1       (•113)
       « p_r1 (2)   (•113)
     » Origene5     (•878)
        » R1_P1     (•910)
        « R2_p2     (•979)
         « p_r2     (•946)
  » R1-1-9-06_P1    (•853)
        » p_F1 (2)  (•946)
         « r1_p2   (•1025)
           « p_r3   (•947)
        » p_F2 (2)   (708)   CATTCAAAACGCAGCTCCCCAATCACACTAGCAACATTTCAAGTGCTTGA
      « Origene3    (462)   CATTCAAAACGCAGCTCCCCAATCACACTAGCAACATTTCAAGTGCTTGA
```

Fig. 4T

```
                          2801                                                2850
               (2801)
   Consensus   (2802)  GAGCCATGCATGATTAGTGGTTACCCTATTGAATAGGTCAGAAGTAGAAT
 » NM_003118   (2802)  GAGCCATGCATGATTAGTGGTTACCCTATTGAATAGGTCAGAAGTAGAAT
      « p_r1   (•113)
   « p_r1 (2)  (•113)
   » Origene5  (•878)
       » R1_P1 (•910)
       « R2_p2 (•979)
        « p_r2 (•946)
» R1-1-9-06_P1 (•853)
    » p_F1 (2) (•946)
       « r1_p2 (•1025)
        « p_r3 (•947)
    » p_F2 (2)  (758)  GAGCCATGCATGATTAGTGGTTACCCTATTGAATAGGTCAGAAGTAGAAT
    « Origene3  (512)  GAGCCATGCATGATTAGTGGTTACCCTATTGAATAGGTCAGAAGTAGAAT
                          2851                                                2900
               (2851)
   Consensus   (2852)  CTTTTCATCATCACAGAAAGTTCTATTGGACAGTGCTCTTCTAGATCATC
 » NM_003118   (2852)  CTTTTCATCATCACAGAAAGTTCTATTGGACAGTGCTCTTCTAGATCATC
      « p_r1   (•113)
   « p_r1 (2)  (•113)
   » Origene5  (•878)
       » R1_P1 (•910)
       « R2_p2 (•979)
        « p_r2 (•946)
» R1-1-9-06_P1 (•853)
    » p_F1 (2) (•946)
       « r1_p2 (•1025)
        « p_r3 (•947)
    » p_F2 (2)  (808)  CTTTTCATCATCACAGAAAGTTCTATTGGACAGTGCTCTTCTAGATCATC
    « Origene3  (562)  CTTTTCATCATCACAGAAAGTTCTATTGGACAGTGCTCTTCTAGATCATC
                          2901                                                2950
               (2901)
   Consensus   (2902)  ATAAGACTACAGAGCACTTTTCAAAGCTCATGCATGTTCATCATGTTAGT
 » NM_003118   (2902)  ATAAGACTACAGAGCACTTTTCAAAGCTCATGCATGTTCATCATGTTAGT
      « p_r1   (•113)
   « p_r1 (2)  (•113)
   » Origene5  (•878)
       » R1_P1 (•910)
       « R2_p2 (•979)
        « p_r2 (•946)
» R1-1-9-06_P1 (•853)
    » p_F1 (2) (•946)
       « r1_p2 (•1025)
        « p_r3 (•947)
    » p_F2 (2)  (858)  ATAAGACTACAGAGCACTTTTCAAAGCTCATGCATGTTCNTCATGTTAGT
    « Origene3  (612)  ATAAGACTACAGAGCACTTTTCAAAGCTCATGCATGTTCATCATGTTAGT
```

Fig. 4U

```
                              2951
                     (2951)
       Consensus    (2952)   GTCGTATTT
    »  NM_003118    (2952)   GTCGTATTT
    «       p_r1    (•113)
    «    p_r1 (2)   (•113)
    »    Origene5   (•878)
    »       R1_P1   (•910)
    «       R2_p2   (•979)
    «        p_r2   (•946)
    »  R1-1-9-06_P1 (•853)
    »     p_F1 (2)  (•946)
    «        r1_p2  (•1025)
    «         p_r3  (•947)
    »     p_F2 (2)   (908)   GTCGTATTT
    «      Origene3  (662)   GTCGTATTT
```

Fig. 5

```
CTCCACATTCCCGCGGTCCTTCAGACTGCCCGGAGAGCGCGCTCTGCCTGCCGCCTGCCTGCCTGCCACTGAGGG
TTCCCAGCACCATGAGGGCCTGGATCTTCTTTCTCCTTTGCCTGGCCGGGAGGGCCTTGGCAGCCCCTCAAGAAG
CCCTGCCTGATGAGACAGAGGTGGTGGAAGAAACTGTGGCAGAGGTGACTGAGGTATCTGTGGGAGCTAATCCTG
TCCAGGTGGAAGTAGGAGAATTTGATGATGGTGCAGAGGAAACCGAAGAGGAGGTGGTGGCGGAAAATCCCTGCC
AGAACCACCACTGCAAACACGGCAAGGTGTGCGAGCTGGATGAGAACAACACCCCCATGTGCGTGTGCCAGGACC
CCACCAGCTGCCCAGCCCCCATTGGCGAGTTTGAGAAGGTGTGCAGCAATGACAACAAGACCTTCGACTCTTCCT
GCCACTTCTTTGCCACAAAGTGCACCCTGGAGGGCACCAAGAAGGGCACAAGCTCCACCTGGACTACATCGGGC
CTTGCAAATACATCCCCCCTTGCCTGGACTCTGAGCTGACCGAATTCCCCCTGCGCATGCGGGACTGGCTCAAGA
ACGTCCTGGTCACCCTGTATGAGAGGGATGAGGACAACAACCTTCTGACTGAGAAGCAGAAGCTGCGGGTGAAGA
AGATCCATGAGAATGAGAAGCGCCTGGAGGCAGGAGACCACCCCGTGGAGCTGCTGGCCCGGGACTTCGAGAAGA
ACTATAACATGTACATCTTCCCTGTACACTGGCAGTTCGGCCAGCTGGACCAGCACCCCATTGACGGGTACCTCT
CCCACACCGAGCTGGCTCCACTGCGTGCTCCCCTCATCCCCATGGAGCATTGCACCACCCGCTTTTTCGAGACCT
GTGACCTGGACAATGACAAGTACATCGCCCTGGATGAGTGGGCCGGCTGCTTCGGCATCAAGCAGAAGGATATCG
ACAAGGATCTTGTGATCTAAATCCACTCCTTCCACAGTACCGGATTCTCTCTTTAACCCTCCCCTTCGTGTTTCC
CCCAATGTTTAAAATGTTTGGATGGTTTGTTGTTCTGCCTGGAGACAAGGTGCTAACATAGATTTAAGTGAATAC
ATTAACGGTGCTAAAAATGAAAATTCTAACCCAAGACATGACATTCTTAGCTGTAACTTAACTATTAAGGCCTTT
TCCACACGCATTAATAGTCCCATTTTTCTCTTGCCATTTGTAGCTTTGCCCATTGTCTTATTGGCACATGGGTGG
ACACGGATCTGCTGGGCTCTGCCTTAAACACACATTGCAGCTTCAACTTTTCTCTTTAGTGTTCTGTTTGAAACT
AATACTTACCGAGTCAGACTTTGTGTTCATTTCATTTCAGGGTCTTGGCTGCCTGTGGGCTTCCCCAGGTGGCCT
GGAGGTGGGCAAAGGGAAGTAACAGACACACGATGTTGTCAAGGATGGTTTTGGGACTAGAGGCTCAGTGGTGGG
AGAGATCCCTGCAGAACCCACCAACCAGAACGTGGTTTGCCTGAGGCTGTAACTGAGAGAAAGATTCTGGGGCTG
TGTTATGAAAATATAGACATTCTCACATAAGCCCAGTTCATCACCATTTCCTCCTTTACCTTTCAGTGCAGTTTC
TTTTCACATTAGGCTGTTGGTTCAAACTTTTGGGAGCACGGACTGTCAGTTCTCTGGGAAGTGGTCAGCGCATCC
TGCAGGGCTTCTCCTCCTCTGTCTTTTGGAGAACCAGGGCTCTTCTCAGGGGCTCTAGGGACTGCCAGGCTGTTT
CAGCCAGGAAGGCCAAAATCAAGAGTGAGATGTAGAAAGTTGTAAAATAGAAAAAGTGGAGTTGGTGAATCGGTT
GTTCTTTCCTCACATTTGGATGATTGTCATAAGGTTTTTAGCATGTTCCTCCTTTTCTTCACCCTCCCCTTTTTT
CTTCTATTAATCAAGAGAAACTTCAAAGTTAATGGGATGGTCGGATCTCACAGGCTGAGAACTCGTTCACCTCCA
AGCATTTCATGAAAAGCTGCTTCTTATTAATCATACAAACTCTCACCATGATGTGAAGAGTTTCACAAATCCTT
CAAAATAAAAAGTAATGACTTAGAAACTGCCTTCCTGGGTGATTTGCATGTGTCTTAGTCTTAGTCACCTTATTA
TCCTGACACAAAAACACATGAGCATACATGTCTACACATGACTACACAAATGCAAACCTTTGCAAACACATTATG
CTTTTGCACACACACACCTGTACACACACACCGGCATGTTTATACACAGGGAGTGTATGGTTCCTGTAAGCACTA
AGTTAGCTGTTTTCATTTAATGACCTGTGGTTTAACCCTTTTGATCACTACCACCATTATCAGCACCAGACTGAG
CAGCTATATCCTTTTATTAATCATGGTCATTCATTCATTCATTCATTCACAAAATATTTATGATGTATTTACTCT
GCACCAGGTCCCATGCCAAGCACTGGGACACAGTTATGGCAAAGTAGACAAAGCATTTGTTCATTTGGAGCTTA
GAGTCCAGGAGGAATACATTAGATAATGACACAATCAAATATAAATTGCAAGATGTCACAGGTGTGATGAAGGGA
GAGTAGGAGAGACCATGAGTATGTGTAACAGGAGGACACAGCATTATTCTAGTGCTGTACTGTTCCGTACGGCAG
CCACTACCCACATGTAACTTTTTAAGATTTAAATTTAAATTAGTTAACATTCAAAACGCAGCTCCCAATCACAC
TAGCAACATTTCAAGTGCTTGAGAGCCATGCATGATTAGTGGTTACCCTATTGAATAGGTCAGAAGTAGAATCTT
TTCATCATCACAGAAAGTTCTATTGGACAGTGCTCTTCTAGATCATCATAAGACTACAGAGCACTTTTCAAAGCT
CATGCATGTTCATCATGTTAGTGTCGTATTT
```

Fig. 6

```
NO: 4    1   M   R   A   W   I   F   F   L   L   C   L   A   G   R   A   L   A   A   P   Q
NO: 5    1   ATGAGGGCCTGGATCTTCTTTCTCCTTTGCCTGGCCGGGAGGGCCTTGGCAGCCCCTCAA

21   E   A   L   P   D   E   T   E   V   V   E   E   T   V   A   E   V   T   E   V
        61   GAAGCCCTGCCTGATGAGACAGAGGTGGTGGAAGAAACTGTGGCAGAGGTGACTGAGGTA

41   S   V   G   A   N   P   V   Q   V   E   V   G   E   F   D   D   G   A   E   E
       121   TCTGTGGGAGCTAATCCTGTCCAGGTGGAAGTAGGAGAATTTGATGATGGTGCAGAGGAA

61   T   E   E   E   V   V   A   E   N   P   C   Q   N   H   H   C   K   H   G   K
       181   ACCGAAGAGGAGGTGGTGGCGGAAAATCCCTGCCAGAACCACCACTGCAAACACGGCAAG

81   V   C   E   L   D   E   N   N   T   P   M   C   V   C   Q   D   P   T   S   C
       241   GTGTGCGAGCTGGATGAGAACAACACCCCCATGTGCGTGTGCCAGGACCCCACCAGCTGC

101   P   A   P   I   G   E   F   E   K   V   C   S   N   D   N   K   T   F   D   S
       301   CCAGCCCCCATTGGCGAGTTTGAGAAGGTGTGCAGCAATGACAACAAGACCTTCGACTCT

121   S   C   H   F   F   A   T   K   C   T   L   E   G   T   K   K   G   H   K   L
       361   TCCTGCCACTTCTTTGCCACAAAGTGCACCCTGGAGGGCACCAAGAAGGGCCACAAGCTC

141   H   L   D   Y   I   G   P   C   K   Y   I   P   P   C   L   D   S   E   L   T
       421   CACCTGGACTACATCGGGCCTTGCAAATACATCCCCCCTTGCCTGGACTCTGAGCTGACC

161   E   F   P   L   R   M   R   D   W   L   K   N   V   L   V   T   L   Y   E   R
       481   GAATTCCCCCTGCGCATGCGGGACTGGCTCAAGAACGTCCTGGTCACCCTGTATGAGAGG

181   D   E   D   N   N   L   L   T   E   K   Q   K   L   R   V   K   K   I   H   E
       541   GATGAGGACAACAACCTTCTGACTGAGAAGCAGAAGCTGCGGGTGAAGAAGATCCATGAG

201   N   E   K   R   L   E   A   G   D   H   P   V   E   L   L   A   R   D   F   E
       601   AATGAGAAGCGCCTGGAGGCAGGAGACCACCCCGTGGAGCTGCTGGCCCGGGACTTCGAG

221   K   N   Y   N   M   Y   I   F   P   V   H   W   Q   F   G   Q   L   D   Q   H
       661   AAGAACTATAACATGTACATCTTCCCTGTACACTGGCAGTTCGGCCAGCTGGACCAGCAC

241   P   I   D   G   Y   L   S   H   T   E   L   A   P   L   R   A   P   L   I   P
       721   CCCATTGACGGGTACCTCTCCCACACCGAGCTGGCTCCACTGCGTGCTCCCCTCATCCCC

261   M   E   H   C   T   T   R   F   F   E   T   C   D   L   D   N   D   K   Y   I
       781   ATGGAGCATTGCACCACCCGCTTTTTCGAGACCTGTGACCTGGACAATGACAAGTACATC

281   A   L   D   E   W   A   G   C   F   G   I   K   Q   K   D   I   D   K   D   L
       841   GCCCTGGATGAGTGGGCCGGCTGCTTCGGCATCAAGCAGAAGGATATCGACAAGGATCTT

301   V   I   *
       901   GTGATCTAA
```

*: stop codon

Fig. 7

```
NO: 2    1   A  P  Q  E  A  L  P  D  E  T  E  V  V  E  E  T  V  A  E  V
NO: 6    1   GCCCCTCAAGAAGCCCTGCCTGATGAGACAGAGGTGGTGGAAGAAACTGTGGCAGAGGTG

21  T  E  V  S  V  G  A  N  P  V  Q  V  E  V  G  E  F  D  D  G
         61  ACTGAGGTATCTGTGGGAGCTAATCCTGTCCAGGTGGAAGTAGGAGAATTTGATGATGGT

41  A  E  E  T  E  E  E  V  V  A  E  N  P  C  Q  N  H  H  C  K
        121  GCAGAGGAAACCGAAGAGGAGGTGGTGGCGGAAAATCCCTGCCAGAACCACCACTGCAAA

61  H  G  K  V  C  E  L  D  E  N  N  T  P  M  C  V  C  Q  D  P
        181  CACGGCAAGGTGTGCGAGCTGGATGAGAACAACACCCCCATGTGCGTGTGCCAGGACCCC

81  T  S  C  P  A  P  I  G  E  F  E  K  V  C  S  N  D  N  K  T
        241  ACCAGCTGCCCAGCCCCCATTGGCGAGTTTGAGAAGGTGTGCAGCAATGACAACAAGACC

101  F  D  S  S  C  H  F  F  A  T  K  C  T  L  E  G  T  K  K  G
        301  TTCGACTCTTCCTGCCACTTCTTTGCCACAAAGTGCACCCTGGAGGGCACCAAGAAGGGC

121  H  K  L  H  L  D  Y  I  G  P  C  K  Y  I  P  P  C  L  D  S
        361  CACAAGCTCCACCTGGACTACATCGGGCCTTGCAAATACATCCCCCCTTGCCTGGACTCT

141  E  L  T  E  F  P  L  R  M  R  D  W  L  K  N  V  L  V  T  L
        421  GAGCTGACCGAATTCCCCCTGCGCATGCGGGACTGGCTCAAGAACGTCCTGGTCACCCTG

161  Y  E  R  D  E  D  N  N  L  L  T  E  K  Q  K  L  R  V  K  K
        481  TATGAGAGGGATGAGGACAACAACCTTCTGACTGAGAAGCAGAAGCTGCGGGTGAAGAAG

181  I  H  E  N  E  K  R  L  E  A  G  D  H  P  V  E  L  L  A  R
        541  ATCCATGAGAATGAGAAGCGCCTGGAGGCAGGAGACCACCCCGTGGAGCTGCTGGCCCGG

201  D  F  E  K  N  Y  N  M  Y  I  F  P  V  H  W  Q  F  G  Q  L
        601  GACTTCGAGAAGAACTATAACATGTACATCTTCCCTGTACACTGGCAGTTCGGCCAGCTG

221  D  Q  H  P  I  D  G  Y  L  S  H  T  E  L  A  P  L  R  A  P
        661  GACCAGCACCCCATTGACGGGTACCTCTCCCACACCGAGCTGGCTCCACTGCGTGCTCCC

241  L  I  P  M  E  H  C  T  T  R  F  F  E  T  C  D  L  D  N  D
        721  CTCATCCCCATGGAGCATTGCACCACCCGCTTTTTCGAGACCTGTGACCTGGACAATGAC

261  K  Y  I  A  L  D  E  W  A  G  C  F  G  I  K  Q  K  D  I  D
        781  AAGTACATCGCCCTGGATGAGTGGGCCGGCTGCTTCGGCATCAAGCAGAAGGATATCGAC

281  K  D  L  V  I  *
        841  AAGGATCTTGTGATCTAA

*: stop codon
```

Fig. 8A

```
>gi|47938228|gb|BC072457.1|  Homo sapiens secreted protein, acidic,
cysteine-rich (osteonectin),
mRNA (cDNA clone MGC:88065 IMAGE:6186685), complete cds
Length=3178

Score = 4450 bits (2245),  Expect = 0.0
 Identities = 2256/2259 (99%), Gaps = 3/2259 (0%)
 Strand=Plus/Plus Query  1    CTCCACATTCCCGCGGTCCTTCAGACTGCCCGGAGAGCGCGCTCTGCCTGCCGCCTGCCT  60
            ||||||||||||||||||||||||||||||||||||||||||||||||||||||||||||
Sbjct  20   CTCCACATTCCCGCGGTCCTTCAGACTGCCCGGAGAGCGCGCTCTGCCTGCCGCCTGCCT  79

Query  61   GCCTGCCACTGAGGGTTCCCAGCACCATGAGGGCCTGGATCTTCTTTCTCCTTTGCCTGG  120
            ||||||||||||||||||||||||||||||||||||||||||||||||||||||||||||
Sbjct  80   GCCTGCCACTGAGGGTTCCCAGCACCATGAGGGCCTGGATCTTCTTTCTCCTTTGCCTGG  139

Query  121  CCGGGAGGGCCTTGGCAGCCCCTCA---AGAAGCCCTGCCTGATGAGACAGAGGTGGTGG  177
            |||||||||||||||||||||||||   ||||||||||||||||||||||||||||||||
Sbjct  140  CCGGGAGGGCCTTGGCAGCCCCTCAGCAAGAAGCCCTGCCTGATGAGACAGAGGTGGTGG  199

Query  178  AAGAAACTGTGGCAGAGGTGACTGAGGTATCTGTGGGAGCTAATCCTGTCCAGGTGGAAG  237
            ||||||||||||||||||||||||||||||||||||||||||||||||||||||||||||
Sbjct  200  AAGAAACTGTGGCAGAGGTGACTGAGGTATCTGTGGGAGCTAATCCTGTCCAGGTGGAAG  259

Query  238  TAGGAGAATTTGATGATGGTGCAGAGGAAACCGAAGAGGAGGTGGTGGCGGAAAATCCCT  297
            ||||||||||||||||||||||||||||||||||||||||||||||||||||||||||||
Sbjct  260  TAGGAGAATTTGATGATGGTGCAGAGGAAACCGAAGAGGAGGTGGTGGCGGAAAATCCCT  319

Query  298  GCCAGAACCACCACTGCAAACACGGCAAGGTGTGCGAGCTGGATGAGAACAACACCCCCA  357
            ||||||||||||||||||||||||||||||||||||||||||||||||||||||||||||
Sbjct  320  GCCAGAACCACCACTGCAAACACGGCAAGGTGTGCGAGCTGGATGAGAACAACACCCCCA  379

Query  358  TGTGCGTGTGCCAGGACCCCACCAGCTGCCCAGCCCCCATTGGCGAGTTTGAGAAGGTGT  417
            ||||||||||||||||||||||||||||||||||||||||||||||||||||||||||||
Sbjct  380  TGTGCGTGTGCCAGGACCCCACCAGCTGCCCAGCCCCCATTGGCGAGTTTGAGAAGGTGT  439

Query  418  GCAGCAATGACAACAAGACCTTCGACTCTTCCTGCCACTTCTTTGCCACAAAGTGCACCC  477
            ||||||||||||||||||||||||||||||||||||||||||||||||||||||||||||
Sbjct  440  GCAGCAATGACAACAAGACCTTCGACTCTTCCTGCCACTTCTTTGCCACAAAGTGCACCC  499

Query  478  TGGAGGGCACCAAGAAGGGCCACAAGCTCCACCTGGACTACATCGGGCCTTGCAAATACA  537
            ||||||||||||||||||||||||||||||||||||||||||||||||||||||||||||
Sbjct  500  TGGAGGGCACCAAGAAGGGCCACAAGCTCCACCTGGACTACATCGGGCCTTGCAAATACA  559

Query  538  TCCCCCCTTGCCTGGACTCTGAGCTGACCGAATTCCCCCTGCGCATGCGGGACTGGCTCA  597
            ||||||||||||||||||||||||||||||||||||||||||||||||||||||||||||
Sbjct  560  TCCCCCCTTGCCTGGACTCTGAGCTGACCGAATTCCCCCTGCGCATGCGGGACTGGCTCA  619

Query  598  AGAACGTCCTGGTCACCCTGTATGAGAGGGATGAGGACAACAACCTTCTGACTGAGAAGC  657
            ||||||||||||||||||||||||||||||||||||||||||||||||||||||||||||
Sbjct  620  AGAACGTCCTGGTCACCCTGTATGAGAGGGATGAGGACAACAACCTTCTGACTGAGAAGC  679

Query  658  AGAAGCTGCGGGTGAAGAAGATCCATGAGAATGAGAAGCGCCTGGAGGCAGGAGACCACC  717
            ||||||||||||||||||||||||||||||||||||||||||||||||||||||||||||
Sbjct  680  AGAAGCTGCGGGTGAAGAAGATCCATGAGAATGAGAAGCGCCTGGAGGCAGGAGACCACC  739
```

Fig. 8B

```
Query    718  CCGTGGAGCTGCTGGCCCGGGACTTCGAGAAGAACTATAACATGTACATCTTCCCTGTAC  777
              ||||||||||||||||||||||||||||||||||||||||||||||||||||||||||||
Sbjct    740  CCGTGGAGCTGCTGGCCCGGGACTTCGAGAAGAACTATAACATGTACATCTTCCCTGTAC  799

Query    778  ACTGGCAGTTCGGCCAGCTGGACCAGCACCCCATTGACGGGTACCTCTCCCACACCGAGC  837
              ||||||||||||||||||||||||||||||||||||||||||||||||||||||||||||
Sbjct    800  ACTGGCAGTTCGGCCAGCTGGACCAGCACCCCATTGACGGGTACCTCTCCCACACCGAGC  859

Query    838  TGGCTCCACTGCGTGCTCCCCTCATCCCCATGGAGCATTGCACCACCCGCTTTTTCGAGA  897
              ||||||||||||||||||||||||||||||||||||||||||||||||||||||||||||
Sbjct    860  TGGCTCCACTGCGTGCTCCCCTCATCCCCATGGAGCATTGCACCACCCGCTTTTTCGAGA  919

Query    898  CCTGTGACCTGGACAATGACAAGTACATCGCCCTGGATGAGTGGGCCGGCTGCTTCGGCA  957
              ||||||||||||||||||||||||||||||||||||||||||||||||||||||||||||
Sbjct    920  CCTGTGACCTGGACAATGACAAGTACATCGCCCTGGATGAGTGGGCCGGCTGCTTCGGCA  979

Query    958  TCAAGCAGAAGGATATCGACAAGGATCTTGTGATCTAAATCCACTCCTTCCACAGTACCG  1017
              ||||||||||||||||||||||||||||||||||||||||||||||||||||||||||||
Sbjct    980  TCAAGCAGAAGGATATCGACAAGGATCTTGTGATCTAAATCCACTCCTTCCACAGTACCG  1039

Query   1018  GATTCTCTCTTTAACCCTCCCCTTCGTGTTTCCCCCAATGTTTAAAATGTTTGGATGGTT  1077
              ||||||||||||||||||||||||||||||||||||||||||||||||||||||||||||
Sbjct   1040  GATTCTCTCTTTAACCCTCCCCTTCGTGTTTCCCCCAATGTTTAAAATGTTTGGATGGTT  1099

Query   1078  TGTTGTTCTGCCTGGAGACAAGGTGCTAACATAGATTTAAGTGAATACATTAACGGTGCT  1137
              ||||||||||||||||||||||||||||||||||||||||||||||||||||||||||||
Sbjct   1100  TGTTGTTCTGCCTGGAGACAAGGTGCTAACATAGATTTAAGTGAATACATTAACGGTGCT  1159

Query   1138  AAAAATGAAAATTCTAACCCAAGACATGACATTCTTAGCTGTAACTTAACTATTAAGGCC  1197
              ||||||||||||||||||||||||||||||||||||||||||||||||||||||||||||
Sbjct   1160  AAAAATGAAAATTCTAACCCAAGACATGACATTCTTAGCTGTAACTTAACTATTAAGGCC  1219

Query   1198  TTTTCCACACGCATTAATAGTCCCATTTTTCTCTTGCCATTTGTAGCTTTGCCCATTGTC  1257
              ||||||||||||||||||||||||||||||||||||||||||||||||||||||||||||
Sbjct   1220  TTTTCCACACGCATTAATAGTCCCATTTTTCTCTTGCCATTTGTAGCTTTGCCCATTGTC  1279

Query   1258  TTATTGGCACATGGGTGGACACGGATCTGCTGGGCTCTGCCTTAAACACACATTGCAGCT  1317
              ||||||||||||||||||||||||||||||||||||||||||||||||||||||||||||
Sbjct   1280  TTATTGGCACATGGGTGGACACGGATCTGCTGGGCTCTGCCTTAAACACACATTGCAGCT  1339

Query   1318  TCAACTTTTCTCTTTAGTGTTCTGTTTGAAACTAATACTTACCGAGTCAGACTTTGTGTT  1377
              ||||||||||||||||||||||||||||||||||||||||||||||||||||||||||||
Sbjct   1340  TCAACTTTTCTCTTTAGTGTTCTGTTTGAAACTAATACTTACCGAGTCAGACTTTGTGTT  1399

Query   1378  CATTTCATTTCAGGGTCTTGGCTGCCTGTGGGCTTCCCCAGGTGGCCTGGAGGTGGGCAA  1437
              ||||||||||||||||||||||||||||||||||||||||||||||||||||||||||||
Sbjct   1400  CATTTCATTTCAGGGTCTTGGCTGCCTGTGGGCTTCCCCAGGTGGCCTGGAGGTGGGCAA  1459

Query   1438  AGGGAAGTAACAGACACACGATGTTGTCAAGGATGGTTTTGGGACTAGAGGCTCAGTGGT  1497
              ||||||||||||||||||||||||||||||||||||||||||||||||||||||||||||
Sbjct   1460  AGGGAAGTAACAGACACACGATGTTGTCAAGGATGGTTTTGGGACTAGAGGCTCAGTGGT  1519

Query   1498  GGGAGAGATCCCTGCAGAACCCACCAACCAGAACGTGGTTTGCCTGAGGCTGTAACTGAG  1557
              ||||||||||||||||||||||||||||||||||||||||||||||||||||||||||||
Sbjct   1520  GGGAGAGATCCCTGCAGAACCCACCAACCAGAACGTGGTTTGCCTGAGGCTGTAACTGAG  1579

Query   1558  AGAAAGATTCTGGGGCTGTGTTATGAAAATATAGACATTCTCACATAAGCCCAGTTCATC  1617
              ||||||||||||||||||||||||||||||||||||||||||||||||||||||||||||
Sbjct   1580  AGAAAGATTCTGGGGCTGTGTTATGAAAATATAGACATTCTCACATAAGCCCAGTTCATC  1639
```

Fig. 8C

```
Query  1618  ACCATTTCCTCCTTTACCTTTCAGTGCAGTTTCTTTTCACATTAGGCTGTTGGTTCAAAC  1677
             ||||||||||||||||||||||||||||||||||||||||||||||||||||||||||||
Sbjct  1640  ACCATTTCCTCCTTTACCTTTCAGTGCAGTTTCTTTTCACATTAGGCTGTTGGTTCAAAC  1699

Query  1678  TTTTGGGAGCACGGACTGTCAGTTCTCTGGGAAGTGGTCAGCGCATCCTGCAGGGCTTCT  1737
             ||||||||||||||||||||||||||||||||||||||||||||||||||||||||||||
Sbjct  1700  TTTTGGGAGCACGGACTGTCAGTTCTCTGGGAAGTGGTCAGCGCATCCTGCAGGGCTTCT  1759

Query  1738  CCTCCTCTGTCTTTTGGAGAACCAGGGCTCTTCTCAGGGGCTCTAGGGACTGCCAGGCTG  1797
             ||||||||||||||||||||||||||||||||||||||||||||||||||||||||||||
Sbjct  1760  CCTCCTCTGTCTTTTGGAGAACCAGGGCTCTTCTCAGGGGCTCTAGGGACTGCCAGGCTG  1819

Query  1798  TTTCAGCCAGGAAGGCCAAAATCAAGAGTGAGATGTAGAAAGTTGTAAAATAGAAAAAGT  1857
             ||||||||||||||||||||||||||||||||||||||||||||||||||||||||||||
Sbjct  1820  TTTCAGCCAGGAAGGCCAAAATCAAGAGTGAGATGTAGAAAGTTGTAAAATAGAAAAAGT  1879

Query  1858  GGAGTTGGTGAATCGGTTGTTCTTTCCTCACATTTGGATGATTGTCATAAGGTTTTTAGC  1917
             ||||||||||||||||||||||||||||||||||||||||||||||||||||||||||||
Sbjct  1880  GGAGTTGGTGAATCGGTTGTTCTTTCCTCACATTTGGATGATTGTCATAAGGTTTTTAGC  1939

Query  1918  ATGTTCCTCCTTTTCTTCACCCTCCCCTTTTTCTTCTATTAATCAAGAGAAACTTCAAA  1977
             ||||||||||||||||||||||||||||||||||||||||||||||||||||||||||||
Sbjct  1940  ATGTTCCTCCTTTTCTTCACCCTCCCCTTTTTCTTCTATTAATCAAGAGAAACTTCAAA  1999

Query  1978  GTTAATGGGATGGTCGGATCTCACAGGCTGAGAACTCGTTCACCTCCAAGCATTTCATGA  2037
             ||||||||||||||||||||||||||||||||||||||||||||||||||||||||||||
Sbjct  2000  GTTAATGGGATGGTCGGATCTCACAGGCTGAGAACTCGTTCACCTCCAAGCATTTCATGA  2059

Query  2038  AAAAGCTGCTTCTTATTAATCATACAAACTCTCACCATGATGTGAAGAGTTTCACAAATC  2097
             ||||||||||||||||||||||||||||||||||||||||||||||||||||||||||||
Sbjct  2060  AAAAGCTGCTTCTTATTAATCATACAAACTCTCACCATGATGTGAAGAGTTTCACAAATC  2119

Query  2098  CTTCAAAATAAAAAGTAATGACTTAGAAACTGCCTTCCTGGGTGATTTGCATGTGTCTTA  2157
             ||||||||||||||||||||||||||||||||||||||||||||||||||||||||||||
Sbjct  2120  CTTCAAAATAAAAAGTAATGACTTAGAAACTGCCTTCCTGGGTGATTTGCATGTGTCTTA  2179

Query  2158  GTCTTAGTCACCTTATTATCCTGACACAAAAACACATGAGCATACATGTCTACACATGAC  2217
             ||||||||||||||||||||||||||||||||||||||||||||||||||||||||||||
Sbjct  2180  GTCTTAGTCACCTTATTATCCTGACACAAAAACACATGAGCATACATGTCTACACATGAC  2239

Query  2218  TACACAAATGCAAACCTTTGCAAACACATTATGCTTTTG  2256
             |||||||||||||||||||||||||||||||||||||||
Sbjct  2240  TACACAAATGCAAACCTTTGCAAACACATTATGCTTTTG  2278
```

Fig. 9

CLUSTAL W (1.81) multiple sequence alignment

Seq1            MRAWIFFLLCLAGRALAAPQQEALPDETEVVEETVAEVTEVSVGANPVQVEVGEFDDGAE
Seq2            MRAWIFFLLCLAGRALAAP-QEALPDETEVVEETVAEVTEVSVGANPVQVEVGEFDDGAE
                ***************** **************************************

Seq1            ETEEEVVAENPCQNHHCKHGKVCELDENNTPMCVCQDPTSCPAPIGEFEKVCSNDNKTFD
Seq2            ETEEEVVAENPCQNHHCKHGKVCELDENNTPMCVCQDPTSCPAPIGEFEKVCSNDNKTFD
                ************************************************************

Seq1            SSCHFFATKCTLEGTKKGHKLHLDYIGPCKYIPPCLDSELTEFPLRMRDWLKNVLVTLYE
Seq2            SSCHFFATKCTLEGTKKGHKLHLDYIGPCKYIPPCLDSELTEFPLRMRDWLKNVLVTLYE
                ************************************************************

Seq1            RDEDNNLLTEKQKLRVKKIHENEKRLEAGDHPVELLARDFEKNYNMYIFPVHWQFGQLDQ
Seq2            RDEDNNLLTEKQKLRVKKIHENEKRLEAGDHPVELLARDFEKNYNMYIFPVHWQFGQLDQ
                ************************************************************

Seq1            HPIDGYLSHTELAPLRAPLIPMEHCTTRFFETCDLDNDKYIALDEWAGCFGIKQKDIDKD
Seq2            HPIDGYLSHTELAPLRAPLIPMEHCTTRFFETCDLDNDKYIALDEWAGCFGIKQKDIDKD
                ************************************************************

Seq1            LVI
Seq2            LVI
                ***

Fig. 10A

SPARC Phylogenetic Sequence Comparisons

```
Current invention:
 MRAWIFFLLCLAGRALAAPQ EALPDETEVVEETVAEVTEVSVGANPVQVEVGEFDDGAE Homo sapien (Human wild type):
 MRAWIFFLLCLAGRALAAPQQEALPDETEVVEETVAEVTEVSVGANPVQVEVGEFDDGAE Pongo pygmaeus (Orangutan):
 MRAWIFFLLCLAGRALAAPQQEALPDETEVVEETVAEVTEVSVGANPVQVEVGEFDDGAE Bos taurus (cow):
 MRAWIFFLLCLAGRALAAPQQEALPDETEVVEETVAEVAEVPVGANPVQVEVGEFDDGAE Canis familiaris (cat):
 MRAWIFFLLCLAGRALAAPQQEALPDETEVVEETVAEVAEGPVGANPVQVEVGEFDEGAE Sus scrofa (pig):
 MRAWIFFLLCLAGKALAAPQQEALPDETEVVEETVAEVPV---GANPVQVEVGEFDDGAE Mus musculus (mouse):
 MRAWIFFLLCLAGRALAAPQQTEVAEEIVEEETVVEETGVPVGANPVQVEMGEFEDGAEE Rattus norvegicus (rat):
 MRAWIFFLLCLAGRALAAPQTEAAEEMVAEETVVEETGLPV-GANPVQVEMGEFEEGAEE Coturnix coturnix (quail):
 MRAWIFFLLCLAGKALAAPQEALPDETEVIEDVTTEEPV---GANPVQVEVGEFEEPTED Gallus gallus (chicken):
 MRTWIFFFLCLAGKALAAPQEALPDETEVIEDLTTEGPV---GANPVQVEVGEFEEPTED Xenopus laevis (African frog):
 MRVWVFFVLCLAGKALAAPQQDALPEEEEVIEDVPTEETV---GVNPVQVEVGEFDDAIN Xenopus tropicalis (pipid frog):
 MRVWVFFVLCLVGKALAAPQQDALPEEEEVIEDVPTEETV---GANPVQVEVGEFDDAVN Rana catesbeiana (bullfrog):
 MRVWIFFVLCLAGRALAAPQQDALPEEEEAIEDVATEEAVV--GSNPVQVEVGEFDEAIA Oryctolagus cuniculus (rabbit):
 MKAWIFFLVCLAGRALAAPQQEALPDETEVVEETVAEVAEVAEVPVGANPVQVEVGEFEE Oryzias latipes (rice fish):
 MRVWIVFLLCLAGHAMAAPAEEEP--ALEELVTEEPAEEVEVGANPVQVEVGEFDEAIEV Danio rerio (zebra fish):
 MRVWIFFLFCLAGKTLAAPTEEEP---------AVEEELEVGINPVQVETGEFDEAIEV
```

Fig. 10B

```
Sparus aurata (gilthead fish):
MRVWIVFVLCLAGHAMAAPTEE-EVIVEEPVTEEPVVEEIEVGANPVQVEVGEFDEAIEI Oncorhynchus mykiss (trout):
MRVWIVFLLCLAGQAFTASITEEEPIIDDVGEEAQPEV-------GVNPVQVETGDFDEA Takifugu rubripes (blowfish):
MRVWLLLVLCLAGSATAAPTE---EEEVFVEEMLTEEPEPEVGANPVQIEVGEFDEAIEI Tetraodon nigroviridis (pufferfish):
MRVWILFVLCLAASARAAPAEE-EAFVEELVTEEPVVEEPEVGANPVQIEVGEFDEAIEI
```

Restriction digest confirmation pVT1000Q3 Plasmid using EcoRI, EcoRV, NotI and SepI

Fig. 13

Insertional mutation of pVT1000Q3 to give pVT1000wt

5' Overlap       Insertion site   3' Overlap

Mutagenesis primer 5'<u>CCTTGGCAGCCCCTCA</u>GCAAGAAGCCCTGCC3'

Q3 mutant S— CCGGGAGGGCCTTGGCAGCCCCTCA +++ AGAAGCCCTGCCTG
Wild type S— CCGGGAGGGCCTTGGCAGCCCCTCAGCA AGAAGCCCTGCCTG

Fig. 14

```
Query    1    CTCCACATTCCCGCGGTCCTTCAGACTGCCCGGAGAGCGCGCTCTGCCTGCCGCCTGCCT    60
              ||||||||||||||||||||||||||||||||||||||||||||||||||||||||||||
Sbjct   20    CTCCACATTCCCGCGGTCCTTCAGACTGCCCGGAGAGCGCGCTCTGCCTGCCGCCTGCCT    79

Query   61    GCCTGCCACTGAGGGTTCCCAGCACCATGAGGGCCTGGATCTTCTTTCTCCTTTGCCTGG   120
              ||||||||||||||||||||||||||||||||||||||||||||||||||||||||||||
Sbjct   80    GCCTGCCACTGAGGGTTCCCAGCACCATGAGGGCCTGGATCTTCTTTCTCCTTTGCCTGG   139

SPARC-FQ3(SEQ ID NO: 7)(exon1) →
Query  121    CCGGGAGGGCCTTGGCAGCCCCTCA---AGAAGCCCTGCCTGATGAGACAGAGGTGGTGG   177
              ||||||||||||||||||||||||||    ||||||||||||||||||||||||||||||
Sbjct  140    CCGGGAGGGCCTTGGCAGCCCCTCAGCAAGAAGCCCTGCCTGATGAGACAGAGGTGGTGG   199
                        SPARC-FWT (SEQ ID NO: 8)(exon1) →

Query  178    AAGAAACTGTGGCAGAGGTGACTGAGGTATCTGTGGGAGCTAATCCTGTCCAGGTGGAAG   237
              ||||||||||||||||||||||||||||||||||||||||||||||||||||||||||||
Sbjct  200    AAGAAACTGTGGCAGAGGTGACTGAGGTATCTGTGGGAGCTAATCCTGTCCAGGTGGAAG   259
                        SPARC-FQ3&W (SEQ ID NO: 9)(exon2) →

Query  238    TAGGAGAATTTGATGATGGTGCAGAGGAAACCGAAGAGGAGGTGGTGGCGGAAAATCCCT   297
              ||||||||||||||||||||||||||||||||||||||||||||||||||||||||||||
Sbjct  260    TAGGAGAATTTGATGATGGTGCAGAGGAAACCGAAGAGGAGGTGGTGGCGGAAAATCCCT   319

Query  298    GCCAGAACCACCACTGCAAACACGGCAAGGTGTGCGAGCTGGATGAGAACAACACCCCCA   357
              ||||||||||||||||||||||||||||||||||||||||||||||||||||||||||||
Sbjct  320    GCCAGAACCACCACTGCAAACACGGCAAGGTGTGCGAGCTGGATGAGAACAACACCCCCA   379

Query  358    TGTGCGTGTGCCAGGACCCCACCAGCTGCCCAGCCCCCATTGGCGAGTTTGAGAAGGTGT   417
              ||||||||||||||||||||||||||||||||||||||||||||||||||||||||||||
Sbjct  380    TGTGCGTGTGCCAGGACCCCACCAGCTGCCCAGCCCCCATTGGCGAGTTTGAGAAGGTGT   439

Query  418    GCAGCAATGACAACAAGACCTTCGACTCTTCCTGCCACTTCTTTGCCACAAAGTGCACCC   477
              ||||||||||||||||||||||||||||||||||||||||||||||||||||||||||||
Sbjct  440    GCAGCAATGACAACAAGACCTTCGACTCTTCCTGCCACTTCTTTGCCACAAAGTGCACCC   499
                    ← SPARC-RQ3&W(exon 5 + 6 junction)
```

Q3 SPARC DELETION MUTANT AND USES THEREOF

CROSS-REFERENCE TO RELATED APPLICATIONS

This patent application claims the benefit of U.S. Provisional Patent Application No. 60/654,261 filed on Feb. 18, 2005, which is hereby incorporated by reference in its entirety.

FIELD OF THE INVENTION

This invention relates to methods for treating cancer, other diseases involving abnormal proliferative, hyperplastic, remodeling, and inflammatory activity in tissues and organs using antibody or other suitable ligands recognizing SPARC. The invention also relates to mutant SPARC polypeptides and nucleic acids and methods of their use, as well as methods for targeting, methods for imaging, and methods for determining the response of mammalian tumors to anti-SPARC therapy.

BACKGROUND OF THE INVENTION

Secreted protein acidic and rich in cysteine (also known as osteonectin, BM40, or SPARC) (hereafter "SPARC"), is a matrix-associated protein that elicits changes in cell shape, inhibits cell-cycle progression, and influences the synthesis of extracellular matrix (Bradshaw et al., Proc. Nat. Acad. Sci. USA 100: 6045-6050 (2003)). The murine SPARC gene was cloned in 1986 (Mason et al., EMBO J. 5: 1465-1472 (1986)) and a full-length human SPARC cDNA was cloned and sequenced in 1987 (Swaroop et al., Genomics 2: 37-47 (1988)). SPARC expression is developmentally regulated, and is predominantly expressed in tissues undergoing remodeling during normal development or in response to injury. For example, high levels of SPARC protein are expressed in developing bones and teeth (see, e.g., Lane et al., FASEB J., 8, 163 173 (1994); Yan & Sage, J. Histochem. Cytochem. 47:1495-1505 (1999)).

SPARC is upregulated in several aggressive cancers, but is absent in the corresponding inormal tissues (Porter et al., J. Histochem. Cytochem., 43, 791 (1995)). SPARC expression is induced among a variety of tumors (e.g., bladder, liver, ovary, kidney, gut, and breast). In bladder cancer, for example, SPARC expression has been associated with advanced carcinoma. Invasive bladder tumors of stage T2 or greater have been shown to express higher levels of SPARC relative to bladder tumors of stage T1 (or less superficial tumors), and poorer prognosis (see, e.g., Yamanaka et al., J. Urology, 166, 2495 2499 (2001)). In meningiomas, SPARC expression has been associated only with invasive tumors (see, e.g., Rempel et al., Clincal Cancer Res., 5, 237 241 (1999)). SPARC expression also has been detected in 74.5% of in situ invasive breast carcinoma lesions (see, e.g., Bellahcene, et al., Am. J. Pathol., 146, 95 100 (1995)), and 54.2% of infiltrating ductal carcinoma of the breast (see, e.g., Kim et al., J. Korean Med. Sci., 13, 652 657 (1998)). SPARC expression also has been associated with frequent microcalcification in breast cancer (see, e.g., Bellahcene et al., supra), suggesting that SPARC expression may be responsible for the affinity of breast metastases for the bone.

Surprisingly, SPARC has also been shown to have anti-tumor activity in some systems. SPARC is a potent cell cycle inhibitor that arrests cells in mid-$G_1$ (Yan & Sage, J. Histochem. Cytochem. 47:1495-1505 (1999)) and the inducible expression of SPARC has been shown to inhibit breast cancer cell proliferation in an in vitro model system (Dhanesuan et al., Breast Cancer Res. Treat. 75:73-85 (2002)). Similarly, exogenous SPARC can reduce the proliferation of both HOSE (human ovarian surface epithelial) and ovarian cancer cells in a concentration-dependent manner. In addition, SPARC induces apoptosis in ovarian cancer cells. Further evidence for SPARC receptors present on cells such as ovarian epithelial cells has been report. It has been proposed that the binding of SPARC to its receptor is likely to trigger tissue-specific signaling pathways that mediate its tumor suppressing functions (Yiu et al., Am. J. Pathol. 159:609-622 (2001)). Purified SPARC has also been reported to potently inhibit angiogenesis and significantly impair neuroblastoma tumor growth in an in vivo xenograft model system (Chlenski et al., Cancer Res. 62:7357-7363 (2002)).

SPARC also plays a role in non-neoplastic proliferative diseases. Mesangial cell proliferation is a characteristic feature of many glomerular diseases and often precedes extracellular matrix expansion and glomerulosclerosis. In a model of experimental mesangioproliferative glomerulonephritis, SPARC mRNA was increased 5-fold by day 7 and was identified in the mesangium by in situ hybridization. However, recombinant SPARC or a synthetic SPARC peptide inhibited platelet-derived-growth-factor-induced mesangial cell DNA synthesis in vitro (Pichler et al., Am. J. Pathol. 148(4):1153-67 (1996)). Similarly, while renal enlargement, due to hyperplasia, hypertrophy, and increase inter-cellular matrix, is a characteristic feature of diabetes in humans, kidney SPARC mRNA levels fell in diabetic animals. In addition, the onset of diabetes-related kidney growth is associated with a reduction in SPARC mRNA and protein (Gilbert et al., Kidney Int. 48(4):1216-25 (1995)).

SPARC has been implicated in the pathogenesis of atherosclerotic lesions. Plasma SPARC levels are elevated in patients with coronary artery disease (Masahiko et al., Obesity Res. 9:388-393 (2001)). The proliferation of vascular smooth muscle cells in the arterial intima plays a central role in the pathogenesis of atherosclerosis. SPARC is expressed in vascular smooth muscle cells and macrophages associated with atherosclerotic lesions. In addition, SPARC has been hypothesized to regulate the action of platelet-derived growth factor during vascular injury (Masahiko et al., Obesity Res. 9:388-393 (2001); Raines et al., Proc. Nati. Acad. Sci. USA 89:1281-1285 (1992)). A stimulating effect of SPARC on endothelial PAI-1 production has been reported at the site of vascular injury (Hasselaar et al., J. Biol. Chem. 266:13178-13184 (1991)) and has been postulated to accelerate atherosclerosis (Masahiko et al., Obesity Res. 9:388-393 (2001)).

SPARC has affinity for a wide variety of ligands including cations (e.g., Ca 2+, Cu 2+, Fe 2+), growth factors (e.g., platelet derived growth factor (PDGF), and vascular endothelial growth factor (VEGF)), extracellular matrix (ECM) proteins (e.g., collagen I V and collagen IX, vitronectin, and thrombospondin 1), endothelial cells, platelets, albumin, and hydroxyapaptite (see, e.g., Lane et al., FASEB J., 8, 163 173 (1994); Yan & Sage, J. Histochem. Cytochem. 47:1495-1505 (1999)). SPARC is also known to bind albumin (see, e.g., Schnitzer, J. Biol. Chem., 269, 6072 (1994)).

Antibody therapy is an effective method for controlling disease wherein a specific protein marker can be identified. Examples include Avastin (anti-VEGF antibody), Rituxan (anti-CD20 antibody), and Remicade (anti-TNF antibody). As such, antibody against SPARC represent an important therapeutic agent for treating human and other mammalian tumors, or other proliferative, hyperplastic, remodeling, and inflammatory disorders, that express the SPARC protein.

Accordingly, there is a need for novel forms of SPARC and antibodies reactive with such novel forms of SPARC. The present invention provides for such novel SPARC polypeptides, nucleic acids which encode such novel SPARC polypeptides, and methods of use of such novel SPARC polypeptides and nucleic acids. The invention additionally provides for antibodies against SPARC polypeptides.

BRIEF SUMMARY OF THE INVENTION

The glutamine corresponding to amino acid 20 in SEQ ID NO: 1 (the sequence of the unprocessed primary translation product) corresponds to the glutamine at amino acid position 3 in the mature protein (the polypeptide without the 17 amino acid SPARC leader sequence) (the "Q3" glutamine). The invention provides for an isolated SPARC polypeptide comprising an amino acid sequence wherein the glutamine corresponding to amino acid 20 in SEQ ID NO: 1 is deleted (hereafter "Q3 SPARC deletion mutant polypeptide"). In particular, the invention provides for an isolated human Q3 SPARC deletion mutant polypeptide. The invention also provides for an isolated SPARC polypeptide, wherein the polypeptide comprises the amino acid sequence of SEQ ID NO: 2, which corresponds to a mature Q3 SPARC deletion mutant polypeptide. The invention further provides for an isolated nucleic acid molecule encoding a Q3 SPARC deletion mutant polypeptide. In particular, the invention provides for an isolated nucleic acid molecule encoding human Q3 SPARC deletion mutant polypeptide. Isolated nucleic acids encompassed by the invention include, but are not limited to, nucleic acids comprising the sequence of SEQ ID NO: 3.

The invention also provides for a vector comprising a nucleic acid molecule encoding a Q3 SPARC deletion mutant polypeptide including, but not limited to, wherein the vector further comprises a promoter controlling the expression of the Q3 SPARC deletion mutant polypeptide encoding nucleic acid sequences. In addition, the invention provides for a cell comprising a nucleic acid molecule encoding a Q3 SPARC deletion mutant polypeptide, wherein the cell is either a prokaryotic cell or a eukaryotic cell. The invention further provides for a method of making a Q3 SPARC deletion mutant polypeptide of comprising: (a) transforming cells with a nucleic acid encoding a Q3 SPARC deletion mutant polypeptide; (b) inducing the expression of the Q3 SPARC deletion mutant polypeptide by the transformed cells, and (c) purifying the Q3 SPARC deletion mutant polypeptide.

In another embodiment the invention provides for composition comprising a Q3 SPARC deletion mutant polypeptide or a nucleic acid encoding a Q3 SPARC deletion mutant polypeptide and a pharmaceutically acceptable carrier and method of treating a disease comprising administering the Q3 SPARC deletion mutant polypeptide and carrier. Such a method can be used in accordance with the invention to treat a disease including, without limitation, wherein the disease is a cell proliferative disease (e.g., cancer, benign tumor, atherosclerosis, vascular restenosis). The invention also provides for a method of sensitizing a disease comprising administering a Q3 SPARC deletion mutant polypeptide including wherein the disease is a cell proliferative disease (e.g., cancer, benign tumor, atherosclerosis, vascular restenosis). In addition, the invention provides for compositions comprising a Q3 SPARC deletion mutant polypeptide, wherein the polypeptide is coupled or conjugated to a therapeutic or diagnostic agent, such as, e.g., a radioisotope or radionuclide, drug, polypeptide or toxin. Alternatively, the Q3 SPARC deletion mutant polypeptide can be coupled or conjugated to molecule which stabilizes the Q3 SPARC deletion mutant polypeptide in vivo, such as, e.g., a polyethylene glycol. The Q3 SPARC deletion mutant polypeptide or nucleic acid encoding a Q3 SPARC deletion mutant polypeptide and pharmaceutically acceptable carrier can be administered through any suitable route including, without limitation, intravenous, intraperitoneal, intratumoral, or inhalational.

In one embodiment the invention provides for antibody or fragment thereof with recognition for a SPARC polypeptide, in particular for a Q3 SPARC deletion mutant polypeptide, and a pharmaceutically acceptable carrier. Such an antibody with recognition for a SPARC polypeptide, can be used in accordance with the invention to, e.g., mediate complement activation and/or cell mediated cytotoxicity against the tumor or other proliferative disease.

In yet another embodiment, the invention provides for a composition comprising a therapeutic agent coupled to an antibody or fragment thereof with recognition for a SPARC polypeptide, in particular for a Q3 SPARC deletion mutant polypeptide, and a pharmaceutically acceptable carrier including, without limitation, wherein said antibody or fragments thereof are humanized and include monovalent Fab', divalent Fab2, scfv, diabody, or a chimera (hereafter collectively an "anti-Q3 SPARC deletion mutant antibody.") The antibody prepared in accordance with the invention can be monoclonal or polyclonal, manufactured in non-human animals, and be humanized. In addition, the invention provides for an anti-SPARC antibody, in particular, an anti-Q3 SPARC deletion mutant antibody, coupled or conjugated to a therapeutic agent, wherein the therapeutic agent is a chemotherapeutic drug, radionuclide, or peptide. Suitable therapeutic agents also include therapeutic agents that are biological molecules such as, e.g, tTF and TNF.

The Q3 SPARC deletion mutant polypeptide or anti-SPARC antibody, such as, e.g., anti-Q3 SPARC deletion mutant antibody, and pharmaceutically acceptable carrier can be administered through any suitable route including, without limitation, intravenous, intraperitoneal, intratumoral, or inhalational. Accordingly, the invention provides for a method for delivering a therapeutic agent to a disease site, such as, e.g., a tumor in a mammal, which method comprises administering to the mammal a therapeutically effective amount of a pharmaceutical composition, wherein the therapeutic agent comprises a chemotherapeutic agent or radioactive agent coupled to an pharmaceutically acceptable carrier and a pharmaceutically acceptable carrier. Suitable tumors that can be treated in accordance with the invention include, without limitation, tumors located in the bladder, liver, ovary, kidney, gut, brain, or breast of a human or non-human animal.

The invention additionally provides for a method for delivering a diagnostic agent to a disease site, such as, e.g., a tumor in a mammal, which method comprises administering to the mammal a diagnostically effective amount of a pharmaceutical composition. Suitable such compositions include, without limitation, wherein the composition comprises a diagnostic agent coupled to an anti-SPARC antibody, such as, e.g., an anti-Q3 SPARC deletion mutant antibody, and a pharmaceutically acceptable carrier. Suitable diagnostic agents include, without limitation, radioactive agents, MRI contrast agents, X-Ray contrast agents, ultrasound contrast agents, and PET contrast agents.

The invention provides for a method of classifying a disease comprising detecting a SPARC polypeptide with a deletion of the glutamine corresponding to amino acid position 20 in SEQ ID NO: 1 (i.e., detecting a Q3 SPARC deletion mutant polypeptide) including, without limitation, wherein the disease is characterized by cellular proliferation such as, e.g., cancer, benign tumor, atherosclerosis or vascular restenosis. Suitable diseases also include, without limitation, those where neoangiogenesis occurs. As such, the invention further provides for a method of detecting a SPARC polypeptide wherein the detected polypeptide comprises the amino acid sequence of SEQ ID NO: 2.

The invention additionally provides for a method of classifying a disease comprising detecting a nucleic acid encoding a Q3 SPARC deletion mutant polypeptide, wherein the nucleic acid is DNA or RNA. Further, the invention provides a method of classifying a disease comprising detecting a nucleic acid, wherein the nucleic acid detected comprises the nucleic sequence of SEQ ID NO: 3.

BRIEF DESCRIPTION OF THE SEVERAL VIEWS OF THE DRAWING(S)

FIG. 1 illustrates albumin and SPARC staining in MX 1 tumor xenografts.

Figure 3:
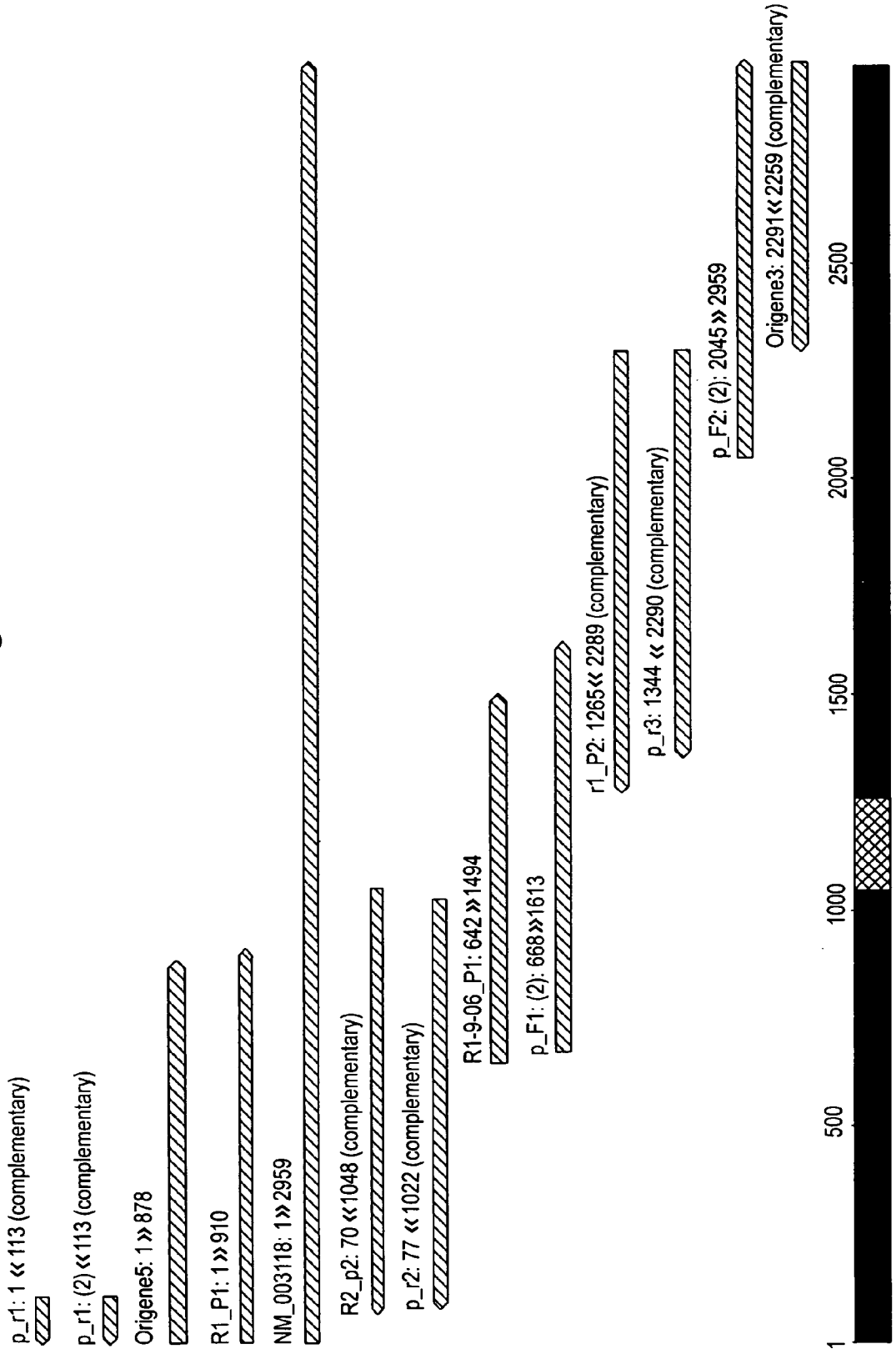
FIG. 3 illustrates the sequencing strategy used to determine the SPARC DNA sequence of the SPARC cDNA clone isolated from the human prostate cDNA library.

FIG. 4A-U disclose the results of the sequencing reactions depicted in FIG. 3.

FIG. 5 discloses the DNA sequence of SEQ ID NO: 3.

FIG. 6 discloses the amino acid sequence of SEQ ID NO: 4 which is a translation of SEQ ID NO: 5.

FIG. 7 discloses the amino acid sequence of SEQ ID NO: 2 which is a translation of SEQ ID NO: 6.

FIG. 8A-C illustrate a DNA sequence alignment of SEQ ID NO: 3 (Query) with the wild type SPARC cDNA sequence (Sbjct).

FIG. 9 illustrates an amino acid sequence alignment of the wild type SPARC amino acid sequence (seq1) with SEQ ID NO: 4 (seq2).

FIG. 10A-B disclose a phylogenetic comparison of SPARC amino acid sequences.

Figure 11:
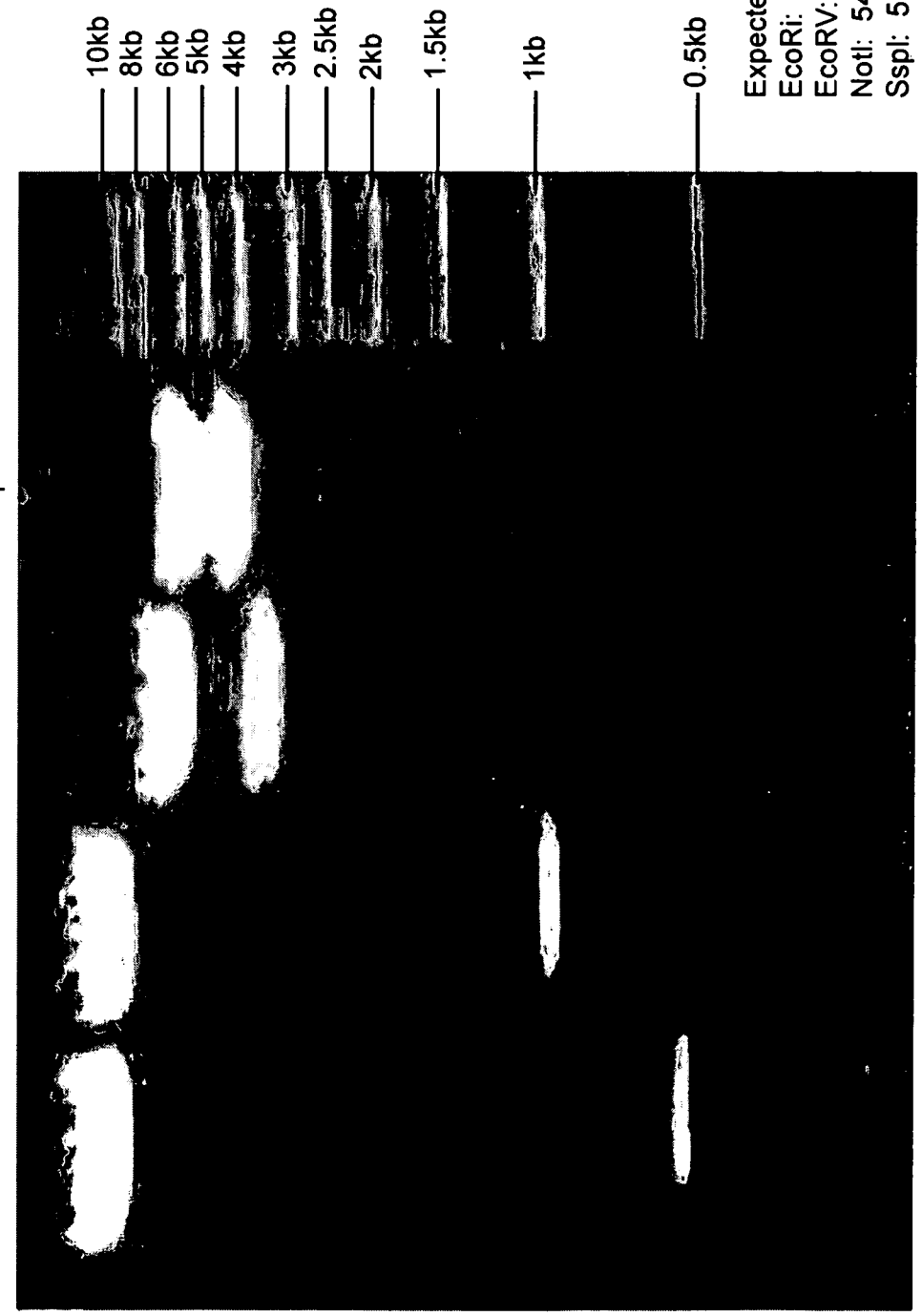

FIG. 11 depicts the gel electrophoresis results of confirmatory restriction digests of the pVT1000Q3 plasmid.

Figure 12:
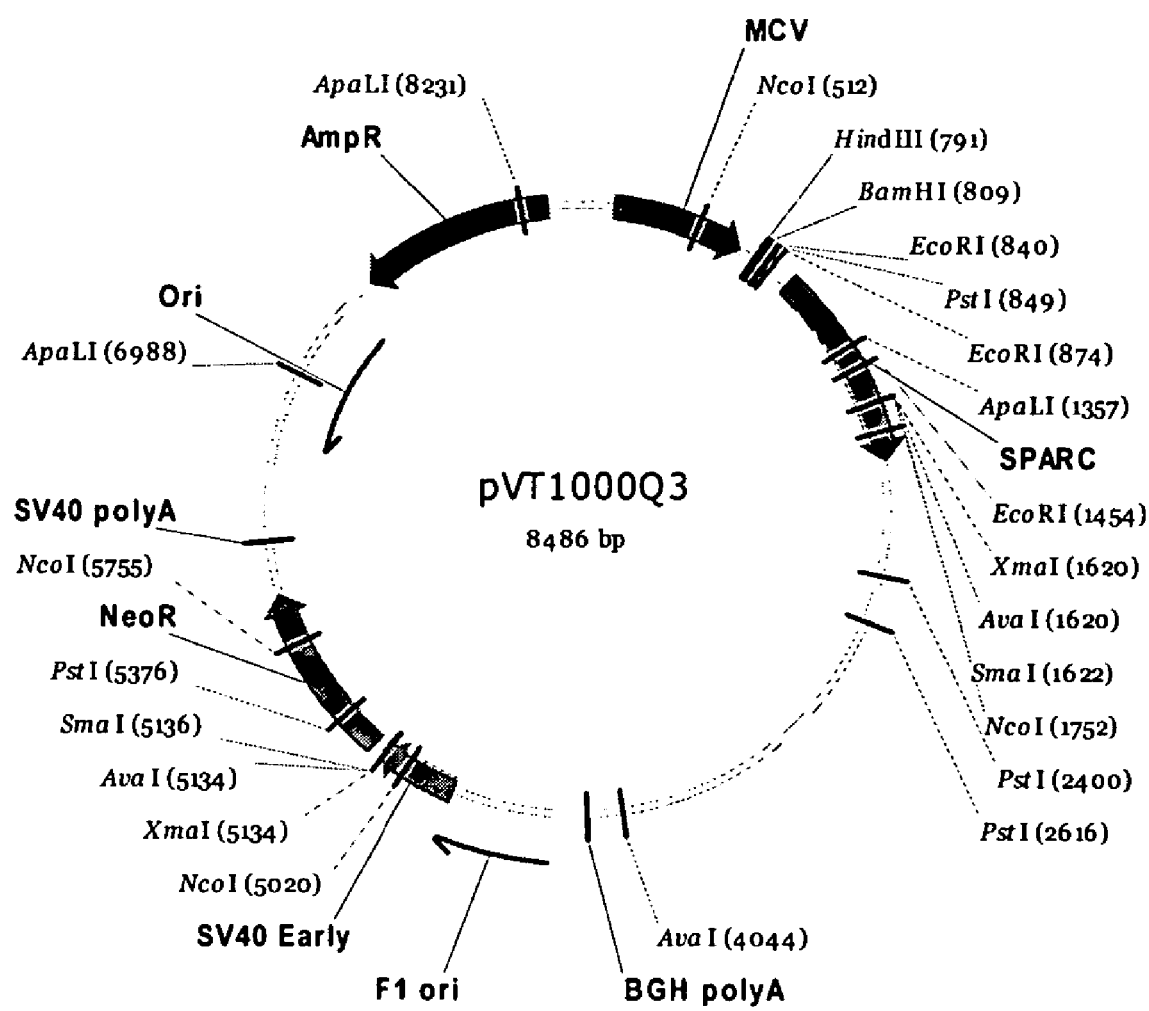

FIG. 12 depicts the restriction map of the pVT1000Q3 plasmid.

FIG. 13 illustrates a mutagenic primer used in a site directed mutagenesis method and the sequences targetted.

FIG. 14 illustrates the positions and sequences of PCR primers used to detect the presence of nucleic acids encoding a Q3 SPARC deletion mutant polypeptide and/or a wild type SPARC polypeptide ("Query", mutant sequence; "Sbjct", wild type sequence).

Figure 15:
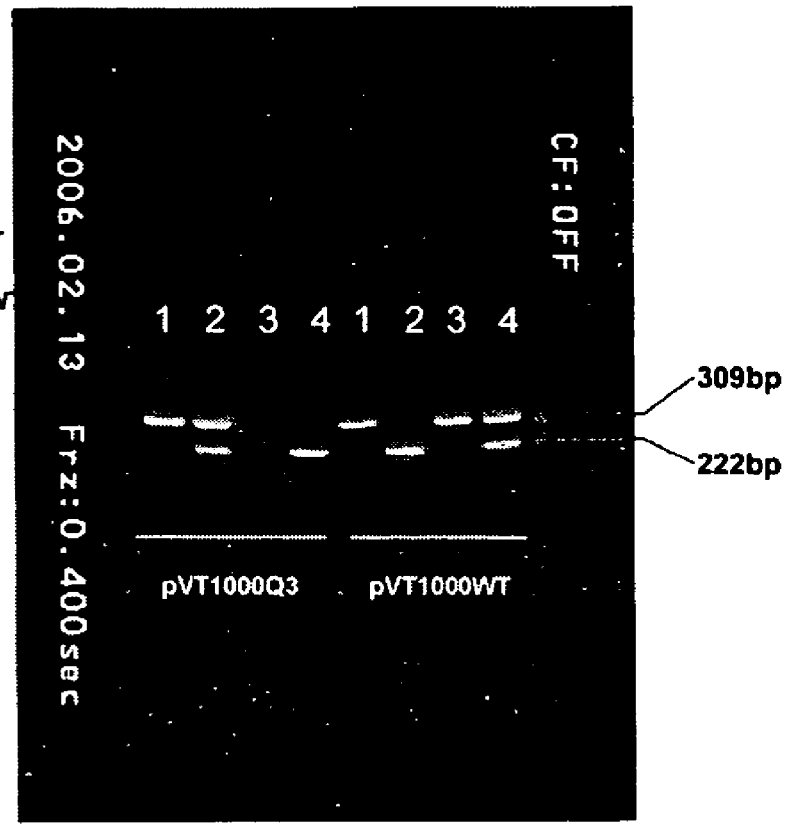

FIG. 15 depicts the gel electrophoresis results of PCR reactions used to detect the presence of nucleic acids encoding a Q3 SPARC deletion mutant polypeptide and/or a wild type SPARC polypeptide.

DETAILED DESCRIPTION OF THE INVENTION

The human SPARC gene encodes a 303 amino acid SPARC protein, while mature SPARC is a 285 amino acid glycoprotein. After cleavage of the signal sequence a 32-kD secreted form is produced which migrates at 43 kD on SDS-PAGE because of glycosylation. Crystallographic data indicates the SPARC protein has three modular domains. The N-terminal domain is acidic and binds calcium. The central "follistatin-like domain" contains amino acids involved in the inhibition of angiogenesis and focal adhesion plaque formation and the (K)GHK angiogenic peptide. The carboxyl terminal "E-C domain" contains the amino acids involved in high affinity calcium binding and the inhibition of cell spreading (Yan & Sage, J. Histochem. Cytochem. 7:1495-1505, 1999).

The N-terminal SPARC domain (residues 1-52 after a 17-amino-acid signal sequence) is an acidic region rich in Aspartic Acid and Glutamic Acid. The N-terminal domain binds several calcium ions with low affinity, interacts with hydroxyapatite, and has been postulated to play a role in bone mineralization. This N-terminal SPARC domain has also been shown to inhibit cell spreading and chemotaxis (Yan & Sage, J. Histochem. Cytochem. 47:1495-1505 (1999)). Further, the N-terminal domain contains the major immunological epitopes of SPARC. However, this domain is the divergent sequence among the family of SPARC-like proteins and antibodies against SPARC have not been found to crossreact with or recognize SPARC-like proteins (Yan & Sage, J. Histochem. Cytochem. 7:1495-1505, 1999).

Two adjacent glutamines within the N-terminal domain at amino acid positions 3 and 4 in the mature SPARC protein (amino acids positions 20 and 21 in the unprocessed protein) are amine acceptor sites which are the primary targets for crosslinking by transglutaminase$_c$. (Glutamine is represented by "Q" in the single-letter amino acid code, thus, these amino acids are the "Q3" and "Q4" amino acids in the mature SPARC protein.) Transglutaminases catalyze the Ca-dependent transfer reaction between the gamma-carboxamide group of a peptide-bound glutamine residue and various primary amines. It has been proposed that tissue-specific posttranslational modifications, such as transglutaminase cross-linking, may modulate some of SPARC's biological functions (Hohenadl et al., J. Biol. Chem. 270: 23415-23420 (1995)).

The invention provides for an isolated SPARC polypeptide comprising an amino acid sequence wherein the glutamine corresponding to amino acid 20 in SEQ ID NO: 1 is deleted (a Q3 SPARC deletion mutant polypeptide). In particular, the invention provides for an isolated human Q3 SPARC deletion mutant polypeptide. The invention also provides for an isolated SPARC polypeptide, wherein the polypeptide comprises the amino acid sequence of SEQ ID NO: 2, which corresponds to a mature Q3 SPARC deletion mutant polypeptide (the polypeptide without the 17 amino acid SPARC leader sequence).

The invention further provides for an isolated nucleic acid molecule encoding a Q3 SPARC deletion mutant polypeptide. In particular, the invention provides for an isolated nucleic acid molecule encoding human Q3 SPARC deletion mutant polypeptide. Isolated nucleic acids encompassed by the invention include, but are not limited to, nucleic acids comprising the sequence of SEQ ID NO: 3. Accordingly, the invention provides for an isolated SPARC polypeptide, wherein the polypeptide comprises the amino acid sequence of SEQ ID NO: 4, which corresponds to the translation of the SEQ ID NO: 3 DNA sequence from nucleotide 87 through nucleotide 992 and which results in a full length Q3 SPARC deletion mutant polypeptide (a SPARC polypeptide with the 17 amino acid SPARC leader sequence). Also accordingly, the invention provides for isolated nucleic acids with the DNA sequences of SEQ ID NO: 5 and SEQ ID NO: 6 which, respectively, encode polypeptides with the amino acid sequences of SEQ ID NO: 4 and SEQ ID NO: 2. The DNA sequence of SEQ ID NO: 6 represents nucleotides 138 through 992 of SEQ ID NO: 3.

The invention provides for an isolated SPARC polypeptide comprising an amino acid sequence wherein the glutamine corresponding to amino acid 20 in SEQ ID NO: 1 is deleted. Accordingly, the invention provides for an isolated Q3 SPARC deletion mutant polypeptide and wherein the polypeptide is at least about 10 amino acids long, preferably is at least about 15 amino acids long, more preferably is at least about 20 amino acids long, more preferably is at least about 30 amino acids long, more preferably is at least about 40 amino acids long, more preferably is at least about 50 amino acids long, even more preferably is at least about 100 amino acids long. Further, the invention provides for an isolated Q3 SPARC deletion mutant polypeptide comprising a polypeptide wherein the sequences other than the glutamine corresponding to amino acid 20 in SEQ ID NO: 1 are at least about 80% homologous to the corresponding sequences of SEQ ID NO: 1, preferably at least about 90% homologous to the corresponding sequences of SEQ ID NO: 1, even more preferably at least about 95% homologous to the corresponding sequences of SEQ ID NO: 1, even more preferably at least about 99% homologous to the corresponding sequences of SEQ ID NO: 1. By "corresponding sequences of SEQ ID NO: 1" it is meant, those sequences which align with the sequences of SEQ ID NO: 1 wherein the region of alignment is at least about 10 amino acids long, preferably is at least about 15 amino acids long, more preferably is at least about 20 amino acids long, more preferably is at least about 30 amino acids long, more preferably is at least about 40 amino acids long, more preferably is at least about 50 amino acids long, even more preferably is at least about 100 amino acids long. Various methods of sequence alignment are known in the biotechnology arts (see, e.g., Rosenberg, BMC Bioinformatics 6:278 (2005); Altschul et al., FEBS J. 272(20): 5101-5109 (2005)).

The invention also provides for an isolated SPARC polypeptide, wherein the polypeptide comprises the amino acid sequence of SEQ ID NO: 2, including polypeptides comprising the amino acid sequence of SEQ ID NO: 2 without any additional amino acids added to the amino or carboxyl terminus, as well as polypeptides comprising the amino acid sequence of SEQ ID NO: 2 with an additional at least about 1 amino acid, preferably with an additional at least about 5 amino acids, preferably with an additional at least about 10 amino acids, more preferably with an additional at least about 15 amino acids, more preferably with an additional at least about 20 amino acids, more preferably with an additional at least about 30 amino acids, more preferably with an additional at least about 40 amino acids, even more preferably with an additional at least about 50 amino acids added to the amino and/or carboxy termini of SEQ ID NO: 2.

The invention further provides for a Q3 SPARC deletion mutant polypeptide wherein conservative substitutions have been made in the amino acid sequence, including wherein the substituted amino acids comprise natural and/or non-natural amino acids. In order to exemplify what is meant by conservative substitution, Groups A-F are listed below. The replacement of one member of the following groups by another member of the same group is considered to be a conservative substitution.

Group A includes leucine, isoleucine, valine, methionine, phenylalanine, serine, cysteine, threonine, and modified amino acids having the following side chains: ethyl, iso-butyl, —$CH_2CH_2OH$, —$CH_2CH_2CH_2OH$, —$CH_2CHOHCH_3$ and $CH_2SCH_3$.

Group B includes glycine, alanine, valine, serine, cysteine, threonine, and a modified amino acid having an ethyl side chain.

Group C includes phenylalanine, phenylglycine, tyrosine, tryptophan, cyclohexylmethyl, and modified amino residues having substituted benzyl or phenyl side chains.

Group D includes glutamic acid, aspartic acid, a substituted or unsubstituted aliphatic, aromatic or benzylic ester of glutamic or aspartic acid (e.g., methyl, ethyl, n-propyl, iso-propyl, cyclohexyl, benzyl, or substituted benzyl), glutamine, asparagine, CO—NH-alkylated glutamine or asparagine (e.g., methyl, ethyl, n-propyl, and iso-propyl), and modified amino acids having the side chain —$(CH_2)_3$COOH, an ester thereof (substituted or unsubstituted aliphatic, aromatic, or benzylic ester), an amide thereof, and a substituted or unsubstituted N-alkylated amide thereof.

Group E includes histidine, lysine, arginine, N-nitroarginine, p-cycloarginine, g-hydroxyarginine, N-amidinocitruline, 2-amino guanidinobutanoic acid, homologs of lysine, homologs of arginine, and ornithine.

Group F includes serine, threonine, cysteine, and modified amino acids having C1-C5 straight or branched alkyl side chains substituted with —OH or —SH.

Groups A-F are exemplary and are not intended to limit the invention.

Additionally, the invention provides for isolated Q3 SPARC deletion mutant polypeptides with one or more amino acid insertions or deletions of from about 1 to about 5 amino acids, preferably from about 1 to about 3 amino acids, more preferably 1 amino acid, in the SEQ ID NO: 1 sequence.

The invention further provides for an isolated nucleic acid molecule encoding a Q3 SPARC deletion mutant polypeptide. Suitable isolated nucleic acids include, without limitation, DNA, RNA, and peptide-nucleic acids. Isolated nucleic acids encompassed by the invention include, but are not limited to, nucleic acids comprising the sequence of SEQ ID NO: 3 without additional 5' or 3' nucleotides or with an additional at least about 1 nucleotide, preferably an additional at least about 3 nucleotides, more preferably at least about 9 nucleotides, more preferably at least about 20 nucleotides, more preferably at least about 50 nucleotides, more preferably at least about 100 nucleotides, even more preferably at least about 1,000 nucleotides added to the 5' and/or 3' ends of SEQ ID NO: 3. The invention also provides for an isolated nucleic acid molecule encoding a Q3 SPARC deletion mutant polypeptide wherein the nucleic acid sequence is at least about 80% homologous to the corresponding sequences of SEQ ID NO: 3, preferably at least about 90% homologous to the corresponding sequences of SEQ ID NO: 3, even more preferably at least about 95% homologous to the corresponding sequences of SEQ ID NO: 3, even more preferably at least about 99% homologous to the corresponding sequences of SEQ ID NO: 3. By "corresponding sequences of SEQ ID NO: 3" it is meant, those sequences which align with the sequences of SEQ ID NO: 3 wherein the region of alignment is at least about 30 nucleotides long, preferably is at least about 45 nucleotides long, more preferably is at least about 60 nucleotides long, more preferably is at least about 90 nucleotides long, more preferably is at least about 120 nucleotides long, more preferably is at least about 150 nucleotides long, even more preferably is at least about 300 nucleotides long. Various methods of sequence alignment are known in the biotechnology arts (see, e.g., Rosenberg, BMC Bioinformatics 6:278 (2005); Altschul et al., FEBS J. 272(20): 5101-5109 (2005)).

In addition, the invention provides for an isolated nucleic acid molecule encoding a Q3 SPARC deletion mutant polypeptide polypeptide wherein the isolated nucleic acid molecule hybridizes to SEQ ID NO: 3 under low stringency conditions, preferably under moderately stringent conditions, even more preferably under highly stringent conditions. "High stringency conditions" preferably allow for from about 25% to about 5% mismatch, more preferably from about 15% to about 5% mismatch, and most preferably from about 10% to about 5% mismatch of the nucleic acid sequence. "Moderately stringent conditions" preferably allow for from about 40% to about 15% mismatch, more preferably from about 30% to about 15% mismatch, and most preferably from about 20% to about 15% mismatch of the nucleic acid sequence. "Low stringency conditions" preferably allow for from about 60% to about 35% mismatch, more preferably from about 50% to about 35% mismatch, and most preferably from about 40% to about 35% mismatch of the nucleic acid sequence.

The absence of non-specific binding may be tested by the use of a second target which lacks even a partial degree of complementarity (e.g., less than about 30% identity); in the absence of non-specific binding the probe will not hybridize to the second non-complementary target. There can be partial homology or complete homology (i.e., identity). A partially complementary sequence is one that at least partially inhibits a completely complementary sequence from hybridizing to a target nucleic acid. The inhibition of hybridization of the completely complementary sequence to the target sequence may be examined using a hybridization assay (Southern or Northern blot, solution hybridization and the like) under conditions of low stringency. A "substantially homologous" sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The term "homology" refers to a degree of complementarity.

Exemplary moderate stringency conditions include overnight incubation at 37° C. in a solution comprising 20% formamide, 5×SSC (150 mM NaCl and 15 mM trisodium citrate), 50 mM sodium phosphate (pH 7.6), 5× Denhardt's solution, 10% dextran sulfate, and 20 mg/ml denatured sheared salmon sperm DNA, followed by washing in 1×SSC at about 37-50° C., or substantially similar conditions, e.g., the moderately stringent conditions described in Sambrook & Russell, Molecular Cloning: A Laboratory Manual, Cold Spring Harbor Laboratory Press, New York (2001), pp. 6.1-6.62. High stringency conditions are conditions that, for example (1) use low ionic strength and high temperature for washing, such as with a composition comprising 0.015 M sodium chloride and 0.0015 M sodium citrate, and 0.1% (w/v) sodium dodecyl sulfate (SDS) at 50° C., (2) employ a denaturing agent during hybridization, such as a composition comprising formamide, for example, 50% (v/v) formamide with 0.1% (w/v) bovine serum albumin (BSA), 0.1% Ficoll, 0.1% polyvinylpyrrolidone (PVP), and 50 mM sodium phosphate buffer at pH 7.5 with 750 mM sodium chloride and 75 mM sodium citrate at 42° C., or (3) employ a composition comprising 50% formamide, 5×SSC (0.75 M NaCl and 0.075 M sodium citrate), 50 mM sodium phosphate (pH 6.8), 0.1% sodium pyrophosphate, 5× Denhardt's solution, and sonicated salmon sperm DNA (50 μg/ml), 0.1% SDS, and 10% dextran sulfate at 42° C., with washes at (i) 42° C. in 0.2×SSC, (ii) at 55° C. in 50% formamide, and (iii) at 55° C. in 0.1×SSC (preferably in combination with EDTA).

The invention further provides for nucleic acid encoding a Q3 SPARC deletion mutant polypeptide with conservative amino acid substitutions including (a) the change of a leucine, isoleucine, valine, methionine, phenylalanine, serine, cysteine, or threonine to a leucine, isoleucine, valine, methionine, phenylalanine, serine, cysteine, or threonine, (b) the change of a glycine, alanine, valine, serine, cysteine, or threonine to a glycine, alanine, valine, serine, cysteine, or threonine, (c) the change of a phenylalanine, tyrosine, or tryptophan to a phenylalanine, tyrosine, or tryptophan, (d) the change of a glutamic acid, aspartic acid, glutamine, or asparagine to a glutamic acid, aspartic acid, glutamine, or asparagine (e) the change of a histidine, lysine, or arginine to a histidine, lysine, or arginine, and (f) the change of a serine, threonine, or cysteine to a serine, threonine, or cysteine, and (g) combinations thereof.

Additionally, the invention provides for isolated nucleic acids encoding Q3 SPARC deletion mutant polypeptides with one or more amino acid insertions or deletions of from about 1 to about 5 amino acids, preferably from about 1 to about 3 amino acids, more preferably 1 amino acid, in the SEQ ID NO: 1 sequence.

Mutagenesis can be undertaken by any of several methods known in the art. Generally, mutagenesis can be accomplished by cloning the nucleic acid sequence into a plasmid or some other vector for ease of manipulation of the sequence. Then, a unique restriction site at which further nucleic acids can be added into the nucleic acid sequence is identified or inserted into the nucleic acid sequence. A double-stranded synthetic oligonucleotide generally is created from overlapping synthetic single-stranded sense and antisense oligonucleotides such that the double-stranded oligonucleotide incorporates the restriction sites flanking the target sequence and, for instance, can be used to incorporate replacement DNA. The plasmid or other vector is cleaved with the restriction enzyme, and the oligonucleotide sequence having compatible cohesive ends is ligated into the plasmid or other vector to replace the original DNA.

Other means of in vitro site-directed mutagenesis are known to those skilled in the art, and can be accomplished (in particular, using an overlap-extension polymerase chain reaction (PCR), see, e.g., Parikh & Guengerich, Biotechniques 24:428-431 (1998)). Complementary primers overlapping the site of change can be used to PCR amplify the whole plasmid in a mixture containing 500 mM dNTPs, 2 units of Pfu polymerase, 250 ng each of sense and antisense primers, and 200 ng of plasmid DNA comprising a sequence encoding Q3 SPARC deletion mutant polypeptide. The PCR desirably involves 18 cycles with an extension time of 2.5 minutes for each Kb of DNA. The PCR products can be treated with DpnI (which only digests the adenine-methylated plasmid DNA) and transformed into *Escherichia coli* DH5α cells. Transformants can be screened by restriction enzyme digestion for incorporation of the changes, which then can be confirmed by DNA sequence analysis.

The nucleic acid fragment encoding the mutagenized sequence can be isolated, e.g., by PCR amplification using 5' and 3' primers, preferably ones that terminate in further unique restriction sites, that flank the mutated nucleotide. Use of primers in this fashion results in an amplified sequence that is flanked by the unique restriction sites. The unique restriction sites can be used for further convenient subcloning of the fragment.

The invention further provides for a recombinant vector comprising the nucleic acid sequence encoding a, wherein, e.g., the vector further comprising a promoter controlling the expression of the Q3 SPARC deletion mutant polypeptide encoding nucleic acid sequences. In addition, the invention provides for a cell comprising the nucleic acid molecule of claim 3, wherein the cell is a prokaryotic cell or a eukaryotic cell. Methods of tissue culture are well known to the skilled artisan (see, e.g., Sambrook & Russell, Molecular Cloning: A Laboratory Manual, Cold Spring Harbor Laboratory Press, New York (2001), pp. 16.1-16.54). Accordingly, the invention further provides for method of making the polypeptide of claim 1 comprising: (a) transforming cells with a nucleic acid encoding the polypeptide of claim 1; (b) inducing the expression of the polypeptide by the transformed cells; and (c) purifying the polypeptide.

The invention further provides nucleic acid constructs comprising control elements and a Q3 SPARC deletion mutant polypeptide nucleic acid molecule described herein operatively linked to the control elements (e.g., a suitable promoter) for expression of a Q3 SPARC deletion mutant polypeptide or a polypeptide herein described with conservative amino acid changes in a Q3 SPARC deletion mutant polypeptide. Protein expression is dependent on the level of RNA transcription, which is in turn regulated by DNA signals. Similarly, translation of mRNA requires, at the very least, an AUG initiation codon, which is usually located within 10 to 100 nucleotides of the 5' end of the message. Sequences flanking the AUG initiator codon have been shown to influence its recognition by eukaryotic ribosomes, with conformity to a perfect Kozak consensus sequence resulting in optimal translation (see, e.g., Kozak, J. Molec. Biol. 196: 947-950 (1987)). Also, successful expression of an exogenous nucleic acid in a cell can require post-translational modification of a resultant protein. Accordingly, the invention provides plasmids encoding Q3 SPARC deletion mutant polypeptides wherein the vector is, e.g., pCDNA3.1 or a derivative thereof, and including but, not limited to, the pVT1000Q3 plasmid disclosed herein.

The nucleic acid molecules described herein preferably comprise a coding region operatively linked to a suitable promoter, which promoter is preferably functional in eukaryotic cells. Viral promoters, such as, without limitation, the RSV promoter and the adenovirus major late promoter can be used in the invention. Suitable non-viral promoters include, but are not limited to, the phosphoglycerokinase (PGK) promoter and the elongation factor 1$\alpha$ promoter. Non-viral promoters are desirably human promoters. Additional suitable genetic elements, many of which are known in the art, also can be ligated to, attached to, or inserted into the inventive nucleic acid and constructs to provide additional functions, level of expression, or pattern of expression. The native promoters for expression of the SPARC family genes also can be used, in which event they are preferably not used in the chromosome naturally encoding them unless modified by a process that substantially changes that chromosome. Such substantially changed chromosomes can include chromosomes transfected and altered by a retroviral vector or similar process. Alternatively, such substantially changed chromosomes can comprise an artificial chromosome such as a HAC, YAC, or BAC.

In addition, the nucleic acid molecules described herein may be operatively linked to enhancers to facilitate transcription. Enhancers are cis-acting elements of DNA that stimulate the transcription of adjacent genes. Examples of enhancers which confer a high level of transcription on linked genes in a number of different cell types from many species include, without limitation, the enhancers from SV40 and the RSV-LTR. Such enhancers can be combined with other enhancers which have cell type-specific effects, or any enhancer may be used alone.

To optimize protein production the inventive nucleic acid molecule can further comprise a polyadenylation site following the coding region of the nucleic acid molecule. Also, preferably all the proper transcription signals (and translation signals, where appropriate) will be correctly arranged such that the exogenous nucleic acid will be properly expressed in the cells into which it is introduced. If desired, the exogenous nucleic acid also can incorporate splice sites (i.e., splice acceptor and splice donor sites) to facilitate mRNA production while maintaining an inframe, full length transcript. Moreover, the inventive nucleic acid molecules can further comprise the appropriate sequences for processing, secretion, intracellular localization, and the like.

The nucleic acid molecules can be inserted into any suitable vector. Suitable vectors include, without limitation, viral vectors. Suitable viral vectors include, without limitation, retroviral vectors, alphaviral, vaccinial, adenoviral, adenoassociated viral, herpes viral, and fowl pox viral vectors. The vectors preferably have a native or engineered capacity to transform eukaryotic cells, e.g., CHO-K1 cells. Additionally, the vectors useful in the context of the invention can be "naked" nucleic acid vectors (i.e., vectors having little or no proteins, sugars, and/or lipids encapsulating them) such as plasmids or episomes, or the vectors can be complexed with other molecules. Other molecules that can be suitably combined with the inventive nucleic acids include without limitation viral coats, cationic lipids, liposomes, polyamines, gold particles, and targeting moieties such as ligands, receptors, or antibodies that target cellular molecules.

The nucleic acid molecules described herein can be transformed into any suitable cell, typically a eukaryotic cell, such as, e.g., CHO, HEK293, or BHK, desirably resulting in the expression of a Q3 SPARC deletion mutant polypeptide such as, e.g., polypeptide comprising of SEQ ID NO: 2 or a variant thereof as described herein. The cell can be cultured to provide for the expression of the nucleic acid molecule and, therefore, the production of the Q3 SPARC deletion mutant polypeptide such as, e.g., a polypeptide comprising the amino acid sequence of SEQ ID NO: 2 or a variant thereof as described herein.

Therefore, the invention provides for a cell transformed or transfected with an inventive nucleic acid molecule described herein. Means of transforming, or transfecting, cells with exogenous DNA molecules are well known in the art. For example, without limitation, a DNA molecule is introduced into a cell using standard transformation or transfection techniques well known in the art such as calcium-phosphate or DEAE-dextran-mediated transfection, protoblast fusion, electroporation, liposomes and direct microinjection (see, e.g., Sambrook & Russell, Molecular Cloning: A Laboratory Manual, Cold Spring Harbor Laboratory Press, New York (2001), pp. 1.1-1.162, 15.1-15.53, 16.1-16.54). A widely used method for transformation is transfection mediated by either calcium phosphate or DEAE-dextran. Depending on the cell type, up to 20% of a population of cultured cells can be transfected at any one time.

Another example of a transformation method is the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells, and the plasmid DNA is transferred to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA randomly integrated into the host chromosome.

Electroporation, the application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest.

Liposome transformation involves encapsulation of DNA and RNA within liposomes, followed by fusion of the liposomes with the cell membrane. In addition, DNA that is coated with a synthetic cationic lipid can be introduced into cells by fusion. Alternatively, linear and/or branched polyethylenimine (PEI) can be used in transfection.

Direct microinjection of a DNA molecule into nuclei has the advantage of not exposing the DNA molecule to cellular compartments such as low-pH endosomes. Microinjection is, therefore, used primarily as a method to establish lines of cells that carry integrated copies of the DNA of interest.

Such techniques can be used for both stable and transient tranformation of eukaryotic cells. The isolation of stably transformed cells requires the introduction of a selectable marker in conjunction with the transformation with the gene of interest. Such selectable markers include genes which confer resistance to neomycin as well as the HPRT gene in HPRT negative cells. Selection can require prolonged culture in selection media, at least for about 2-7 days, preferable for at least about 1-5 weeks (see, e.g., Sambrook & Russell, Molecular Cloning: A Laboratory Manual, Cold Spring Harbor Laboratory Press, New York (2001), pp. 16.1-16.54).

Nucleic acid sequences for use in the present invention may also be produced in part or in total by chemical synthesis, e.g. by the phosphoramidite method described by Beaucage, et al. (Tetra. Letts. 22: 1859-1862 (1987)), or the triester method (Matteucci et al., J. Am. Chem. Soc. 103: 3185 (1981)), which may be performed on commercial automated oligonucleotide synthesizers. A double-stranded fragment may be obtained from the single-stranded product of chemical synthesis either by synthesizing the complementary strand and annealing the strand together under appropriate conditions, or by synthesizing the complementary strand using DNA polymerase with an appropriate primer sequence.

Gene Therapy Gene therapy is a medical intervention that involves modifying the genetic material of living cells to fight disease. Gene therapy is being studied in clinical trials (research studies with humans) for many different types of cancer and for other diseases.

The invention further provides for an isolated nucleic acid molecule encoding a Q3 SPARC deletion mutant polypeptide suitable for use in "gene therapy" (see, e.g., Patil et al., AAPS J. 7(1):E61-77 (2005)). Suitable nucleic acid include, but are not limited to nucleic acids comprising SEQ ID NO: 3 or modifications and homologues thereof as described herein. One of the goals of gene therapy is to supply cells with altered genes, such as, e.g., an isolated nucleic acid molecule encoding a Q3 SPARC deletion mutant polypeptide. Gene therapy is also being studied as a way to change how a cell functions; for example, by stimulating immune system cells to attack cancer cells.

In general, a gene is delivered to the cell using a "vector" such as those disclosed herein. The most common types of vectors used in gene therapy are viruses. Viruses used as vectors in gene therapy are genetically disabled; they are unable to reproduce themselves. Most gene therapy clinical trials rely on mouse retroviruses to deliver the desired gene. Other viruses used as vectors include adenoviruses, adeno-associated viruses, poxviruses, and the herpes virus. Suitable viral gene therapy vectors and modes of their administration in vivo and ex vivo are know in the art.

Gene therapy can be done both ex vivo and in vivo. Typically, in ex vivo gene therapy clinical trials, cells from the patient's blood or bone marrow are removed and grown in the laboratory. The cells are exposed to the virus that is carrying the desired gene. The virus enters the cells, and the desired gene becomes part of the cells' DNA. The cells grow in the laboratory and are then returned to the patient by injection into a vein. In in vivo gene therapy, vectors such as, e.g., viruses or liposomes are used to deliver the desired gene to cells inside the patient's body.

A Q3 SPARC deletion mutant polypeptide can be expressed and purified from a recombinant host cell. Recombinant host cells may be prokaryotic or eukaryotic, including but not limited to bacteria such as *E. coli*, fungal cells such as yeast, insect cells including but, not limited to, *drosophila* and silkworm derived cell lines, and mammalian cells and cell lines. When expressing a Q3 SPARC deletion mutant polypeptide in a cell, e.g., a human cell, whether, in vitro or in vivo, the codons selected for such the polynucleotide encoding the Q3 SPARC can be optimized for a given cell type (i.e., species). Many techniques for codon optimization are known in the art (see, e.g., Jayaraj et al, Nucleic Acids Res. 33(9):3011-6 (2005); Fuglsang et al., Protein Expr. Purif. 31(2):247-9 (2003); Wu et al., "The Synthetic Gene Designer: a Flexible Web Platform to Explore Sequence Space of Synthetic Genes for Heterologous Expression," csbw, 2005 IEEE Computational Systems Bioinformatics Conference—Workshops (CSBW'05), pp. 258-259 (2005)).

In certain embodiments, when expressing and purifying a Q3 SPARC deletion mutant polypeptide, techniques for improving protein solubility are employed to prevent the formation of inclusion body (which are insoluble fractions), and therefore obtaining large quantities of the polypeptide. SPARC accumulated in inclusion bodies is an inactive-type SPARC not retaining its physiological activities.

Solubility of a purified Q3 SPARC deletion mutant polypeptide can be improved by methods known in the art. For example, solubility may also be improved by expressing a functional fragment, but not the full length Q3 SPARC deletion mutant polypeptide. In addition, to increase the solubility of an expressed protein (e.g., in *E. coli*), one can reduce the rate of protein synthesis by lowering the growth temperature, using a weaker promoter, using a lower copy number plasmid, lowering the inducer concentration, changing the growth medium as described in Georgiou & Valax (Current Opinion Biotechnol. 7:190-197 (1996)). This decreases the rate of protein synthesis and usually more soluble protein is obtained. One can also add prosthetic groups or co-factors which are essential for proper folding or for protein stability, or add buffer to control pH fluctuation in the medium during growth, or add 1% glucose to repress induction of the lac promoter by lactose, which is present in most rich media (such as LB, 2xYT). Polyols (e.g., sorbitol) and sucrose may also be added to the media because the increase in osmotic pressure caused by these additions leads to the accumulation of osmoprotectants in the cell, which stabilize the native protein structure. Ethanol, low molecular weight thiols and disulfides, and NaCl may be added. In addition, chaperones and/or foldases may be co-expressed with the desired polypeptide. Molecular chaperones promote the proper isomerization and cellular targeting by transiently interacting with folding intermediates. E. coli chaperone systems include but, are not limited to: GroES-GroEL, DnaK-DnaJ-GrpE, ClpB.

Foldases accelerate rate-limiting steps along the folding pathway. Three types of foldases play an important role: peptidyl prolyl cis/trans isomerases (PPI's), disulfide oxidoreductase (DsbA) and disulfide isomerase (DsbC), protein disulfide isomerase (PDI) which is an eukaryotic protein that catalyzes both protein cysteine oxidation and disulfide bond isomerization. Co-expression of one or more of these proteins with the target protein could lead to higher levels of soluble target protein.

A Q3 SPARC deletion mutant polypeptide can be produced as a fusion protein in order to improve its solubility and production. The fusion protein comprises a Q3 SPARC deletion mutant polypeptide and a second polypeptide fused together in frame. The second polypeptide may be a fusion partner known in the art to improve the solubility of the polypeptide to which it is fused, for example, NusA, bacterioferritin (BFR), GrpE, thioredoxin (TRX) and glutathione-S-transferase (GST). Novagen Inc. (Madison, Wis.) provides the pET 43.1 vector series which permit the formation of a NusA-target fusion. DsbA and DsbC have also shown positive effects on expression levels when used as a fusion partner, therefore can be used to fuse with a SPARC polypeptide for achieving higher solubility.

In one embodiment, a Q3 SPARC deletion mutant polypeptide is produced as a fusion polypeptide comprising the Q3 SPARC deletion mutant polypeptide and a fusion partner thioredoxin, as described in U.S. Pat. No. 6,387,664, hereby incorporated by reference in its entirety. The thioredoxin-SPARC fusion can be produced in E. coli as an easy-to-formulate, soluble protein in a large quantity without losing the physiological activities. Although U.S. Pat. No. 6,387,664 provides a fusion SPARC protein with SPARC fused to the C-terminus of thioredoxin, it is understood, for the purpose of the present invention, a Q3 SPARC deletion mutant polypeptide can be fused either to the N-tenninus or the C-terminus of a second polypeptide, so long as its sensitizing function is retained.

In addition to increase solubility, a fusion protein comprising a Q3 SPARC deletion mutant polypeptide can be constructed for the easy detection of the expression of the Q3 SPARC deletion mutant polypeptide in a cell. In one embodiment, the second polypeptide which fused to the Q3 SPARC deletion mutant polypeptide is a reporter polypeptide. The reporter polypeptide, when served for such detection purpose, does not have to be fused with the Q3 SPARC deletion mutant polypeptide. It may be encoded by the same polynucleotide (e.g., a vector) which also encodes the Q3 SPARC deletion mutant polypeptide and be co-introduced and co-expressed in a target cell.

Preferably, the reporter polypeptide used in the invention is an autofluorescent protein (e.g., GFP, EGFP). Autofluorescent proteins provide a ready assay for identification of expression of a polynucleotide (and the polypeptide product) of interest. Because the activity of the reporter polypeptide (and by inference its expression level) can be monitored quantitatively using a flow sorter, it is simple to assay many independent transfectants either sequentially or in bulk population. Cells with the best expression can then be screened for or selected from the population. This is useful when selecting a recombinant cell comprising a Q3 SPARC deletion mutant polypeptide or polynucleotide for sensitizing treatment according to the present invention.

Quantitative parameters such as mean fluorescence intensity and variance can be determined from the fluorescence intensity profile of the cell population (Shapiro, H., 1995, Practical Flow Cytometry, 217-228). Non-limiting examples of reporter molecules useful in the invention include luciferase (from firefly or other species), chloramphenicol acetyltransferase, β-galactosidase, green fluorescent protein (GFP), enhanced green fluorescent protein (EGFP), and dsRed.

Expression of the SPARC polypeptide (either by itself, or as a fusion protein) can also be directly determined by an immunoassay such as an ELISA (enzyme-linked immunoabsorbent assay) (see, e.g., U.S. Pat. Nos. 5,962,320; 6,187,307; and 6,194,205), Western blot, or by other methods routine in the art. The expression of a Q3 SPARC deletion mutant polypeptide can be indirectly detected by detecting the transcript of the protein (e.g., by hybridization analysis such as Northern blot or DNA Microarray, or by PCR).

In one embodiment, a polynucleotide encoding a second polypeptide is fused to a polynucleotide encoding a Q3 SPARC deletion mutant polypeptide through an intervening linker sequence which encodes for a linker polypeptide.

In another embodiment, the linker polypeptide comprises a protease cleavage site comprising a peptide bond which is hydrolyzable by a protease. As a result, the Q3 SPARC deletion mutant polypeptide can be separated from the second polypeptide after expression by proteolysis. The linker can comprise one or more additional amino acids on either side of the bond to which the catalytic site of the protease also binds (see, e.g., Schecter & Berger, Biochem. Biophys. Res. Commun. 27, 157-62 (1967)). Alternatively, the cleavage site of the linker can be separate from the recognition site of the protease and the two cleavage site and recognition site can be separated by one or more (e.g., two to four) amino acids. In one aspect, the linker comprises at least about 2, 3, 4, 5, 6, 7, 8, 9, about 10, about 20, about 30, about 40, about 50 or more amino acids. More preferably the linker is from about 5 to about 25 amino acids in length, and most preferably, the linker is from about 8 to about 15 amino acids in length.

Some proteases useful according to the invention are discussed in the following references: Hooper et al., Biochem. J. 321: 265-279 (1997); Werb, Cell 91: 439-442 (1997); Wolfsberg et al., J. Cell Biol. 131: 275-278 (1995); Murakami & Etlinger, Biochem. Biophys. Res. Comm. 146: 1249-1259 (1987); Berg et al., Biochem. J. 307: 313-326 (1995); Smyth and Trapani, Immunology Today 16: 202-206 (1995); Talanian et al., J. Biol. Chem. 272: 9677-9682 (1997); and Thornberry et al., J. Biol. Chem. 272: 17907-17911 (1997). Cell surface proteases also can be used with cleavable linkers according to the invention and include, but are not limited to: Aminopeptidase N; Puromycin sensitive aminopeptidase; Angiotensin converting enzyme; Pyroglutamyl peptidase II; Dipeptidyl peptidase IV; N-arginine dibasic convertase; Endopeptidase 24.15; Endopeptidase 24.16; Amyloid precursor protein secretases alpha, beta and gamma; Angiotensin converting enzyme secretase; TGF alpha secretase; TNF alpha secretase; FAS ligand secretase; TNF receptor-I and -II secretases; CD30 secretase; KL1 and KL2 secretases; IL6 receptor secretase; CD43, CD44 secretase; CD16-I and CD16-II secretases; L-selectin secretase; Folate receptor secretase; MMP 1,2, 3,7, 8,9, 10,11, 12,13, 14, and 15; Urokinase plasminogen activator; Tissue plasminogen activator; Plasmin; Thrombin; BMP-1 (procollagen C-peptidase); ADAM 1,2, 3,4, 5,6, 7,8, 9,10, and 11; and, Granzymes A, B, C, D, E, F, G, and H.

An alternative to relying on cell-associated proteases is to use a self-cleaving linker. For example, the foot and mouth disease virus (FMDV) 2A protease may be used as a linker. This is a short polypeptide of 17 amino acids that cleaves the polyprotein of FMDV at the 2A/2B junction. The sequence of the FMDV 2A propeptide is NFDLLKLAGDVESNPGP. Cleavage occurs at the C-terminus of the peptide at the final glycine-proline amino acid pair and is independent of the presence of other FMDV sequences and cleaves even in the presence of heterologous sequences.

Insertion of this sequence between two protein coding regions (i.e., between the Q3 SPARC deletion mutant polypeptide and the second polypeptide of a fusion protein according to the invention) results in the formation of a self-cleaving chimera which cleaves itself into a C-terminal fragment which carries the C-terminal proline of the 2A protease on its N-terminal end, and an N-terminal fragment that carries the rest of the 2A protease peptide on its C-terminus (see, e.g., de Felipe et al., Gene Therapy 6: 198-208 (1999)). Self-cleaving linkers and additional protease-linker combinations are described further in PCT Publication WO 01/20989, the entirety of which is incorporated by reference herein.

Polynucleotides encoding linker sequences described above can be cloned from sequences encoding the natural substrates of an appropriate protease or can be chemically synthesized using methods routine in the art.

Affinity chromatography employing SPARC ligands and/or anti-SPARC antibodies can also by used to purify SPARC polypeptides in accordance with the invention. Affinity chromatography can be used alone or in conjunction with ion-exchange, molecular sizing, or HPLC chromatographic techniques. Such chromatographic approach can be performed using columns or in batch formats. Such chromatographic purification methods are well known in the art.

The invention provides for the use of antibody raised against SPARC, in particular a Q3 SPARC deletion mutant polypeptide, as therapeutic agent against, or imaging agent for, diseases where SPARC plays a role. Antibodies can be tested for specificity of binding by comparing binding to appropriate antigen to binding to irrelevant antigen or antigen mixture under a given set of conditions. If the antibody binds to the appropriate antigen at least about 2 times, preferably at least about 5 times, more preferably at least about 7 times, and more preferably at least about 10 times more strongly than to irrelevant antigen, including, e.g., a wild type SPARC polypeptide, or antigen mixture then it is considered to be specific. In addition, the invention provides for an antibody against a SPARC polypeptide, such as, e.g., a Q3 SPARC deletion mutant polypeptide, wherein the antibody binds both Q3 SPARC deletion mutant polypeptides and wild type SPARC polypeptides but, wherein the antibody binds to a Q3 SPARC deletion mutant polypeptide at least about 2 times, preferably at least about 5 times, more preferably at least about 7 times, and more preferably at least about 10 times more strongly than to wild type SPARC polypeptides. Various methods of determining antibody binding strength are known to those of ordinary skill in the art (see, e.g., Harlow & Lane, Antibodies, A Laboratory Manual, Cold Spring Harbor (1988)).

Any suitable antibodies against a SPARC polypeptide, such as, e.g., a Q3 SPARC deletion mutant polypeptide, can be used in the inventive method, so long as the antibody exhibits specific binding to a SPARC polypeptide, such as, e.g., Q3 SPARC deletion mutant polypeptide. The antibody can either be monoclonal or polyclonal; and can be produced either through immunization of an animal or produced through recombinant DNA technology such as phage display and in vitro mutagenesis or synthesis of the variable regions of the antibody heavy and light chain genes. Polyclonal antibodies include, but are not limited to, human antibodies and humanized antibodies derived from animals such as avian (e.g, chicken), rodent (e.g., rat, mouse, hamster, guinea pig), cow, goat, sheep, rabbit and the like. Monoclonal antibody include antibody derived from a single clone of antibody producing cells including, but not limited to, human cells, and antibodies derived from the cells of other animal types, such as, for example, chicken, rabbit, rat, mouse, hamster, guinea pig, cow, goat, sheep, and the like. Synthetic antibody includes antibody produced using recombinant DNA means via genetic engineering of the variable regions of the heavy and light chain genes. Synthetic antibody also includes chemically synthesized antibody fragment with Q3 SPARC deletion mutant polypeptide polypeptide binding activity or antibody derived from phage display or similar technology. Methods of making antibodies are well known in the art (see, e.g., Harlow & Lane, Antibodies, A Laboratory Manual, Cold Spring Harbor, pp. 1-420 (1988)).

For human use, in order to avoid immunogenicity and an immune response, it is preferable to use humanized anti-Q3 SPARC deletion mutant polypeptide polypeptide antibody or suitable fragments such as Fc or Fab. Humanized antibody or fragments thereof are produced, for example, using one of the following established methods: (1) Humanized antibody can be constructed using human IgG backbone replacing the variable CDR region with that of antibody against SPARC, the heavy and light chain are independently expressed under separate promoters or coexpressed under one promoter with IRES sequence; (2) Humanized monoclonal antibody is raised against SPARC using mouse engineered to have human immune system; or (3) Humanized antibody against SPARC is raised using phagemid (M13, lambda coliphage, or any phage system capable of surface presentation). To construct the full length antibody, the variable region is transferred onto the CDR of both Heavy chain and Light chain. The coexpression of the Heavy chain and Light Chain in mammalian cells such as CHO, 293, or human myeloid cells results in full length antibody. Similarly, Fc or Fab fragments and single chain antibodies can be prepared using well established methods.

The antibody against a SPARC polypeptide, e.g., a Q3 SPARC deletion mutant polypeptide made in accordance with the invention, is also not limited to a whole antibody or fragment of the antibody retaining the binding site for the SPARC polypeptide, e.g., for a Q3 SPARC deletion mutant polypeptide (e.g., Fab and Fab2). The antibody is also not limited to any one class of antibody, e.g., IgM, IgA, IgG, IgE, IgD, and IgY. The antibody is also not limited to divalent antibody, monovalent, or chimeria with one valent for SPARC and another for an effector such tTF or ricin A. The humanized antibody is not limited to IgG. The same technologies can be used to generate all other classes of antibodies such as IgE, IgA, IgD, IgM, each has different ADCC and CDC activities appropriate to particular disease target. Functional fragment of the antibody can be generated by limited proteolysis. These fragments can be monovalent such as Fab' or divalent, such as Fab2. Fragments can also be synthesized as single chain scfv or diabodies in *E. coli*.

The invention also provides a method for destruction of SPARC expression tissues such as tumor and restenotic tissues via the complement fixation and/or recruitment of cell mediated immune response by anti-Q3 SPARC deletion mutant polypeptide antibody. In this case, like that of Rituxan—an anti-CD20 antibody, the effector moiety is the Fc fragment which can mediate either complement activation with direct destruction of SPARC expression cells or recruitment of immune cells to the SPARC expression tissue with resulting tissue destruction via cell mediate immune response.

The invention also provides a method for inhibition of SPARC activity using neutralizing antibody against SPARC, e.g. an anti-Q3 SPARC deletion mutant polypeptide polypeptide antibody. Neutralizing antibody has the ability to block the interaction of SPARC with its effectors in vivo, for example, the interaction of SPARC with cell surface component or the binding of SPARC to its natural ligands such as albumin, growth factors, and $Ca^{2+}$.

The invention provides a method for determining the response of a human or other mammalian tumor to anti-SPARC therapy (e.g., anti-Q3 SPARC deletion mutant polypeptide therapy). The method comprises (a) isolating a biological sample from the human, (b) detecting the expression of SPARC protein (including, e.g., a Q3 SPARC deletion mutant polypeptide) in the biological sample, and (c) quantifying the amount of SPARC protein in the biological sample. As anti-SPARC therapy relies on the binding of SPARC antibody to SPARC in disease tissue, the presence of SPARC in disease tissue is necessary for activity.

Any suitable chemotherapeutic agent can be used to couple (or conjugate) to a Q3 SPARC deletion mutant polypeptide or an antibody against a SPARC polypeptide, such as, e.g., a Q3 SPARC deletion mutant polypeptide, in the inventive method. Suitable chemotherapeutics include, but are not limited to, tyrosine kinase inhibitors (genistein), biologically active agents (TNF, of tTF), radionuclides ($^{131}I$, $^{90}Y$, $^{111}In$, $^{211}At$, $^{32}P$ and other known therapeutic radionuclides), adriamycin, ansamycin antibiotics, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, meplhalan, methotrexate, rapamycin (sirolimus) and derivatives, mitomycin, mitotane, mitoxantrone, nitrosurea, paclitaxel, pamidronate, pentostatin, plicamycin, procarbazine, rituximab, streptozocin, teniposide, thioguanine, thiotepa, taxanes, vinblastine, vincristine, vinorelbine, taxol, combretastatins, discodermolides, transplatinum, anti-vascular endothelial growth factor compounds ("anti-VEGFs"), anti-epidermal growth factor receptor compounds ("anti-EGFRs"), 5-fluorouracil, and the like. A dose of one or more chemotherapeutic agents can be administered according to the inventive method. The type and number of chemotherapeutic agents used in the inventive method will depend on the standard chemotherapeutic regimen for a particular tumor type. In other words, while a particular cancer may be treated routinely with a single chemotherapeutic agent, another may be treated routinely with a combination of chemotherapeutic agents.

The terms "treating," "treatment," "therapy," and "therapeutic treatment" as used herein refer to curative therapy, prophylactic therapy, or preventative therapy. An example of "preventative therapy" is the prevention or lessening the chance of a targeted disease (e.g., cancer or other proliferative disease) or related condition thereto. Those in need of treatment include those already with the disease or condition as well as those prone to have the disease or condition to be prevented. The terms "treating," "treatment," "therapy," and "therapeutic treatment" as used herein also describe the management and care of a mammal for the purpose of combating a disease, or related condition, and includes the administration of a composition to alleviate the symptoms, side effects, or other complications of the disease, condition. Therapeutic treatment for cancer includes, but is not limited to, surgery, chemotherapy, radiation therapy, gene therapy, and immunotherapy.

By "therapeutically effective amount" it is meant an amount that relieves (to some extent, as judged by a skilled medical practitioner) one or more symptoms of the disease or condition in a mammal. Additionally, by "therapeutically effective amount" is meant an amount that returns to normal, either partially or completely, physiological or biochemical parameters associated with or causative of a disease or condition. A clinician skilled in the art can determine the therapeutically effective amount of a composition in order to treat or prevent a particular disease condition, or disorder when it is administered, such as intravenously, subcutaneously, intraperitoneally, orally, or through inhalation. The precise amount of the composition required to be therapeutically effective will depend upon numerous factors, e.g., such as the specific activity of the active agent, the delivery device employed, physical characteristics of the agent, purpose for the administration, in addition to many patient specific considerations. The determination of amount of a composition that must be administered to be therapeutically effective is routine in the art and within the skill of an ordinarily skilled clinician.

As used herein, the term "agent" or "drug" or "therapeutic agent" refers to a chemical compound, a mixture of chemical compounds, a biological macromolecule, or an extract made from biological materials such as bacteria, plants, fungi, or animal (particularly mammalian) cells or tissues that are suspected of having therapeutic properties. The agent or drug may be purified, substantially purified or partially purified. An "agent", according to the present invention, also includes a radiation therapy agent.

As used herein, the term "toxin" refers to a poisonous substance that is a specific product of the metabolic activities of a living organism including bacterial, plant, and other toxins, such as, e.g., diphtheria toxin, *pseudomonas* exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restrictocin (a ribosome inactivating protein produced by *Aspergillus restrictus*) or saporin (a ribosome inactivating protein from *Saponaria officinalis*).

As used herein, the term "proliferative disease" refers to disease characterized by cellular proliferation (e.g., mitosis) including both clonal proliferations (e.g., cancer) and polyclonal proliferations (e.g., hyperplasias; including but, not limited, to endometriosis, endometrial hyperplasia, benign prostatic hyperplasia (BPH)).

As used herein biological molecules are molecules produced by the metabolic activities of a living organism that have biological activities such as, e.g., cytokines interleukins, TNF, or tissue factor (TF). As used herein biologic molecules include other molecules composed of subunits normally found in living cells or their analogs such RNA that can have biologic activities such as, e.g., anti-sense RNA, RNAi, ribozymes, inhibitory peptide-nucleic acids, and the like.

Methods for coupling or conjugation of suitable therapeutics, chemotherapeutics, radionuclides, polypeptides, and the like to antibodies or fragments thereof are well described in the art. For example, The invention provides for Q3 SPARC deletion mutant polypeptide or anti-Q3 SPARC deletion mutant polypeptide antibodies conjugates, such as, e.g., SPARC-radionuclide, SPARC-drug, SPARC-immunomodulator or SPARC-toxin conjugates. Any suitable method can be used in accordance with the invention to form the SPARC conjugates. For example, without limitation, free amino groups in SPARC proteins, such the epsilon-amino group of lysine, can be conjugated with reagents such as carodiimides or heterobiofunctional agents. Alternatively, e.g., SPARC suflhydryl groups can be used for conjugation. In addition, sugar moieties bound to SPARC glycoproteins or an anti-SPARC antibodies, e.g., an anti-Q3 SPARC deletion mutant polypeptide antibodies can be oxidized to form aldehydes groups useful in a number of coupling procedures known in the art. The conjugates formed in accordance with the invention can be stable in vivo or labile, such as enzymatically degradeable tetrapeptide linakages or acid-labile cis-aconityl or hydrazone linkages.

The invention also provides for SPARC-carrier-therapeutic agent molecule or anti-SPARC polypeptide, such as, e.g., anti-Q3 SPARC deletion mutant polypeptide antibody, conjugates such as, e.g., conjugates of a SPARC and a drug with carriers. Suitable carriers for use in accordance with the invention include, without limitation, dextran, human serum albumin, and hydroxypropylmethacrylamide. Further, the invention provides for SPARC or anti-SPARC antibody, e.g., an anti-Q3 SPARC deletion mutant polypeptide antibody, coated drug carrier structures such as, e.g., liposomes.

The invention provides for SPARC molecules, including SPARC polypeptides and proteins and anti-SPARC antibodies, such as, e.g., ant-Q3 SPARC deletion mutant polypeptide antibodies, conjugated to polyethylene glycol (PEG). PEG conjugation can increase the circulating half-life of a protein, reduce the protein's immunogenicity and antigenicity, and improve the bioactivity. Any suitable method of conjugation can be used, including but not limited to, e.g., reacting methoxy-PEG with a SPARC protein's available amino groups or other reactive sites such as, e.g., histidines or cysteines. In addition, recombinant DNA approaches may be used to add amino acids with PEG-reactive groups to the inventive SPARC molecules and antibodies. PEG can be processed prior to reacting it with the inventive SPARC protein, e.g., linker groups may be added to the PEG. Further, releasible and hybrid PEG-ylation strategies may be used in accordance with the invention, such as, e.g., the PEG-ylation of SPARC such that the PEG molecules added to certain sites in the SPARC molecule are released in vivo. Such PEG conjugation methods are known in the art (See, e.g., Greenwald et al., Adv. Drug Delivery Rev. 55:217-250 (2003)).

In addition, the invention provides for SPARC fusion proteins, including, for example without limitation, SPARC sequences are fused upstream or downstream of diagnostically useful protein domains (such as hapten, GFP), immunologically active protein domains (e.g., TF or TNF) or toxin domains.

The invention also provides for method of the use of diagnostic agents coupled or conjugated to the SPARC recognition groups, such as the antibodies, including anti-Q3 SPARC deletion mutant polypeptide antibodies, or fragments thereof, as described above. The diagnostic agents include radioisotopes or radionuclides, MRI contrast agents, X-ray contrast agents, ultrasound contrast agents and PET contrast agents. Methods utilized for conjugation are known in the art.

The expression of SPARC protein in the sample can be detected and quantified by any suitable method known in the art. Suitable methods of protein detection and quantification include Western blot, enzyme-linked immunosorbent assay (ELISA), silver staining, the BCA assay (Smith et al., Anal. Biochem. 150, 76-85 (1985)), the Lowry protein assay (described in, e.g., Lowry et al., J. Biol. Chem. 193, 265-275 (1951)), which is a calorimetric assay based on protein-copper complexes, and the Bradford protein assay (described in, e.g., Bradford et al., Anal. Biochem. 72, 248 (1976)), which depends upon the change in absorbance in Coomassie Blue G-250 upon protein binding. Tumor biopsy can be analyzed by any of the preceding methods or it can be analyzed by immunohistochemistry using an anti-SPARC antibody, e.g., an anti-Q3 SPARC deletion mutant polypeptide anbody, (either monoclonal or polyclonal) in conjunction with appropriate visualization system (i.e., HRP substrate and HRP-conjugated secondary antibody).

The types of tumor to be detected, sensitized, and/or treated in accordance with the invention are generally those found in humans and other mammals. The tumors can be the result of inoculation as well, such as in laboratory animals. Many types and forms of tumors are encountered in the human and other animal condition, and there is no intention to limit the application of the methods of the present to any particular tumor type or variety. Tumors, as is known, include an abnormal mass of tissue that results from uncontrolled and progressive cell division, and is also typically known as a "neoplasm." The inventive methods are useful for tumor cells and associated stromal cells, solid tumors and tumors associated with soft tissue, such as, soft tissue sarcoma, for example, in a human. The tumor or cancer can be located in the oral cavity and pharynx, the digestive system, the respiratory system, bones and joints (e.g., bony metastases), soft tissue, the skin (e.g., melanoma), breast, the genital system, the urinary system, the eye and orbit, the brain and central nervous system (e.g., glioma), or the endocrine system (e.g., thyroid) and is not necessarily the primary tumor or cancer. Tissues associated with the oral cavity include, but are not limited to, the tongue and tissues of the mouth. Cancer can arise in tissues of the digestive system including, for example, the esophagus, stomach, small intestine, colon, rectum, anus, liver, gall bladder, and pancreas. Cancers of the respiratory system can affect the larynx, lung, and bronchus and include, for example, non-small cell lung carcinoma. Tumors can arise in the uterine cervix, uterine corpus, ovary vulva, vagina, prostate, testis, and penis, which make up the male and female genital systems, and the urinary bladder, kidney, renal pelvis, and ureter, which comprise the urinary system. The tumor or cancer can be located in the head and/or neck (e.g., laryngeal cancer and parathyroid cancer). The tumor or cancer also can be located in the hematopoietic system or lymphoid system, and include, for example, lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like). Preferably, the tumor is located in the bladder, liver, ovary, kidney, gut, brain, or breast.

The invention further provides for a method of sensitizing a disease to a treatment comprising administering a Q3 SPARC deletion mutant polypeptide and a pharmaceutically acceptable carrier to a patient. Suitable such diseases in need of sensitization, include, without limitation, therapy-resistant (e.g., chemotherapy or radiation therapy-resistant) cancers. As used herein, the term "sensitizing" refers to an increased sensitivity or reduce the resistance of a cancer sample or a mammal responding to a therapeutic treatment. An increased sensitivity or a reduced sensitivity to a therapeutic treatment is measured according to a known method in the art for the particular treatment and methods described herein below, including, but not limited to, cell proliferative assays or cell death assays. The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is about 25% or more, for example, about 30%, about 40%, about 50%, about 60%, about 70%, about 80%, or more, to about 2-fold, about 3-fold, about 4-fold, about 5-fold, about 10-fold, about 15-fold, about 20-fold or more, compared to treatment sensitivity or resistance in the absence of such composition or method. The determination of sensitivity or resistance to a therapeutic treatment is routine in the art and within the skill of an ordinarily skilled clinician. As such, using SPARC for disease sensitization according the invention can further comprise administering one or more non-SPARC therapeutic agents, e.g., combination chemotherapy or other drugs.

The invention also provides a method for delivering a chemotherapeutic agent to a tumor in a mammal. The method comprises administering to a human or other mammal a therapeutically effective amount of a delivery agent, such as a pharmaceutical composition, wherein the delivery agent (e.g., pharmaceutical composition) comprises the chemotherapeutic agent coupled to the Q3 SPARC deletion mutant polypeptide or anti-Q3 SPARC deletion mutant polypeptide antibody. For example, the chemotherapeutic agent can be coupled to a SPARC recognition group such as an antibody recognizing SPARC protein, or the SPARC antibody alone. Pharmaceutical compositions preferably include the chemotherapeutic agent coupled to the SPARC recognition group and a pharmaceutically acceptable carrier. Descriptions of the chemotherapeutic agent, tumor, mammal, and components thereof, set forth above in connection with other embodiments of the invention also are applicable to those same aspects of the aforesaid method of delivering a chemotherapeutic agent to a tumor.

In another preferred embodiment, the invention also provides a method for delivering a pharmaceutically active agent (such as, e.g., anti-SPARC or anti-Q3 SPARC deletion mutant polypeptide antibody alone or chemotherapeutic agent coupled or conjugated to anti-SPARC or anti-Q3 SPARC deletion mutant polypeptide antibody and the like) to a site of disease that is characterized by overexpression of SPARC in a human, or other animal that expresses such protein or marker. Such diseases include abnormal conditions of proliferation, tissue remodeling, hyperplasia, and exaggerated wound healing in bodily tissue (e.g., soft tissue, connective tissue, bone, solid organs, blood vessel and the like). Examples of diseases that are treatable or diagnosed by administering a pharmaceutical composition comprising Q3 SPARC deletion mutant polypeptide or anti-SPARC polypeptide antibody, such as, e.g., ant-Q3 SPARC deletion mutant polypeptide antibody therapy, include cancer, diabetic or other retinopathy, inflammation, arthritis, atherosclerosis, renal mesangial disease, restenosis in blood vessels, artificial blood vessel grafts, or devices, and the like.

The inventive method comprises administering to a mammal afflicted with a disease characterized by over-expression of SPARC a therapeutically effective amount of a pharmaceutical composition comprising a chemotherapeutic agent or radioactive element coupled to a Q3 SPARC deletion mutant polypeptide or an anti-SPARC polypeptide, such as, e.g., an anti-Q3 SPARC deletion mutant polypeptide antibody. The chemotherapeutic or radioactive agent can be coupled to the antibody recognizing SPARC using any suitable method. Preferably, the chemotherapeutic agent can be chemically coupled to the compound via covalent bonds including, for example, disulfide bonds.

For use in vivo, the Q3 SPARC deletion mutant polypeptide or anti-SPARC polypeptide antibody, such as, e.g., anti-Q3 SPARC deletion mutant polypeptide antibody, coupled or conjugated to a therapeutic agent desirably is formulated into a pharmaceutical composition comprising a physiologically acceptable carrier. Any suitable physiologically acceptable carrier can be used within the context of the invention, and such carriers are well known in the art.

The carrier typically will be liquid, but also can be solid, or a combination of liquid and solid components. The carrier desirably is physiologically acceptable (e.g., a pharmaceutically or pharmacologically acceptable) carrier (e.g., excipient or diluent). Physiologically acceptable carriers are well known and are readily available. The choice of carrier will be determined, at least in part, by the location of the target tissue and/or cells, and the particular method used to administer the composition.

Typically, such compositions can be prepared as injectables, either as liquid solutions or suspensions; solid forms suitable for using to prepare solutions or suspensions upon the addition of a liquid prior to injection can also be prepared; and the preparations can also be emulsified. The pharmaceutical formulations suitable for injectable use include sterile aqueous solutions or dispersions; formulations containing known protein stabilizers and lyoprotectants, formulations including sesame oil, peanut oil or aqueous propylene glycol, and sterile powders for the extemporaneous preparation of sterile injectable solutions or dispersions. In all cases the formulation must be sterile and must be fluid to the extent that easy syringability exists. It must be stable under the conditions of manufacture and storage and must be preserved against the contaminating action of microorganisms, such as bacteria and fungi. Solutions of the active compounds as free base or pharmacologically acceptable salts can be prepared in water suitably mixed with a surfactant, such as hydroxycellulose. Dispersions can also be prepared in glycerol, liquid polyethylene glycols, and mixtures thereof and in oils. Under ordinary conditions of storage and use, these preparations contain a preservative to prevent the growth of microorganisms.

The Q3 SPARC deletion mutant polypeptide or anti-SPARC, such as, e.g., anti-Q3 SPARC deletion mutant polypeptide, therapy can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such as organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The composition can further comprise any other suitable components, especially for enhancing the stability of the composition and/or its end-use. Accordingly, there is a wide variety of suitable formulations of the composition of the invention. The following formulations and methods are merely exemplary and are in no way limiting.

Formulations suitable for administration via inhalation include aerosol formulations. The aerosol formulations can be placed into pressurized acceptable propellants, such as dichlorodifluoromethane, propane, nitrogen, and the like. They also can be formulated as non-pressurized preparations, for delivery from a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described. In a preferred embodiment of the invention, the Q3 SPARC deletion mutant polypeptide or anti-SPARC, such as, e.g., anti-Q3 SPARC deletion mutant polypeptide therapy is formulated for injection (e.g., parenteral administration). In this regard, the formulation desirably is suitable for intratumoral administration, but also can be formulated for intravenous injection, intraperitoneal injection, subcutaneous injection, and the like.

Formulations suitable for anal administration can be prepared as suppositories by mixing the active ingredient with a variety of bases such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

In addition, the composition of the invention can comprise additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the pharmaceutical composition and physiological distress.

The invention further provides for a method of classifying a disease comprising detecting a SPARC polypeptide with a deletion of the glutamine corresponding to amino acid position 20 in SEQ ID NO: 1. This classification can, for example, without limitation, indicate the presence of a disease, provide information on the stage of the disease, be informative of the prognosis for a given patient or predict the response to therapy. Suitable diseases include, without limitation, diseases involving neoangiogenesis (e.g, cancer or retinopathies) or proliferative diseases (e.g., cancer, benign tumors, glomerulonephropathies, atherosclerosis, and proliferative vascular restenosis). Suitable SPARC polypeptides include, without limitation, wherein the mutant SPARC polypeptide detected comprises the amino acid sequence of SEQ ID NO: 2.

Any suitable biological sample can be isolated from the mammal in the context of the inventive method and used for polypeptide and/or nucleic acid analysis. Preferably, the biological sample is isolated from the tumor, such as by a tumor biopsy. The biological sample is isolated from the mammal using methods known in the art. Alternatively, the biological sample can be isolated from a bodily fluid of the mammal, including, for example, cerebrospinal fluid, blood, plasma, serum, or urine. In particular, many protein purification techniques are known in the art (see, e.g., Harlow & Lane, Antibodies, A Laboratory Manual, Cold Spring Harbor, pp. 421-696 (1988)).

Any suitable method for the detection of a SPARC polypeptide with a deletion of the glutamine at corresponding to amino acid position 20 in SEQ ID NO: 1. can be used in accordance with the invention including, but not limited to, the use of anti-Q3 SPARC deletion mutant antibodies (e.g., Western blot, ELISA), the use of SPARC-specific binding proteins (e.g., radiolabel SPARC ligands, ELISA-like assays) or direct sequencing of partially purified or purified SPARC polypeptides (e.g., Sanger sequencing, HPLC peptide mapping and Edman degradation, mass spectrometry techniques, enzymatic degradations) (see, e.g., Harlow & Lane, Antibodies, A Laboratory Manual, Cold Spring Harbor, pp. 421-696 (1988); Kirkpatrick et al., Nature Cell Biol. 7(8):750-7 (2005); Tomita et al., J. Biol. Chem. 279(52):54161-72 (2004)).

The invention also provides for a method of classifying a disease comprising detecting a method of classifying a disease comprising detecting a nucleic acid encoding a SPARC polypeptide with a deletion of the glutamine at the position corresponding to amino acid position 20 of SEQ ID NO: 1, including wherein the nucleic acid is DNA or RNA. Further, the invention provides for a method of classifying a disease including, without limitation, wherein the mutant SPARC nucleic acid detected comprises the nucleic sequence of SEQ ID NO: 3. This classification can, for example, without limitation, indicate the presence of a disease, provide information on the stage of the disease, be informative of the prognosis for a given patient or predict the response to therapy. Suitable diseases include, without limitation, diseases involving neoangiogenesis (e.g, cancer or retinopathies) or proliferative diseases (e.g., cancer, benign tumors, glomerulonephropathies, atherosclerosis, and proliferative vascular restenosis).

Any suitable method can be using in accordance with the invention for the detection of a nucleic acid encoding a SPARC polypeptide with a deletion of the glutamine at the position corresponding to amino acid position 20 of SEQ ID NO: 1.

Nucleic acid sequence information may be obtained from a biological sample containing genetic material in numerous different ways, particularly, nucleic acids (genetic material) containing the sequence or sequences of interest. Many methods are known in the art for extracting nucleic acids from biological samples. There are many known methods for the separate or simultaneous isolation of DNA and RNA from biological samples. Typically, DNA may be isolated from a biological sample when first the sample is lysed and then the DNA is isolated from the lysate according to any one of a variety of multi-step protocols, which can take varying lengths of time. DNA isolation methods may involve the use of phenol (see, e.g., Sambrook & Russell, Molecular Cloning: A Laboratory Manual, Cold Spring Harbor Laboratory Press, New York (2001), pp. 6.1-6.62). For example, a biological sample is lysed in a detergent solution and the protein component of the lysate is digested with proteinase for 12-18 hours. Next, the lysate is extracted with phenol to remove most of the cellular components, and the remaining aqueous phase is processed further to isolate DNA. In another method, described in van Ness et al. (U.S. Pat. No. 5,130,423), non-corrosive phenol derivatives are used for the isolation of nucleic acids, resulting in a preparation that is a mix of RNA and DNA.

Other methods for DNA isolation utilize non-corrosive chaotropic agents. These methods, which are based on the use of guanidine salts, urea and sodium iodide, involve lysis of a biological sample in a chaotropic aqueous solution and subsequent precipitation of the crude DNA fraction with a lower alcohol (see, e.g., Analects, (1994) Vol 22, No. 4, Pharmacia Biotech; U.S. Pat. No. 5,128,247). Numerous other methods are known in the art to isolate both RNA and DNA, such as the one described by Chomczynski (U.S. Pat. No. 5,945,515), whereby genetic material can be extracted efficiently in as little as twenty minutes.

Once a subject's nucleic acid has been obtained from the subject it may then be further analyzed to detect or determine the presence or absence of one or more polymorphisms or mutations in the sequence of interest, provided that the genetic material obtained contains the sequence of interest. Particularly, a person can detect a nucleic acid sequence encoding a SPARC polypeptide comprising an amino acid sequence wherein the glutamine corresponding to amino acid 20 in SEQ ID NO: 1 is deleted. The sequence of interest may also include other mutations, or may also contain some of the sequence surrounding the mutation of interest.

Detection or determination of a nucleotide identity, or the presence of one or more single nucleotide polymorphism(s) (SNP typing), may be accomplished by any one of a number methods or assays known in the art. Many DNA typing methodologies are useful detection of SNPs including but, not limited to, sequence-specific hybridization, primer extension, oligonucleotide ligation, and invasive cleavage methods. Suitable reactions can occur in solution or on a solid support such as a glass slide, a chip, a bead, and the like.

Sequence-specific hybridization involves a hybridization probe, which is capable of distinguishing between two DNA targets differing at one nucleotide position by hybridization. In one approach, "Molecular beacons," the hybridization probe has 3' and 5' reporter and quencher molecules and 3' and 5' sequences which are complementary such that absent an adequate binding target for the intervening sequence the probe will form a hairpin loop. The hairpin loop keeps the reporter and quencher in close proximity resulting in quenching of the fluorophor which reduces fluorescence emissions. Upon hybridization to the target the fluorophor and the quencher are sufficiently separated to allow fluorescence to be emitted from the fluorophor. Primer extension reactions (i.e. mini sequencing, nucleotide-specific extensions, or simple PCR amplification) can also be useful in sequence discrimination reactions.

Oligonucleotide ligation assays require two sequence-specific probes and one common ligation probe per SNP. The common ligation probe hybridizes adjacent to a sequence-specific probe and when there is a perfect match of the appropriate sequence-specific probe, the ligase joins both the sequence-specific and the common probes.

Invasive cleavage method requires an oligonucleotide called an "Invader®" (Third Wave Technologies) probe and sequence-specific probes to anneal to the target DNA with an overlap of one nucleotide. When the sequence-specific probe is complementary to the polymorphic base, overlaps of the 3' end of the invader oligonucleotide form a structure that is recognized and cleaved by a Flap endonuclease releasing the 5' arm of the allele specific probe.

5' exonuclease activity or "TaqMan®" assay (Applied Biosystems) is based on the 5' nuclease activity of Taq polymerase that displaces and cleaves the oligonucleotide probes hybridized to the target DNA generating a fluorescent signal. It is necessary to have two probes that differ at the polymorphic site wherein one probe is complementary to the 'normal' sequence and the other to the mutation of interest. These probes have different fluorescent dyes attached to the 5' end and a quencher attached to the 3' end when the probes are intact the quencher interacts with the fluorophor by fluorescence resonance energy transfer (FRET) to quench the fluorescence of the probe. During the PCR annealing step the hybridization probes hybridize to target DNA. In the extension step the 5' fluorescent dye is cleaved by the 5' nuclease activity of Taq polymerase, leading to an increase in fluorescence of the reporter dye. Mismatched probes are displaced without fragmentation. The presence of a mutation in a sample is determined by measuring the signal intensity of the two different dyes.

In addition, there are numerous other methods for sequence discrimination and detection such as arrayed primer extension mini sequencing, tag microarrays and sequence-specific extension could be performed on a microarray. One such array based genotyping platform is the microsphere based the "tag-it" high throughput genotyping array (Bortolin et al., Clinical Chemistry 50(11): 2028-36 (2004)).

Mutation detection methods can also include but, are not limited to the following:

A Restriction Fragment Length Polymorphism (RFLP) strategy—An RFLP gel-based analysis can be used to indicate the presence or absence of a specific mutation at polymorphic sites within a gene based on the presence or absence of a restriction site;

Sequencing—For example, the Maxam-Gilbert technique for sequencing (Maxam & Gilbert, Proc. Natl. Acad. Sci. USA 74(4):560-564 (1977)) or the dideoxy method of sequencing was published by Sanger et al. (Proc. Natl. Acad. Sci. USA 74(12):5463-5467(1977)). In addition, RNA sequencing methods are also known. For example, reverse transcriptase with dideoxynucleotides have been used to sequence encephalomyocarditis virus RNA (Zimmern & Kaesberg, Proc. Natl. Acad. Sci. USA 75(9):4257-4261 (1978)). Mills and Kramer (Proc. Natl. Acad. Sci. USA (1979) 76(5):2232-2235) describe the use of Qβ replicase and the nucleotide analog inosine for sequencing RNA in a chain-termination mechanism. Direct chemical methods for sequencing RNA are also known (e.g., Peattie, Proc. Natl. Acad. Sci. USA 76(4):1760-1764 (1979)). Nucleic acid sequences can also be read by stimulating the natural fluoresce of a cleaved nucleotide with a laser while the single nucleotide is contained in a fluorescence enhancing matrix (U.S. Pat. No. 5,674,743);

Hybridization methods for the identification of single nucleotide polymorphisms or other mutations involving a few nucleotides are described in the U.S. Pat. Nos. 6,270,961 & 6,025,136;

A template-directed dye-terminator incorporation with fluorescent polarization-detection (TDI-FP) method is described by Freeman et al. (J. Mol. Diagnostics 4(4):209-215 (2002));

Oligonucleotide ligation assay (OLA) is based on ligation of probe and detector oligonucleotides annealed to a polymerase chain reaction amplicon strand with detection by an enzyme immunoassay (see e.g., Villahermosa, J. Hum. Virol. 4(5):238-48 (2001));

Ligation-Rolling Circle Amplification (L-RCA) has also been successfully used for genotyping single nucleotide polymorphisms as described by Qi et al. (Nucleic Acids Res. 29(22):E116(2001));

5' nuclease assay has also been successfully used for genotyping single nucleotide polymorphisms (Aydin et al., Biotechniques (4):920-2, 924, 926-8 (2001));

Polymerase proofreading methods are used to determine SNPs identities, as described in PCT Publication WO 01/81631;

Detection of single base pair DNA mutations by enzyme-amplified electronic transduction is described in Patolsky et al., Nature Biotech. (2001) 19(3):253-257 (2001);

Gene chip technologies are also known for single nucleotide polymorphism discrimination whereby numerous polymorphisms may be tested for simultaneously on a single array (See e.g., Gilles et al. Nat. Biotechnology 17(4):365-70 (1999));

Matrix Assisted Laser Desorption Ionization-Time Of Flight (MALDI-TOF) mass spectroscopy is also useful in the genotyping single nucleotide polymorphisms through the analysis of microsequencing products (See, e.g., Haff & Smirnov, Nucleic Acids Res. 25(18):3749-50 (1997)).

Sequence-specific PCR methods have also been successfully used for genotyping single nucleotide polymorphisms (Hawkins et al., Hum. Mutat. (2002) 19(5):543-553). The invention, therefore, provides for a method, wherein the nucleic acid encoding a Q3 SPARC deletion mutant polypeptide is detected using a method comprising the polymerase chain reaction (PCR). Further, the invention provides for a method, wherein mutant and non-mutant SPARC nucleic acids are detected using a method comprising PCR, wherein one or more forward primers selected from primers comprising the sequences of SEQ ID NOS: 7-9 and a reverse primer comprising the sequence of SEQ ID NO: 10.

Alternatively, if a subject's genetic sequence data is already known, then obtaining may involve retrieval of the subject's nucleic acid sequence data from a database, followed by determining or detecting the identity of a nucleic acid or genotype at a polymorphism site by reading the subject's nucleic acid sequence at the polymorphic site.

The invention also provides for a means of transporting the therapeutic composition across the endothelial barrier from the blood vessel into the tumor interstitium. The main hurdle in antibody therapy and chemotherapy is the translocation across the endothelial barrier into tumor interstitium. Albumin utilizes the albumin receptor transport mechanism to cross the endothelial barrier. This transport mechanism may be the same as those reported by the literature (gp60 and albondin) or by other mechanisms. The therapeutic agent piggy backed onto albumin exhibited enhanced tumoral uptake (Example—ABI-007 tumor uptake and transcytosis). Enhanced translocation across the endothelial barrier can be achieved using the physiological albumin transport mechanism.

For small molecules, modifications can be made so that the drug affinity for albumin is increased. For formulations of small molecules, solvent which prevents the binding of the drug to albumin can be removed. Alternatively, the small molecule could linked to albumin, antibody against albumin, fragments therof or ligands for albumin-receptor such as described below.

For biologic molecules such as proteins, antibodies and fragments, it is possible to engineer the biologics with an albumin binding peptide such that the biologics will exhibit affinity for albumin. The peptide can either be albumin binding sequence, antibody or antibody fragment against albumin, antibody or antibody fragment against albumin carriers such as gp60/albondin/scavenger receptor/or TGF-beta receptor, or antibody to any of the proteins found in the caveolae—the transporter of albumin. The invention also contemplates an antibody or suitable fragment thereof prepared as a chimera with one valence for SPARC and another valence for an effector of transendothelial transport such as gp60/albondin/scavenger receptor/or TGF-beta receptor, or against any of the proteins found in the caveolae of the endothelial cell.

The following examples further illustrate the invention but, of course, should not be construed as in any way limiting its scope.

EXAMPLE 1

This example illustrates the co-localization of SPARC with albumin in an MX-1 tumor xenograft.

Paclitaxel albumin nanoparticles (Abraxane, ABX or ABI-007) have been shown to have an improved response rate over Taxol (TAX) in a Phase 3 metastatic breast cancer trial (33% vs. 19%, $p<0.0001$) (see, e.g., O'Shaughnessy, SABCS 2003). Albumin-mediated transendothelial transport of paclitaxel (P) and increased intratumoral accumulation of paclitaxel for ABX versus TAX was demonstrated recently (see, e.g., Desai, SABCS 2003). Albumin binds to SPARC (see, e.g., Schnitzer, J. Biol. Chem. 269:6072-82 (1994)).

The MX-1 tumor cell line is derived from a human breast cancer. Serial cryosections of human MX-1 tumor xenograft, human primary breast tumor tissues (n=141), and normal human breast tissue (n=115) were immunostained and scored (0-4) for albumin, SPARC (using anti-SPARC antibody), and caveolin-1 staining. Cultured MX-1 cells also were immunostained for SPARC. Paclitaxel albumin nanoparticles (Abraxane, ABX or ABI-007) and Taxol (TAX) were prepared with radioactive paclitaxel (P) (20 mg/kg IV), and were used to determine the biodistribution of paclitaxel in normal tissues of athymic mice.

Albumin staining in the MX-1 tumor was focal and co-localized with SPARC (FIG. 1). Caveolin-1 staining confirmed that blood vessel density in albumin-containing areas was no different from albumin-free areas. SPARC expression by MX-1 cultured cells was confirmed by positive staining with anti-SPARC antibody. Paclitaxel accumulation in normal tissues (SPARC negative) was significantly lower for ABX as compared to TAX ($p<0.004$) for 7/10 tissues. 46% of the human primary breast tumors exhibited strong SPARC staining (score >2), as compared to 1% for normal tissues ($p<0.0001$). In a subset of 50 tumor tissues, SPARC expression did not correlate with staging, ER status, or PgR status; however, there was trend for high SPARC expression among p53-negative tumors.

The co-localization of albumin and SPARC suggests that SPARC, by its albumin binding activity, may behave as an intratumoral target for albumin binding in breast tumors. As transport of paclitaxel in ABX is dependent on albumin (see, e.g., Desai SABCS, 2003), this may explain the improved tumor accumulation of ABX as compared to TAX. ABX accumulation in normal tissues was lower than for TAX, consistent with lack of SPARC expression in normal tissues. Screening of patients for SPARC allows for the identification of patients more responsive to ABX. The presence of SPARC in these tumors allows for targeting and therapy using anti-SPARC antibody.

EXAMPLE 2

This example illustrates endothelial receptor (gp60)-mediated caveolar transcytosis of paclitaxel albumin nanoparticles (ABI-007).

Paclitaxel (P) albumin nanoparticles (Abraxane, ABX or ABI-007) demonstrated improved response rate over Taxol in a phase III metastatic breast cancer trial (33% vs 19%, p<0.0001) (SABCS, O'Shaughnessy et al, 2003). Cremophor in Taxol (TAX) entraps P in micelles in plasma, reducing the paclitaxel available for cellular partitioning (see, e.g., Sparreboom et al., *Cancer. Res.*, 59, 1454 (1999)). Studies in athymic mice have shown 30-40% higher intratumor paclitaxel concentrations with ABX as compared to equal doses of TAX (SABCS, Desai et al, 2003). Albumin is transported across endothelial cells (EC) by specific receptor (gp60)-mediated caveolar transport (see, e.g., John et al., *Am. J. Physiol.*, 284, L187 (2001)). It was hypothesized that albumin-bound paclitaxel in ABX may be transported across tumor microvessel EC by gp60, and this mechanism may be particularly active for ABX as compared to TAX.

A series of experiments were performed to evaluate binding and transport of paclitaxel by human umbilical vein endothelial cells (HUVEC) and human lung microvessel endothelial cells (HLMVEC) for ABX and TAX. Fluorescent paclitaxel (FP) was used as a probe and fluorescent ABX and TAX were formulated with FP to probe the binding and transport of paclitaxel across EC monolayers grown on a transwell apparatus.

Figure 2:
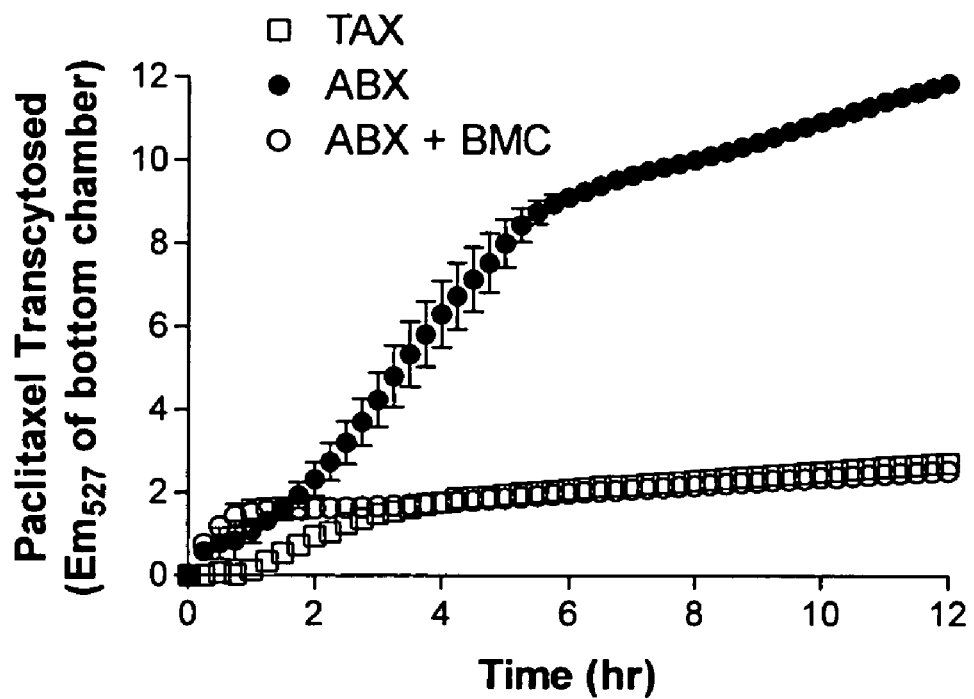
FIG. 2 illustrates transcytosis of paclitaxel across endothelial cell monolayers.

Binding of paclitaxel to cells (HUVEC) was 10× higher for ABX than TAX. The transport of paclitaxel from ABX across EC monolayers was enhanced by 2-3 fold and 2-4 fold for HUVEC and HMVEC, respectively, as compared to TAX. Transport was dependent on albumin. Transport of paclitaxel from ABX was inhibited by the presence of anti-SPARC antibody, which is known to bind gp60, the receptor required for caveolar albumin transcytosis. Known inhibitors of calveolar transcytosis, NEM and β-methyl cyclodextrin (BMC), also inhibited the transport of paclitaxel from ABX across the endothelial monolayers (FIG. 2). Inhibition of caveolar transport decreased transport of P from ABX to the level of TAX transport.

These results demonstrate that paclitaxel from ABX is actively transported across EC by gp60-mediated caveolar transcytosis, whereas P from TAX appears to be transported at a 2-4 fold lower rate primarily by a paracellular (non-caveolar) mechanism. This pathway may in part be responsible for increased intratumoral concentrations of paclitaxel seen for ABX relative to TAX. Cremophor in TAX inhibits transcytosis of paclitaxel across endothelial cells.

EXAMPLE 3

This example illustrates the expression of surface SPARC in MX-1 tumor cells.

MX-1 cells were cultured on a coverslip and stained with an antibody directed against human SPARC using methods known in the art. Antibody staining was observed, which demonstrates that MX-1 is expressing SPARC. These results suggest that SPARC expression detected in MX-1 tumor cells is a result of SPARC secretion by MX-1 tumor cells. Staining was more intense for MX-1 tumor cells than that of normal primary cells such as HUVEC (human umbilical vein endothelial cells), HLMVEC (Human lung microvessel endothelial cells), and HMEC (Human mammary epithelial cells). Although the majority of the SPARC staining was internal SPARC, significant level of surface SPARC was detected as demonstrated by confocal miscroscopy and staining of unpermeabilized cells.

EXAMPLE 4

This example illustrates the internalization of labeled albumin into MX-1 tumor cells and colocalization within the MX-1 cell with intracellular SPARC expression.

MX-1 cells were cultured on a coverslip and permeabilized with suitable agents. Cells were exposed to fluorescent albumin and following washing were exposed to SPARC antibody. This was followed by exposure to a secondary antibodies having a different fluorescent tag than the albumin. It was surprisingly observed that the labeled albumin colocalised with the presence of SPARC within the cell indicating that albumin was rapidly internalized and targeted intracellular SPARC.

EXAMPLE 5

This example demonstrates an increase in endothelial transcytosis via gp60 (albumin receptor) of pharmaceutical compositions comprising paclitaxel and albumin as compared to Taxol.

Human lung microvessel endothelial cells (HLMVEC) were grown to confluence on a transwell. The inventive pharmaceutical composition comprising paclitaxel and albumin, or Taxol containing fluorescent paclitaxel (Flutax) at a concentration of 20 µg/mL, was added to the upper transwell chamber.

The transport of paclitaxel by transcytosis from the upper chamber to the lower chamber was monitored continuously using a fluorometer. A control containing only Flutax without albumin was also used. The control with Flutax showed no transport, validating the integrity of the confluent HLMVEC monolayer. Transport of paclitaxel from the albumin-paclitaxel composition was much faster than paclitaxel from Taxol in the presence of 5% HSA (physiological concentration). Transport rate constants ($K_t$) for the albumin-paclitaxel composition and Taxol were 1.396 $h^{-1}$ and 0.03 $h^{-1}$, respectively. The total amount of paclitaxel transported across the monolayer was three times higher for the albumin-paclitaxel composition than Taxol. Thus, the use of albumin or other suitable mimetic including aantibodies or fragments against the gp60 recepetor or other endothelial cell receptor can assist in the transport of a desired therapeutic agent across the endothelial barrier into the tumor interstitium.

EXAMPLE 6

This example illustrates the overexpression of SPARC protein in human breast carcinoma cells.

SPARC expression in human breast carcinoma cells was determined using a tumor array from Cybrdi, Inc. (Gaithersburg, Md.). The results of this analysis are set forth in Table 1. Intensity of staining was scored from "Negative" to 4+, with the higher number corresponding to greater intensity of overexpression. 49% of breast carcinoma stained positive (2+ and above) for SPARC, as compared to 1% of normal tissue (p<0.0001).

TABLE 1

|  | SPARC Staining (%) | | | | | |
| --- | --- | --- | --- | --- | --- | --- |
|  | Negative | −/+ | 1+ | 2+ | 3+ | 4+ |
| Carcinoma Cells | 31 (34%) | 14 (15%) | 1 (1%) | 11 (12%) | 9 (10%) | 25 (27%) |
| Normal Cells | 93 (89%) | 7 (7%) | 4 (4%) | 1 (1%) | 0 (0%) | 0 (0%) |

EXAMPLE 7

This example demonstrate the specific binding of anti-SPARC antibody to SPARC.

Whole cell extract was prepared from HUVEC cells by sonication. The protein was separated by 5-15% SDS- PAGE, transferred onto PVDF membrane and visualized with a polyclonal antibody against SPARC and a monoclonal antibody against SPARC. Both antibodies reacted to a single band at 38 kDa, the correct molecular weight for SPARC. When MX-1 was analyzed by the same method, SPARC was detected in both the clarified cell lysate or the membrane rich membrane fraction.

EXAMPLE 8

This example demonstrates correlation of SPARC overexpression with high response rates using nanoparticle albumin-bound paclitaxel (ABI-007) in squamous head and neck cancers.

In phase I and II clinical studies of patients with squamous cell carcinoma (SCC) of head and neck (H&N) and anal canal, response rates of 78% and 64% were observed, respectively, for intra-arterially delivered Nanoparticle Albumin-Bound Paclitaxel (Abraxane, ABX or ABI-007) (see, e.g., Damascelli et al., Cancer, 92(10), 2592-2602 (2001), and Damascelli et al., AJR, 181, 253-260 (2003)). In comparing in vitro cytoxicity of ABX and Taxol (TAX), we observed that a squamous cervix (A431) line demonstrated improved $IC_{50}$s for ABX (0.004 µg/ml) vs TAX (0.012 µg/ml). Albumin-mediated transendothelial caveolar transport of paclitaxel (P) and increased intratumoral accumulation of P for ABX vs TAX was demonstrated recently (see, e.g., Desai, SABCS 2003). Human H&N tumor tissues (n=119) and normal human H&N tissue (n=15) were immunostained and scored (0-4) for SPARC staining using a tumor and normal tissue array. Immunostaining was performed using polyclonal rabbit anti-SPARC antibody. SPARC was overexpressed (score >2) in 60% (72/119) of the H&N tumors versus 0% (0/15) in normal tissues (p<0.0001). This may explain the high single-agent activity of ABX seen previously in squamous H&N cancers due to binding of albumin-bound paclitaxel to SPARC expressed in these tumors.

In a new phase I dose escalation study (ABX given IV over 30 minutes q3w), a subset of head and neck cancer patients (n=3) were analyzed for response to ABX. In the phase I study, 2/3 H&N patients achieved partial response (PR) after 2 cycles of treatment at dose levels of 135 mg/m$^2$ (1 pt) and 225 mg/m$^2$ (1 pt). A third patient at 260 mg/m$^2$ progressed. Tumor tissues from these patients were stained for SPARC and 1 responding patients showed strong overexpression for SPARC.

In another phase II clinical study of patients with squamous cell carcinoma (SCC) of head and neck (H&N) treated with intra-arterial Abraxane, an overall response rate of 68% was noted. In 10 responding patients whose tissues were analyzed for SPARC staining, 70% were found to strongly overexpress SPARC.

EXAMPLE 9

This example demonstrates the cloning and sequencing of a human SPARC cDNA which encodes a Q3 SPARC deletion mutant polypeptide.

A normal human prostate cDNA library was screened for clones containing SPARC cDNAs using a high throughput screening method as described in U.S. Pat. No. 6,316,193. A SPARC cDNA clone was isolated and sequenced using primers distributed along its length to obtain the complete cDNA sequence (see FIG. 3). Sequencing data were assembled using the Vector NTI program. The reference Genebank sequence for human SPARC cDNA (NM 003118 [gi:48675809], last updated on Dec. 4, 2005) was used for the assembly. The distribution of the sequencing data for each primer is shown in FIG. 3 and the results of the individual sequence reactions in FIG. 4.

The complete assembled 2,956 base pair cDNA sequence, SEQ ID NO: 3, is shown in FIG. 5. The bold/underlined trinucleotides in FIG. 5 are, respectively, the translational start site for the encoded Q3 SPARC deletion mutant polypeptide and the first codon in the encoded mature Q3 SPARC deletion mutant polypeptide (the amino acid sequence after the 17 amino acid leader sequence). The SEQ ID NO: 3 open reading frame encodes a full length SPARC protein with a deletion of the glutamine corresponding to the glutamine at position 20 in the wild type SPARC amino acid sequence (SEQ ID NO: 1).

The translation of the full length open reading frame encoding the Q3 SPARC deletion mutant polypeptide from SEQ ID NO: 3 is shown in FIG. 6. The start codon of this open reading frame is at nucleotide 87 of SEQ ID NO: 3 and the open reading frame ends at nucleotide 992 of SEQ ID NO: 3. The translated amino acid sequence is 302 codons long and is disclosed by SEQ ID NO: 4. The DNA sequence of the full length open reading frame is disclosed by SEQ ID NO: 5.

FIG. 7 shows the amino acid sequence of the mature Q3 SPARC deletion mutant polypeptide (the sequence without the 17 amino acid leader sequence) encoded by SEQ ID NO: 3. This results from a translation of nucleotides 138 through 992 of SEQ ID NO: 3. The mature Q3 SPARC deletion mutant polypeptide is SEQ ID NO: 2 and the DNA sequence encoding the mature Q3 SPARC deletion mutant polypeptide is SEQ ID NO: 6.

EXAMPLE 10

This example demonstrates the identification of the deletion of the glutamine at position 20 in the wild type SPARC amino acid sequence (SEQ ID NO: 1) in the SPARC polypeptide encoded by SEQ ID NO: 3 (a "Q3 SPARC deletion").

Alignment of SEQ ID NO: 3 DNA sequence with the human SPARC cDNA sequence deposited in Genebank (FIG. 8) demonstrated that SEQ ID NO: 3 contains a 3 base pair deletion (boldface) corresponding to the codon encoding the Q3 of the mature SPARC protein. In addition, alignment of the translated SPARC open reading from SEQ ID NO: 3, SEQ ID NO: 4, demonstrated deletion of the glutamine at position 20 in the wild type SPARC amino acid sequence (the Q3 amino acid) (FIG. 9).

EXAMPLE 11

This example demonstrates the evolutionary conservation of the glutamine residues at amino acid positions 3 and 4 of the mature SPARC protein (the "Q3Q4" amino acids).

Examination of the amino acid sequence for SPARC across the phylogenetic tree revealed the conservation of Q3Q4 across mammal and amphibian. A single glutamine was only observed in rat and chicken. Neither Q3 nor Q3Q4 was observed in fish. The skeletal structures of fish and bird are much lighter than that of mammal and amphibian, suggesting that this site for tranglutaminase is involved in the formation of highly crosslinked and structurally compact skeletal structure. SPARC with only Q3 could be free to participate in non-skeletal functions such as angiogenesis, tumor growth, albumin binding, and the like.

The conservation of the Q3Q4 pair of glutamines in higher organisms suggests that a Q3 SPARC deletion mutant polypeptide could have novel properties.

EXAMPLE 12

This example demonstrates the subcloning of a Q3 SPARC deletion mutant polypeptide encoding cDNA into an expression vector.

SPARC cDNA was excised with Not I and subcloned into the Not I site of pCDNA3.1 to give rise to pVT1000Q3. The orientation of the insert relative to CMV promoter was confirmed by restriction digest (Not I, Eco RV, Eco RI, Ssp I) and sequencing. Restriction digestion gave rise to fragments with the predicted size for all four restriction enzymes (FIG. 11). The restriction map for the pVT1000Q3 construct is shown in FIG. 12.

The inventors expect that pVT1000Q3 will readily transfect the CHO, MDA-MB-231, PC3, HT29, and MX-1 cell lines using transfection methods well known to those of ordinary skill in the art.

EXAMPLE 13

This example demonstrates primer directed mutagenesis by the insertion of the Q3 into pVT1000Q3 generating a sequence encoding a wild type SPARC polypeptide.

A polymerase chain reaction (PCR) primer containing the Q3 codon (see FIG. 13) was used in primer directed mutagenesis method well known to those of ordinary skill in the art. The resulting plasmid, pVT1000wt, exhibited the expected wild type Q3Q4 SPARC sequence.

EXAMPLE 14

This example demonstrates the PCR detection of a nucleic acid encoding a Q3 SPARC deletion mutant polypeptide, i.e., the "Q3 mutation."

The location and sequence of primers designed to detect the Q3 mutation and the wild type form of SPARC cDNA are shown in FIG. 14. The inventive PCR primers SPARC-FQ3, SPARC-FWT, and SPARC-FQ3&W (SEQ ID NOS: 7-9, respectively) as forward primers and inventive molecule SPARC-RQ3&W (SEQ ID NO: 10) as an inventive reverse PCR primer were used in a standard reverse transcription PCR (RT-PCR) reaction well known to those of ordinary skill in the art. The Q3 mutation and wild type sequences were distinguished using the inventive primers in a PCR reaction followed by gel electrophoresis as shown in Table 2.

TABLE 2

| Reaction Mix | Primers | Results for Q3 mutant | Results for wild type |
|---|---|---|---|
| #1 | FQ3 + RQ3&WT | 309 base pair band | No products |
| #2 | FQ3 + FQ3&W + RQ3&WT | 309 + 222 base pair bands | 222 base pair band |
| #3 | FW + RQ3&WT | No products | 309 base pair band |
| #4 | FW3 + FQ3&WT + RQ3&WT | 222 base pair band | 309 + 222 base pair bands |

The PCR amplification conditions used were: a hot start of 95° C. for 10 minutes, followed by 30 cycles of 95° C. for 30 Sec., 62° C. for 30 Sec., 72° C. for 40 Sec., and final extension at 72° C. for 10 minutes. pVT1000Q3, which carries the Q3 mutation, and pVT1000wt, which carries the wild type SPARC, are used as controls. The Q3 mutation was detected by the absence of the 309 base pair product with reaction mixes #3 and #4 and the presence of the 309 base pair product with reaction mixes #1 and #2. The wild type sequence was detected as presence of the 309 base pair product with reaction mixes #3 and #4 and the absence of the 309 base pair product with reaction mix #2. With reaction mix #1, the wild type sequence yielded a 309 base pair product but, at much weaker level than with reaction mixes #3 and #4. Therefore, reaction mix #3 is more robust for detecting wild type SPARC sequences (non-Q3 mutant sequences) (FIG. 15).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. An isolated secreted protein acidic and rich in cysteine (SPARC) polypeptide, wherein the polypeptide comprises the amino acid sequence of SEQ ID NO: 2.

2. A composition comprising the polypeptide of claim 1 and a pharmaceutically acceptable carrier.

3. The composition of claim 2, wherein the polypeptide is coupled to a therapeutic agent.

4. The composition of claim 3, wherein the therapeutic agent is a radionuclide, drug, polypeptide or toxin.

5. The composition of claim 2, wherein the polypeptide is coupled to a polyethylene glycol.

* * * * *

SEQUENCE LISTING

<160> NUMBER OF SEQ ID NOS: 10

<210> SEQ ID NO 1
<211> LENGTH: 303

```
<212> TYPE: PRT
<213> ORGANISM: Homo sapiens

<400> SEQUENCE: 1

Met Arg Ala Trp Ile Phe Phe Leu Leu Cys Leu Ala Gly Arg Ala Leu
1               5                   10                  15

Ala Ala Pro Gln Gln Glu Ala Leu Pro Asp Glu Thr Glu Val Val Glu
            20                  25                  30

Glu Thr Val Ala Glu Val Thr Glu Val Ser Val Gly Ala Asn Pro Val
        35                  40                  45

Gln Val Glu Val Gly Glu Phe Asp Asp Gly Ala Glu Glu Thr Glu Glu
50                  55                  60

Glu Val Val Ala Glu Asn Pro Cys Gln Asn His His Cys Lys His Gly
65                  70                  75                  80

Lys Val Cys Glu Leu Asp Glu Asn Asn Thr Pro Met Cys Val Cys Gln
                85                  90                  95

Asp Pro Thr Ser Cys Pro Ala Pro Ile Gly Glu Phe Glu Lys Val Cys
            100                 105                 110

Ser Asn Asp Asn Lys Thr Phe Asp Ser Ser Cys His Phe Phe Ala Thr
        115                 120                 125

Lys Cys Thr Leu Glu Gly Thr Lys Lys Gly His Lys Leu His Leu Asp
130                 135                 140

Tyr Ile Gly Pro Cys Lys Tyr Ile Pro Pro Cys Leu Asp Ser Glu Leu
145                 150                 155                 160

Thr Glu Phe Pro Leu Arg Met Arg Asp Trp Leu Lys Asn Val Leu Val
                165                 170                 175

Thr Leu Tyr Glu Arg Asp Glu Asp Asn Asn Leu Leu Thr Glu Lys Gln
            180                 185                 190

Lys Leu Arg Val Lys Lys Ile His Glu Asn Glu Lys Arg Leu Glu Ala
        195                 200                 205

Gly Asp His Pro Val Glu Leu Leu Ala Arg Asp Phe Glu Lys Asn Tyr
210                 215                 220

Asn Met Tyr Ile Phe Pro Val His Trp Gln Phe Gly Gln Leu Asp Gln
225                 230                 235                 240

His Pro Ile Asp Gly Tyr Leu Ser His Thr Glu Leu Ala Pro Leu Arg
                245                 250                 255

Ala Pro Leu Ile Pro Met Glu His Cys Thr Thr Arg Phe Phe Glu Thr
            260                 265                 270

Cys Asp Leu Asp Asn Asp Lys Tyr Ile Ala Leu Asp Glu Trp Ala Gly
        275                 280                 285

Cys Phe Gly Ile Lys Gln Lys Asp Ile Asp Lys Asp Leu Val Ile
290                 295                 300

<210> SEQ ID NO 2
<211> LENGTH: 285
<212> TYPE: PRT
<213> ORGANISM: Homo sapiens

<400> SEQUENCE: 2

Ala Pro Gln Glu Ala Leu Pro Asp Glu Thr Glu Val Val Glu Glu Thr
1               5                   10                  15

Val Ala Glu Val Thr Glu Val Ser Val Gly Ala Asn Pro Val Gln Val
            20                  25                  30

Glu Val Gly Glu Phe Asp Asp Gly Ala Glu Glu Thr Glu Glu Glu Val
        35                  40                  45
```

```
Val Ala Glu Asn Pro Cys Gln Asn His His Cys Lys His Gly Lys Val
 50                  55                  60
Cys Glu Leu Asp Glu Asn Asn Thr Pro Met Cys Val Cys Gln Asp Pro
 65                      70                  75                  80
Thr Ser Cys Pro Ala Pro Ile Gly Glu Phe Glu Lys Val Cys Ser Asn
                 85                  90                  95
Asp Asn Lys Thr Phe Asp Ser Ser Cys His Phe Phe Ala Thr Lys Cys
            100                 105                 110
Thr Leu Glu Gly Thr Lys Lys Gly His Lys Leu His Leu Asp Tyr Ile
        115                 120                 125
Gly Pro Cys Lys Tyr Ile Pro Pro Cys Leu Asp Ser Glu Leu Thr Glu
    130                 135                 140
Phe Pro Leu Arg Met Arg Asp Trp Leu Lys Asn Val Leu Val Thr Leu
145                 150                 155                 160
Tyr Glu Arg Asp Glu Asp Asn Asn Leu Leu Thr Glu Lys Gln Lys Leu
                165                 170                 175
Arg Val Lys Lys Ile His Glu Asn Glu Lys Arg Leu Glu Ala Gly Asp
            180                 185                 190
His Pro Val Glu Leu Leu Ala Arg Asp Phe Glu Lys Asn Tyr Asn Met
        195                 200                 205
Tyr Ile Phe Pro Val His Trp Gln Phe Gly Gln Leu Asp Gln His Pro
    210                 215                 220
Ile Asp Gly Tyr Leu Ser His Thr Glu Leu Ala Pro Leu Arg Ala Pro
225                 230                 235                 240
Leu Ile Pro Met Glu His Cys Thr Thr Arg Phe Glu Thr Cys Asp
                245                 250                 255
Leu Asp Asn Asp Lys Tyr Ile Ala Leu Asp Glu Trp Ala Gly Cys Phe
            260                 265                 270
Gly Ile Lys Gln Lys Asp Ile Asp Lys Asp Leu Val Ile
        275                 280                 285

<210> SEQ ID NO 3
<211> LENGTH: 2956
<212> TYPE: DNA
<213> ORGANISM: Homo sapiens

<400> SEQUENCE: 3
ctccacattc ccgcggtcct tcagactgcc cggagagcgc gctctgcctg ccgcctgcct      60
gcctgccact gagggttccc agcaccatga gggcctggat cttctttctc ctttgcctgg     120
ccgggagggc cttggcagcc cctcaagaag ccctgcctga tgagacagag gtggtggaag     180
aaactgtggc agaggtgact gaggtatctg tgggagctaa tcctgtccag gtggaagtag     240
gagaatttga tgatggtgca gaggaaaccg aagaggaggt ggtggcggaa atccctgcc      300 agaaccacca ctgcaaacac ggcaaggtgt gcgagctgga tgagaacaac accccccatgt    360 gcgtgtgcca ggaccccacc agctgcccag ccccattgg cgagtttgag aaggtgtgca     420
gcaatgacaa caagaccttc gactcttcct gccacttctt tgccacaaag tgcaccctgg     480
agggcaccaa gaagggccac aagctccacc tggactacat cgggccttgc aaatacatcc     540 cccccttgcct ggactctgag ctgaccgaat tcccctgcg catgcgggac tggctcaaga     600
acgtcctggt caccctgtat gagagggatg aggacaacaa ccttctgact gagaagcaga     660
agctgcgggt gaagaagatc catgagaatg agaagcgcct ggaggcagga gaccaccccg     720
tggagctgct ggcccgggac ttcgagaaga actataacat gtacatcttc cctgtacact     780
```

```
ggcagttcgg ccagctggac cagcacccca ttgacgggta cctctcccac accgagctgg    840
ctccactgcg tgctcccctc atccccatgg agcattgcac cacccgcttt ttcgagacct    900
gtgacctgga caatgacaag tacatcgccc tggatgagtg ggccggctgc ttcggcatca    960
agcagaagga tatcgacaag gatcttgtga tctaaatcca ctccttccac agtaccggat   1020
tctctcttta accctcccct tcgtgttttc cccaatgttt aaaatgtttg gatggtttgt   1080
tgttctgcct ggagacaagg tgctaacata gatttaagtg aatacattaa cggtgctaaa   1140
aatgaaaatt ctaacccaag acatgacatt cttagctgta acttaactat taaggccttt   1200
tccacacgca ttaatagtcc cattttctc ttgccatttg tagctttgcc cattgtctta   1260
ttggcacatg ggtggacacg gatctgctgg gctctgcctt aaacacacat tgcagcttca   1320
acttttctct ttagtgttct gtttgaaact aatacttacc gagtcagact ttgtgttcat   1380
ttcatttcag ggtcttggct gcctgtgggc ttccccaggt ggcctggagg tgggcaaagg   1440
gaagtaacag acacacgatg ttgtcaagga tggttttggg actagaggct cagtggtggg   1500
agagatccct gcagaaccca ccaaccagaa cgtggtttgc ctgaggctgt aactgagaga   1560
aagattctgg ggctgtgtta tgaaaatata gacattctca cataagccca gttcatcacc   1620
atttcctcct ttacctttca gtgcagtttc ttttcacatt aggctgttgg ttcaaacttt   1680
tgggagcacg gactgtcagt tctctgggaa gtggtcagcg catcctgcag ggcttctcct   1740
cctctgtctt ttggagaacc agggctcttc tcaggggctc tagggactgc caggctgttt   1800
cagccaggaa ggccaaaatc aagagtgaga tgtagaaagt tgtaaaatag aaaaagtgga   1860
gttggtgaat cggttgttct ttcctcacat ttggatgatt gtcataaggt ttttagcatg   1920
ttcctccttt tcttcaccct cccctttttt cttctattaa tcaagagaaa cttcaaagtt   1980
aatgggatgg tcggatctca caggctgaga actcgttcac ctccaagcat ttcatgaaaa   2040
agctgcttct tattaatcat acaaactctc accatgatgt gaagagtttc acaaatcctt   2100
caaaataaaa agtaatgact tagaaactgc cttcctgggt gatttgcatg tgtcttagtc   2160
ttagtcacct tattatcctg acacaaaaac acatgagcat acatgtctac acatgactac   2220
acaaatgcaa acctttgcaa acacattatg cttttgcaca cacacacctg tacacacaca   2280
ccggcatgtt tatacacagg gagtgtatgg ttcctgtaag cactaagtta gctgttttca   2340
tttaatgacc tgtggtttaa ccctttttgat cactaccacc attatcagca ccagactgag   2400
cagctatatc cttttattaa tcatggtcat tcattcattc attcattcac aaaatatta    2460 tgatgtattt actctgcacc aggtcccatg ccaagcactg gggacacagt tatggcaaag   2520
tagacaaagc atttgttcat ttggagctta gagtccagga ggaatacatt agataatgac   2580
acaatcaaat ataattgca agatgtcaca ggtgtgatga agggagagta ggagagacca   2640
tgagtatgtg taacaggagg acacagcatt attctagtgc tgtactgttc cgtacggcag   2700
ccactaccca catgtaactt tttaagattt aaatttaaat tagttaacat tcaaaacgca   2760 gctcccccaat cacactagca acatttcaag tgcttgagag ccatgcatga ttagtggtta   2820
ccctattgaa taggtcagaa gtagaatctt ttcatcatca cagaaagttc tattggacag   2880
tgctcttcta gatcatcata agactacaga gcactttca aagctcatgc atgttcatca    2940
tgttagtgtc gtattt                                                   2956

<210> SEQ ID NO 4
<211> LENGTH: 302
<212> TYPE: PRT
<213> ORGANISM: Homo sapiens
```

<400> SEQUENCE: 4

```
Met Arg Ala Trp Ile Phe Phe Leu Leu Cys Leu Ala Gly Arg Ala Leu
1               5                   10                  15
Ala Ala Pro Gln Glu Ala Leu Pro Asp Glu Thr Glu Val Val Glu Glu
            20                  25                  30
Thr Val Ala Glu Val Thr Glu Val Ser Val Gly Ala Asn Pro Val Gln
        35                  40                  45
Val Glu Val Gly Glu Phe Asp Asp Gly Ala Glu Thr Glu Glu Glu
    50                  55                  60
Val Val Ala Glu Asn Pro Cys Gln Asn His His Cys Lys His Gly Lys
65                  70                  75                  80
Val Cys Glu Leu Asp Glu Asn Asn Thr Pro Met Cys Val Cys Gln Asp
                85                  90                  95
Pro Thr Ser Cys Pro Ala Pro Ile Gly Glu Phe Glu Lys Val Cys Ser
            100                 105                 110
Asn Asp Asn Lys Thr Phe Asp Ser Ser Cys His Phe Phe Ala Thr Lys
        115                 120                 125
Cys Thr Leu Glu Gly Thr Lys Lys Gly His Lys Leu His Leu Asp Tyr
    130                 135                 140
Ile Gly Pro Cys Lys Tyr Ile Pro Pro Cys Leu Asp Ser Glu Leu Thr
145                 150                 155                 160
Glu Phe Pro Leu Arg Met Arg Asp Trp Leu Lys Asn Val Leu Val Thr
                165                 170                 175
Leu Tyr Glu Arg Asp Glu Asp Asn Asn Leu Leu Thr Glu Lys Gln Lys
            180                 185                 190
Leu Arg Val Lys Lys Ile His Glu Asn Glu Lys Arg Leu Glu Ala Gly
        195                 200                 205
Asp His Pro Val Glu Leu Leu Ala Arg Asp Phe Glu Lys Asn Tyr Asn
    210                 215                 220
Met Tyr Ile Phe Pro Val His Trp Gln Phe Gly Gln Leu Asp Gln His
225                 230                 235                 240
Pro Ile Asp Gly Tyr Leu Ser His Thr Glu Leu Ala Pro Leu Arg Ala
                245                 250                 255
Pro Leu Ile Pro Met Glu His Cys Thr Thr Arg Phe Phe Glu Thr Cys
            260                 265                 270
Asp Leu Asp Asn Asp Lys Tyr Ile Ala Leu Asp Glu Trp Ala Gly Cys
        275                 280                 285
Phe Gly Ile Lys Gln Lys Asp Ile Asp Lys Asp Leu Val Ile
    290                 295                 300
```

<210> SEQ ID NO 5
<211> LENGTH: 909
<212> TYPE: DNA
<213> ORGANISM: Homo sapiens

<400> SEQUENCE: 5

```
atgagggcct ggatcttctt tctcctttgc ctggccggga gggccttggc agcccctcaa    60
gaagccctgc ctgatgagac agaggtggtg aagaaactg tggcagaggt gactgaggta   120
tctgtgggag ctaatcctgt ccaggtgaa gtaggagaat tgatgatgg tgcagaggaa   180
accgaagagg aggtggtggc ggaaaatccc tgccagaacc accactgcaa acacggcaag   240
gtgtgcgagc tggatgagaa caacaccccc atgtgcgtgt gccaggaccc caccagctgc   300
ccagccccca ttggcgagtt tgagaaggtg tgcagcaatg acaacaagac cttcgactct   360
```

```
tcctgccact tctttgccac aaagtgcacc ctggagggca ccaagaaggg ccacaagctc    420
cacctggact acatcgggcc ttgcaaatac atccccccctt gcctggactc tgagctgacc    480
gaattccccc tgcgcatgcg ggactggctc aagaacgtcc tggtcaccct gtatgagagg    540
gatgaggaca acaaccttct gactgagaag cagaagctgc gggtgaagaa gatccatgag    600
aatgagaagc gcctggaggc aggagaccac cccgtggagc tgctggcccg ggacttcgag    660
aagaactata acatgtacat cttccctgta cactggcagt tcggccagct ggaccagcac    720
cccattgacg ggtacctctc ccacaccgag ctggctccac tgcgtgctcc cctcatcccc    780
atggagcatt gcaccacccg ctttttcgag acctgtgacc tggacaatga caagtacatc    840
gccctggatg agtgggccgg ctgcttcggc atcaagcaga aggatatcga caaggatctt    900
gtgatctaa                                                             909

<210> SEQ ID NO 6
<211> LENGTH: 858
<212> TYPE: DNA
<213> ORGANISM: Homo sapiens

<400> SEQUENCE: 6
gcccctcaag aagccctgcc tgatgagaca gaggtggtgg aagaaactgt ggcagaggtg     60
actgaggtat ctgtgggagc taatcctgtc caggtggaag taggagaatt tgatgatggt    120
gcagaggaaa ccgaagagga ggtggtggcg gaaaatccct gccagaacca ccactgcaaa    180
cacggcaagg tgtgcgagct ggatgagaac aacaccccca tgtgcgtgtg ccaggacccc    240
accagctgcc cagcccccat tggcgagttt gagaaggtgt gcagcaatga caacaagacc    300
ttcgactctt cctgccactt ctttgccaca aagtgcaccc tggagggcac caagaagggc    360
cacaagctcc acctggacta catcgggcct tgcaaataca tccccccttg cctggactct    420
gagctgaccg aattccccct gcgcatgcgg gactggctca agaacgtcct ggtcaccctg    480
tatgagaggg atgaggacaa caaccttctg actgagaagc agaagctgcg ggtgaagaag    540
atccatgaga atgagaagcg cctggaggca ggagaccacc ccgtggagct gctggcccgg    600
gacttcgaga agaactataa catgtacatc ttccctgtac actggcagtt cggccagctg    660
gaccagcacc ccattgacgg gtacctctcc cacaccgagc tggctccact gcgtgctccc    720
ctcatcccca tggagcattg caccacccgc ttttttcgaga cctgtgacct ggacaatgac    780
aagtacatcg ccctggatga gtgggccggc tgcttcggca tcaagcagaa ggatatcgac    840
aaggatcttg tgatctaa                                                  858

<210> SEQ ID NO 7
<211> LENGTH: 22
<212> TYPE: DNA
<213> ORGANISM: Homo sapiens

<400> SEQUENCE: 7
agggccttgg cagcccctca ag                                              22

<210> SEQ ID NO 8
<211> LENGTH: 23
<212> TYPE: DNA
<213> ORGANISM: Homo sapiens

<400> SEQUENCE: 8
agggccttgg cagcccctca gca                                             23
```

```
<210> SEQ ID NO 9
<211> LENGTH: 23
<212> TYPE: DNA
<213> ORGANISM: Homo sapiens

<400> SEQUENCE: 9
gaaactgtgg cagaggtgac tga                                              23

<210> SEQ ID NO 10
<211> LENGTH: 25
<212> TYPE: DNA
<213> ORGANISM: Homo sapiens

<400> SEQUENCE: 10
gttgtcattg ctgcacacct tctca                                            25
```